(12) United States Patent
Carrison et al.

(10) Patent No.: US 9,211,116 B2
(45) Date of Patent: Dec. 15, 2015

(54) FISTULA TREATMENT DEVICES AND RELATED METHODS

(75) Inventors: Harold F. Carrison, Pleasanton, CA (US); Yolanda Pacho Huynh, San Jose, CA (US)

(73) Assignee: CURASEAL INC., Santa Clara, CA (US)

( * ) Notice: Subject to any disclaimer, the term of this patent is extended or adjusted under 35 U.S.C. 154(b) by 535 days.

(21) Appl. No.: 13/525,161

(22) Filed: Jun. 15, 2012

(65) Prior Publication Data

US 2013/0006283 A1 Jan. 3, 2013

Related U.S. Application Data

(60) Provisional application No. 61/497,899, filed on Jun. 16, 2011, provisional application No. 61/498,495, filed on Jun. 17, 2011.

(51) Int. Cl.
*A61B 17/04* (2006.01)
*A61B 17/00* (2006.01)
(Continued)

(52) U.S. Cl.
CPC ......... *A61B 17/0401* (2013.01); *A61B 17/0057* (2013.01); *A61B 19/026* (2013.01); *A61B 2017/00641* (2013.01); *A61B 2017/0404* (2013.01); *A61B 2017/0406* (2013.01); *A61B 2017/0409* (2013.01); *A61B 2017/0412* (2013.01); *A61B 2017/0464* (2013.01);
(Continued)

(58) Field of Classification Search
CPC ................. A61B 17/0057; A61B 2017/00641; A61B 17/0401; A61B 17/12022; A61B 2017/00579; A61B 17/12172; A61B 17/1219
USPC .......... 606/151, 191, 194, 197, 198, 213, 232
See application file for complete search history.

(56) References Cited

U.S. PATENT DOCUMENTS

| 2,324,520 A | 7/1943 | Lamson |
| 2,510,766 A | 6/1950 | Surface |
| 2,564,399 A | 8/1951 | Franken |

(Continued)

FOREIGN PATENT DOCUMENTS

| DE | 2637119 A1 | 3/1977 |
| EP | 1985247 A1 | 10/2008 |

(Continued)

OTHER PUBLICATIONS

International Search Report, in connection with International Patent application No. PCT/US2012/042805, Nov. 28, 2012, (pp. 1-5).

(Continued)

*Primary Examiner* — Katherine M Shi
(74) *Attorney, Agent, or Firm* — Dorsey & Whitney LLP

(57) ABSTRACT

Disclosed herein are implantable fistula treatment devices and related methods. The fistula closure device comprises a distal anchor and a proximal anchor attached by a connecting member, such as a suture. Individual porous bodies are threaded directly or indirectly over the connecting member. The distal anchor comprises a plurality of foldable members threaded onto the connecting member. The foldable members are arranged in increasing surface area from distal to proximal, and each is further configured to form a mechanical interfit with adjacent foldable members to reduce sliding between members when they are tensioned together.

21 Claims, 54 Drawing Sheets

(51) Int. Cl.
*A61B 19/02* (2006.01)
*A61B 17/32* (2006.01)

(52) U.S. Cl.
CPC ............... *A61B2017/0496* (2013.01); *A61B 2017/320012* (2013.01); *A61B 2218/002* (2013.01)

(56) References Cited

U.S. PATENT DOCUMENTS

| | | |
|---|---|---|
| 2,934,068 A | 4/1960 | Graham, Jr. et al. |
| 3,447,533 A | 6/1969 | Spicer |
| 3,882,858 A | 5/1975 | Klemm |
| 4,057,535 A | 11/1977 | Lipatova et al. |
| 4,241,735 A | 12/1980 | Chernov |
| 4,365,621 A | 12/1982 | Brundin |
| 4,390,018 A | 6/1983 | Zukowski |
| 4,532,926 A | 8/1985 | O'Holla |
| 4,669,473 A | 6/1987 | Richards et al. |
| 4,705,040 A | 11/1987 | Mueller et al. |
| 4,744,364 A | 5/1988 | Kensey |
| 4,795,438 A | 1/1989 | Kensey et al. |
| 4,836,204 A | 6/1989 | Landymore et al. |
| 4,852,568 A | 8/1989 | Kensey |
| 4,890,612 A | 1/1990 | Kensey |
| 4,917,089 A | 4/1990 | Sideris |
| 4,935,028 A | 6/1990 | Drews |
| 4,983,177 A | 1/1991 | Wolf |
| 5,021,059 A | 6/1991 | Kensey et al. |
| 5,053,046 A | 10/1991 | Janese |
| 5,061,274 A | 10/1991 | Kensey |
| 5,108,421 A | 4/1992 | Fowler |
| 5,122,136 A | 6/1992 | Guglielmi et al. |
| 5,192,301 A | 3/1993 | Kamiya et al. |
| 5,192,302 A | 3/1993 | Kensey et al. |
| 5,222,974 A | 6/1993 | Kensey et al. |
| 5,242,456 A | 9/1993 | Nash et al. |
| 5,258,042 A | 11/1993 | Mehta |
| 5,282,827 A | 2/1994 | Kensey et al. |
| 5,306,254 A | 4/1994 | Nash et al. |
| 5,312,435 A | 5/1994 | Nash et al. |
| 5,334,217 A | 8/1994 | Das |
| 5,350,399 A * | 9/1994 | Erlebacher et al. ............ 606/213 |
| 5,354,295 A | 10/1994 | Guglielmi et al. |
| 5,370,660 A | 12/1994 | Weinstein et al. |
| 5,374,261 A | 12/1994 | Yoon et al. |
| RE34,866 E | 2/1995 | Kensey et al. |
| 5,391,183 A | 2/1995 | Janzen et al. |
| 5,411,520 A | 5/1995 | Nash et al. |
| 5,433,727 A | 7/1995 | Sideris |
| 5,441,517 A | 8/1995 | Kensey et al. |
| 5,522,836 A | 6/1996 | Palermo |
| 5,531,757 A | 7/1996 | Kensey et al. |
| 5,531,759 A | 7/1996 | Kensey et al. |
| 5,540,680 A | 7/1996 | Guglielmi et al. |
| 5,545,178 A | 8/1996 | Kensey et al. |
| 5,549,633 A | 8/1996 | Evans et al. |
| 5,582,619 A | 12/1996 | Ken |
| 5,591,204 A | 1/1997 | Janzen et al. |
| 5,593,422 A | 1/1997 | Muijs Van de Moer et al. |
| 5,609,628 A | 3/1997 | Keranen |
| 5,620,461 A | 4/1997 | Muijs Van De Moer et al. |
| 5,624,449 A | 4/1997 | Pham et al. |
| 5,643,254 A | 7/1997 | Scheldrup et al. |
| 5,645,558 A | 7/1997 | Horton |
| 5,649,949 A | 7/1997 | Wallace et al. |
| 5,662,681 A | 9/1997 | Nash et al. |
| 5,669,905 A | 9/1997 | Scheldrup et al. |
| 5,676,689 A | 10/1997 | Kensey et al. |
| 5,681,334 A | 10/1997 | Evans et al. |
| 5,700,277 A | 12/1997 | Nash et al. |
| 5,707,393 A | 1/1998 | Kensey et al. |
| 5,713,891 A | 2/1998 | Poppas |
| 5,725,552 A | 3/1998 | Kotula et al. |
| 5,743,905 A | 4/1998 | Eder et al. |
| 5,749,891 A | 5/1998 | Ken et al. |
| 5,752,974 A | 5/1998 | Rhee et al. |
| 5,766,219 A | 6/1998 | Horton |
| 5,782,860 A | 7/1998 | Epstein et al. |
| 5,785,679 A | 7/1998 | Abolfathi et al. |
| 5,810,884 A | 9/1998 | Kim |
| 5,824,054 A | 10/1998 | Khosravi et al. |
| 5,833,705 A | 11/1998 | Ken et al. |
| 5,853,418 A | 12/1998 | Ken et al. |
| 5,855,578 A | 1/1999 | Guglielmi et al. |
| 5,861,004 A | 1/1999 | Kensey et al. |
| 5,879,366 A | 3/1999 | Shaw et al. |
| 5,904,703 A | 5/1999 | Gilson |
| 5,911,731 A | 6/1999 | Pham et al. |
| 5,916,236 A | 6/1999 | Muijs Van de Moer et al. |
| 5,925,037 A | 7/1999 | Guglielmi et al. |
| 5,928,226 A | 7/1999 | Guglielmi et al. |
| 5,935,145 A | 8/1999 | Villar et al. |
| 5,935,147 A | 8/1999 | Kensey et al. |
| 5,944,714 A | 8/1999 | Guglielmi et al. |
| 5,947,962 A | 9/1999 | Guglielmi et al. |
| 5,957,900 A | 9/1999 | Ouchi |
| 5,957,948 A | 9/1999 | Mariant |
| 5,976,126 A | 11/1999 | Guglielmi |
| 5,989,281 A | 11/1999 | Barbut et al. |
| 5,990,379 A | 11/1999 | Gregory |
| 6,004,338 A | 12/1999 | Ken et al. |
| 6,007,563 A | 12/1999 | Nash et al. |
| 6,010,498 A | 1/2000 | Guglielmi |
| 6,010,517 A | 1/2000 | Baccaro |
| 6,013,084 A | 1/2000 | Ken et al. |
| 6,033,423 A | 3/2000 | Ken et al. |
| 6,045,569 A | 4/2000 | Kensey et al. |
| 6,045,570 A | 4/2000 | Epstein et al. |
| 6,056,768 A | 5/2000 | Cates et al. |
| 6,063,100 A | 5/2000 | Diaz et al. |
| 6,066,133 A | 5/2000 | Guglielmi et al. |
| 6,077,260 A | 6/2000 | Wheelock et al. |
| 6,080,183 A | 6/2000 | Tsugita et al. |
| 6,083,220 A | 7/2000 | Guglielmi et al. |
| 6,087,552 A | 7/2000 | Gregory |
| 6,090,125 A | 7/2000 | Horton |
| 6,090,130 A | 7/2000 | Nash et al. |
| 6,171,326 B1 | 1/2001 | Ferrera et al. |
| 6,179,857 B1 | 1/2001 | Diaz et al. |
| 6,179,863 B1 | 1/2001 | Kensey et al. |
| 6,183,491 B1 | 2/2001 | Lulo |
| 6,187,027 B1 | 2/2001 | Mariant et al. |
| 6,190,400 B1 | 2/2001 | Van De Moer et al. |
| 6,203,563 B1 | 3/2001 | Fernandez |
| 6,231,562 B1 | 5/2001 | Khosravi et al. |
| 6,238,403 B1 | 5/2001 | Greene et al. |
| 6,270,495 B1 | 8/2001 | Palermo |
| 6,287,318 B1 | 9/2001 | Villar et al. |
| 6,296,658 B1 | 10/2001 | Gershony et al. |
| 6,306,153 B1 | 10/2001 | Kurz et al. |
| 6,315,787 B1 | 11/2001 | Tsugita et al. |
| 6,371,972 B1 | 4/2002 | Wallace et al. |
| 6,383,204 B1 | 5/2002 | Ferrera |
| 6,409,721 B1 | 6/2002 | Wheelock et al. |
| 6,454,780 B1 | 9/2002 | Wallace |
| 6,476,069 B2 | 11/2002 | Krall et al. |
| 6,503,527 B1 | 1/2003 | Whitmore et al. |
| 6,538,026 B1 | 3/2003 | Krall et al. |
| 6,551,303 B1 | 4/2003 | Van Tassel et al. |
| 6,551,305 B2 | 4/2003 | Ferrera et al. |
| 6,551,340 B1 | 4/2003 | Konya et al. |
| 6,565,601 B2 | 5/2003 | Wallace et al. |
| 6,589,230 B2 | 7/2003 | Gia et al. |
| 6,589,236 B2 | 7/2003 | Wheelock et al. |
| 6,592,566 B2 | 7/2003 | Kipke et al. |
| 6,599,308 B2 | 7/2003 | Amplatz |
| 6,605,101 B1 | 8/2003 | Schaefer et al. |
| 6,613,037 B2 | 9/2003 | Khosravi et al. |
| 6,623,493 B2 | 9/2003 | Wallace et al. |
| 6,623,508 B2 | 9/2003 | Shaw et al. |
| 6,635,069 B1 | 10/2003 | Teoh et al. |
| 6,638,291 B1 | 10/2003 | Ferrera et al. |
| 6,656,173 B1 | 12/2003 | Palermo |

(56) References Cited

U.S. PATENT DOCUMENTS

| | | |
|---|---|---|
| 6,656,201 B2 | 12/2003 | Ferrera et al. |
| 6,656,206 B2 | 12/2003 | Corcoran et al. |
| 6,660,020 B2 | 12/2003 | Wallace et al. |
| 6,676,971 B2 | 1/2004 | Goupil et al. |
| 6,682,546 B2 | 1/2004 | Amplatz |
| 6,699,484 B2 | 3/2004 | Whitmore et al. |
| 6,723,108 B1 | 4/2004 | Jones et al. |
| 6,730,108 B2 | 5/2004 | Van Tassel et al. |
| 6,764,500 B1 | 7/2004 | Muijs Van De Moer et al. |
| 6,790,218 B2 | 9/2004 | Jayaraman |
| 6,872,218 B2 | 3/2005 | Kurz et al. |
| 6,921,410 B2 | 7/2005 | Porter |
| 6,949,113 B2 | 9/2005 | Van Tassel et al. |
| 6,953,468 B2 | 10/2005 | Jones et al. |
| 6,974,862 B2 | 12/2005 | Ringeisen et al. |
| 6,979,344 B2 | 12/2005 | Jones et al. |
| 6,994,717 B2 | 2/2006 | Konya et al. |
| 6,997,918 B2 | 2/2006 | Soltesz et al. |
| 7,011,677 B2 | 3/2006 | Wallace et al. |
| 7,033,348 B2 | 4/2006 | Alfano et al. |
| 7,049,348 B2 | 5/2006 | Evans et al. |
| 7,070,608 B2 | 7/2006 | Kurz et al. |
| 7,166,133 B2 | 1/2007 | Evans et al. |
| 7,169,168 B2 | 1/2007 | Muijs Van De Moer et al. |
| 7,179,276 B2 | 2/2007 | Barry et al. |
| 7,182,774 B2 | 2/2007 | Barry et al. |
| 7,214,765 B2 | 5/2007 | Ringeisen et al. |
| 7,294,123 B2 | 11/2007 | Jones et al. |
| 7,316,701 B2 | 1/2008 | Ferrera et al. |
| 7,323,000 B2 | 1/2008 | Monstdt et al. |
| 7,326,225 B2 | 2/2008 | Ferrera et al. |
| 7,331,981 B2 | 2/2008 | Cates et al. |
| 7,485,087 B2 | 2/2009 | Burgard |
| 7,491,214 B2 | 2/2009 | Greene, Jr. et al. |
| 7,601,165 B2 | 10/2009 | Stone |
| 7,682,400 B2 | 3/2010 | Zwirkoski |
| 7,819,898 B2 | 10/2010 | Stone et al. |
| 7,931,671 B2 | 4/2011 | Tenerz |
| 7,998,154 B2 | 8/2011 | Manzo |
| 8,177,809 B2 | 5/2012 | Mavani et al. |
| 8,206,416 B2 | 6/2012 | Mavani et al. |
| 8,221,451 B2 | 7/2012 | Mavani et al. |
| 8,377,094 B2 | 2/2013 | Mavani et al. |
| 2002/0026210 A1 | 2/2002 | Abdel-Gawwad |
| 2002/0058960 A1 | 5/2002 | Hudson et al. |
| 2002/0147457 A1 | 10/2002 | Rousseau |
| 2003/0100920 A1 | 5/2003 | Akin et al. |
| 2003/0220666 A1 | 11/2003 | Mirigian et al. |
| 2004/0034366 A1 | 2/2004 | van der Burg et al. |
| 2004/0044357 A1 | 3/2004 | Gannoe et al. |
| 2004/0044358 A1 | 3/2004 | Khosravi et al. |
| 2004/0044391 A1 | 3/2004 | Porter |
| 2004/0122456 A1 | 6/2004 | Saadat et al. |
| 2004/0186464 A1 | 9/2004 | Mamayek et al. |
| 2004/0199175 A1 | 10/2004 | Jaeger et al. |
| 2004/0225183 A1 | 11/2004 | Michlitsch et al. |
| 2004/0236344 A1 | 11/2004 | Monstadt et al. |
| 2004/0236348 A1 | 11/2004 | Diaz et al. |
| 2004/0237970 A1 | 12/2004 | Vournakis et al. |
| 2005/0033401 A1 | 2/2005 | Cunniffe et al. |
| 2005/0049626 A1 | 3/2005 | Bugard |
| 2005/0049628 A1 | 3/2005 | Schweikert et al. |
| 2005/0070759 A1 | 3/2005 | Armstrong |
| 2005/0090860 A1 | 4/2005 | Paprocki |
| 2005/0090861 A1 | 4/2005 | Porter |
| 2005/0113858 A1 | 5/2005 | Deutsch |
| 2005/0155608 A1 | 7/2005 | Pavcnik et al. |
| 2005/0159776 A1 | 7/2005 | Armstrong |
| 2005/0182495 A1 | 8/2005 | Perrone |
| 2005/0228448 A1 | 10/2005 | Li |
| 2005/0240216 A1 | 10/2005 | Jones et al. |
| 2005/0251200 A1 | 11/2005 | Porter |
| 2005/0267528 A1 | 12/2005 | Ginn et al. |
| 2005/0277981 A1 | 12/2005 | Maahs et al. |
| 2005/0283187 A1 | 12/2005 | Longson |
| 2006/0009797 A1 | 1/2006 | Armstrong |
| 2006/0036282 A1 | 2/2006 | Wahr et al. |
| 2006/0052822 A1 | 3/2006 | Mirizzi et al. |
| 2006/0058834 A1 | 3/2006 | Do et al. |
| 2006/0074447 A2 | 4/2006 | Armstrong |
| 2006/0079929 A1 | 4/2006 | Marks et al. |
| 2006/0122633 A1 | 6/2006 | To et al. |
| 2006/0142797 A1 | 6/2006 | Egnelov |
| 2006/0155303 A1 | 7/2006 | Konya et al. |
| 2006/0200192 A1 | 9/2006 | Fitz et al. |
| 2006/0206140 A1 | 9/2006 | Shaolian et al. |
| 2006/0206196 A1 | 9/2006 | Porter |
| 2006/0212055 A1 | 9/2006 | Karabey et al. |
| 2006/0241687 A1 | 10/2006 | Glaser et al. |
| 2006/0264698 A1 | 11/2006 | Kondonis et al. |
| 2006/0265001 A1 | 11/2006 | Marks et al. |
| 2006/0271099 A1 | 11/2006 | Marks et al. |
| 2006/0282112 A1 | 12/2006 | Griffin |
| 2007/0031508 A1 | 2/2007 | Armstrong et al. |
| 2007/0083226 A1 | 4/2007 | Buiser et al. |
| 2007/0088445 A1 | 4/2007 | Patel et al. |
| 2007/0129757 A1 | 6/2007 | Armstrong |
| 2007/0135842 A1 | 6/2007 | Van de Moer et al. |
| 2007/0142859 A1 | 6/2007 | Buiser et al. |
| 2007/0179507 A1 | 8/2007 | Shah |
| 2007/0179527 A1 | 8/2007 | Eskuri et al. |
| 2007/0185530 A1 | 8/2007 | Chin-Chen et al. |
| 2007/0198059 A1 | 8/2007 | Patel et al. |
| 2007/0233278 A1 | 10/2007 | Armstrong |
| 2007/0244502 A1 | 10/2007 | Deutsch |
| 2007/0276121 A1 | 11/2007 | Westergom et al. |
| 2008/0004657 A1 | 1/2008 | Obermiller et al. |
| 2008/0009781 A1 | 1/2008 | Anwar et al. |
| 2008/0015635 A1 | 1/2008 | Olsen et al. |
| 2008/0015636 A1 | 1/2008 | Olsen et al. |
| 2008/0027477 A1 | 1/2008 | Obermiller et al. |
| 2008/0039547 A1 | 2/2008 | Khatri et al. |
| 2008/0039548 A1 | 2/2008 | Zavatsky et al. |
| 2008/0051824 A1* | 2/2008 | Gertner ........................ 606/192 |
| 2008/0051831 A1 | 2/2008 | Deal et al. |
| 2008/0071310 A1 | 3/2008 | Hoffman et al. |
| 2008/0245374 A1 | 10/2008 | Agnew |
| 2009/0054927 A1 | 2/2009 | Agnew |
| 2009/0099647 A1 | 4/2009 | Glimsdale et al. |
| 2009/0281557 A1 | 11/2009 | Sander et al. |
| 2010/0076463 A1 | 3/2010 | Mavani et al. |
| 2010/0087854 A1 | 4/2010 | Stopek et al. |
| 2010/0185234 A1 | 7/2010 | Fortson et al. |
| 2011/0130769 A1 | 6/2011 | Boebel et al. |
| 2011/0282368 A1 | 11/2011 | Swayze et al. |
| 2012/0016412 A1 | 1/2012 | Mavani et al. |
| 2012/0035644 A1 | 2/2012 | Eskaros et al. |
| 2012/0116447 A1 | 5/2012 | Stanley et al. |
| 2012/0323271 A1 | 12/2012 | Obermiller et al. |
| 2013/0006283 A1 | 1/2013 | Carrison et al. |

FOREIGN PATENT DOCUMENTS

| | | |
|---|---|---|
| JP | 2008-543504 | 12/2008 |
| WO | 89/11301 | 11/1989 |
| WO | 00/74576 | 12/2000 |
| WO | 2004/112864 | 12/2004 |
| WO | 2005/070302 | 8/2005 |
| WO | 2006/119256 | 11/2006 |
| WO | 2006/130213 | 12/2006 |
| WO | 2007/002260 | 1/2007 |
| WO | 2008/112740 | 9/2008 |
| WO | 2009/124144 | 4/2009 |
| WO | 2009/124148 | 4/2009 |
| WO | 2009/146369 A1 | 12/2009 |
| WO | 2010/028300 | 3/2010 |
| WO | 2012/050836 | 4/2012 |
| WO | 2012-050836 | 4/2012 |
| WO | 2012/174468 A1 | 12/2012 |
| WO | 2012/174469 A2 | 12/2012 |

OTHER PUBLICATIONS

Written Opinion, in connection with International Patent application No. PCT/US2012/042805, Nov. 28, 2012, (pp. 1-6).

(56) References Cited

OTHER PUBLICATIONS

Patent Examination Report No. 1 issued by the Australian Patent Office for Austrian Patent Application No. 2009289474, (Dec. 11, 2014) pp. 1-5.
First Examination Report issued by the Canadian Patent Office for Patent Application No. 2,720,206, (May 19, 2015) pp. 1-4.
Supplementary European Search Report issued by the European Patent Office for Application No. 12801043.6, (Jan. 15, 2015) pp. 1-7.
Extended European Search Report issued by the European Patent Office for Application No. 12800217.7, (Mar. 24, 2015) pp. 1-6.
International Search Report Issued by WIPO for PCT Application Serial No. PCT/US14/043261, (Dec. 23, 2014) pp. 1-4.
Written Opinion of the International Searching Authority issued by WIPO for PCT Application Serial No. PCT/US14/043261, (Dec. 23, 2014) pp. 1-6.
Patent Examination Report No. 1, Australian Patent Application No. 2009289474 issued on related matter (Dec. 11, 2014) pp. 1-5.
First Examination Report, Canadian Patent Application No. 2,720,206, issued on related matter, (May 19, 2015) pp. 1-4.
Supplementary European Search Report issued by the European Patent Office for Application No. 12801043.6, issued on related matter, (Jan. 15, 2015) pp. 1-7.
European Search Report issued by the European Patent Office for Application No. 09728360.0, issued on related matter (Apr. 4, 2011) pp. 1-5.
Extended European Search Report, European Patent Application No. 12800217.7, issued on related matter, (Mar. 24, 2015) pp. 1-6.
Partial Search Report, issued by the European Searching Authority for Application No. PCT/US2014/011663, issued on related matter, (May 9, 2014) pp. 1-3.
International Search Report, PCT Application No. PCT/US2012/042805, issued on related matter, (Nov. 28, 2012) pp. 1-5.
International Search Report, PCT Application Serial No. PCT/US14/043261, issued on related matter, (Dec. 23, 2014) pp. 1-4.
International Search Report, PCT Application Serial No. PCT/US14/043280, issued on related matter, (Nov. 17, 2014) pp. 1-7.
Written Opinion, PCT Patent Application No. PCT/US2012/042805, issued on related mater, (Nov. 28, 2012) pp. 1-6.
Written Opinion of the International Searching Authority, PCT Application Serial No. PCT/US14/043261, issued on related matter, (Dec. 23, 2014) pp. 1-6.
Written Opinion of the International Searching Authority, PCT Application Serial No. PCT/US14/043280, issued on related matter, (Nov. 17, 2014) pp. 1-9.
Champagne, et al., "Efficacy of Anal Fistula Plug in Closure of Cryptoglandular Fistulas: Long-Term Follow-Up", Diseases of the Colon & Rectum, Dis. Colon Rectum 2006; vol. 49, No. 12, pp. 1817-1821. (5 pages).

Draus, et al., "Enterocutaneous fistula: Are treatments improving?", Surgery, vol. 140, No. 4, Oct. 2006, pp. 570-578. (9 pages).
Farsi, et al., "A New Conservative Approach in the Treatment of Postoperative Digestive-Tract Fistulas. Mechanical Closure by a Balloon-Catheter", Minerva Chir, Feb. 2001; 56(1):31-9, article in Italian. (1 page translation).
Hollington, et al., "An 11-year Experience of Enterocutaneous Fistula", British Journal of Surgery 2004; 91: pp. 1646-1651. (6 pages).
Hyman, "Anorectal Abscess and Fistula", Primary Care: Clinics in Office Practice, vol. 26, Issue 1, Mar. 1999, pp. 69-80. (13 pages).
Jenkins, et al., "Single Operator Deployment of Vasoseal ES ®: The Experience of Skaggs Community Health Center", Sep. 1, 2004. (2 pages).
Lomis, et al., "Refractory Abdominal-Cutaneous Fistulas or Leaks: Percutaneous Management with a Collagen Plug", Journal of the American College of Surgeons, vol. 190, No. 5, May 2000, pp. 588-592. (5 pages).
Mclean, et al., "Enterocutaneous Fistulae: Interventional Radiologic Management," AJR 138:615-619, Apr. 1982. (5 pages).
Medeiros, et al., "Treatment of Postoperative Enterocutaneous Fistulas by High-Pressure Vacuum with a Normal Oral Diet", Digestive Surgery, 2004; 21, pp. 401-405. (5 pages).
O'Connor, et al., "Efficacy of Anal Fistula Plug in Closure of Crohn's Anorectal Fistulas," Diseases of the Colon & Rectum, Dis Colon Rectum, Oct. 2006, vol. 49: pp. 1569-1573. (5 pages).
Paul, et al., "Bronchopleural Fistula Repair During Clagett Closure Utilizing a Collagen Matrix Plug", Ann. Thorac. Surg. 2007, 83, pp. 1519-1521. (3 pages).
Sutra, "Fistula in Ano", Way2Ayurveda, www.way2ayurveda.com/fistulainano/index.html, printed Mar. 20, 2008. (3 pages).
Unknown Author, *Controlled Deployment for Confident Closure*, St. Jude.Medical (2009) pp. 1-3.
Unknown Author, *Datascope's Vasoseal Seen As Cost Effective Aid To Coronary Patients*, Gale, Cengage Learning (2008) pp. 1-3.
Unknown Author, *Practice Parameters for Treatment of Fistula-in-Ano*, The American Society of Colon and Rectal Surgeons, ASCRS Standards Practice Task Force, Dis Colon Rectum (Dec. 1996) pp. 1361-1362. (2 pages).
Von Koperen, et al., "Anal Fistula Plug for Closure of Difficult Anorectal.Fistula: A Prospective Study," Dis Colon Rectum 2007; 50, pp. 1-5. (5 pages).
Wexner, et al., "Practice Parameters for Treatment of Fistula—in—Ano-Supporting Documentation", Dis Colon Rectum, Dec. 1996, pp. 1363-1372. (10 pages).
Zagrodnik II, "Fistula-in-Ano", General Surgery—Colorectal, Mar. 12,.2007. (16 pages).

\* cited by examiner

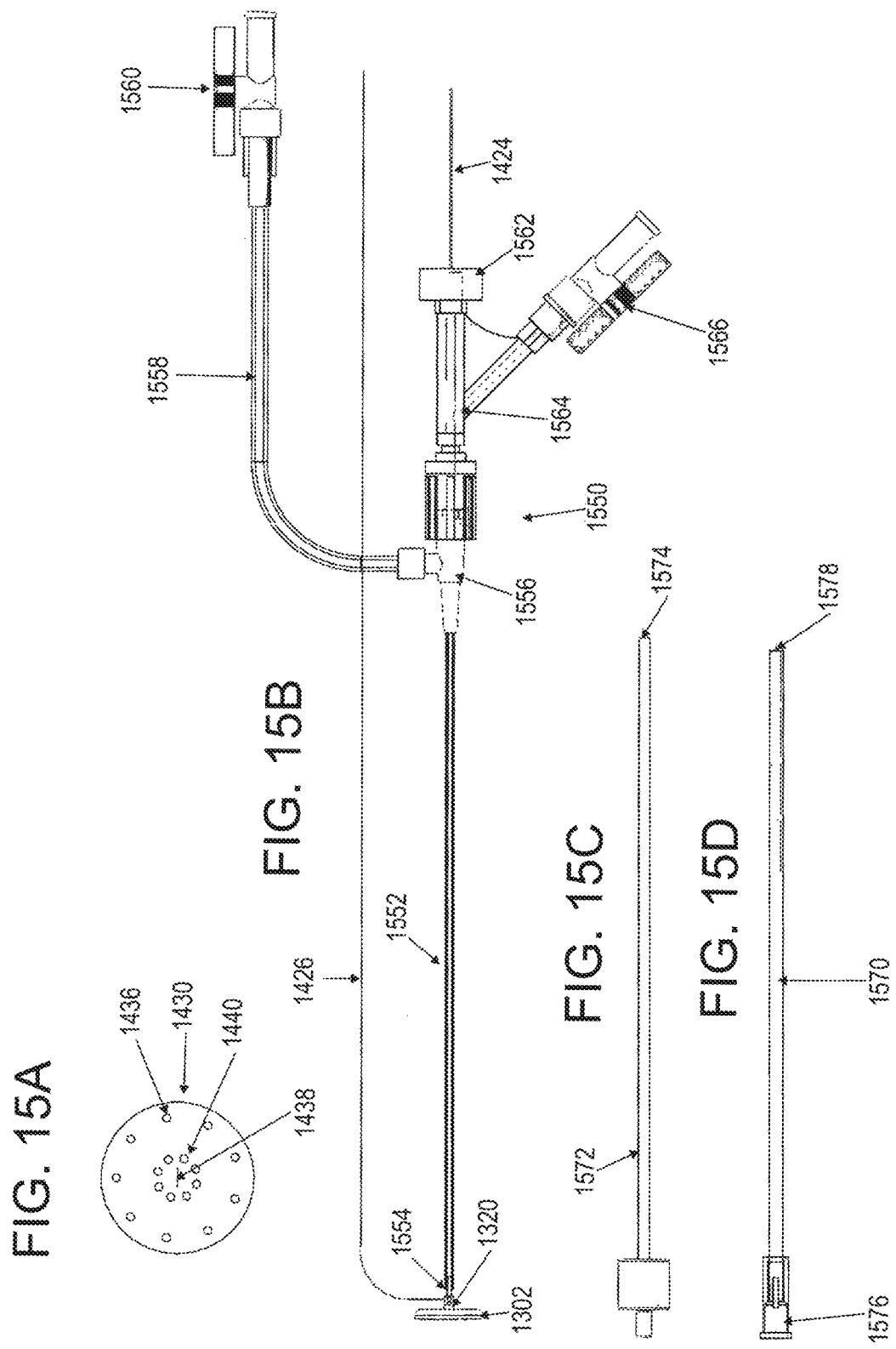

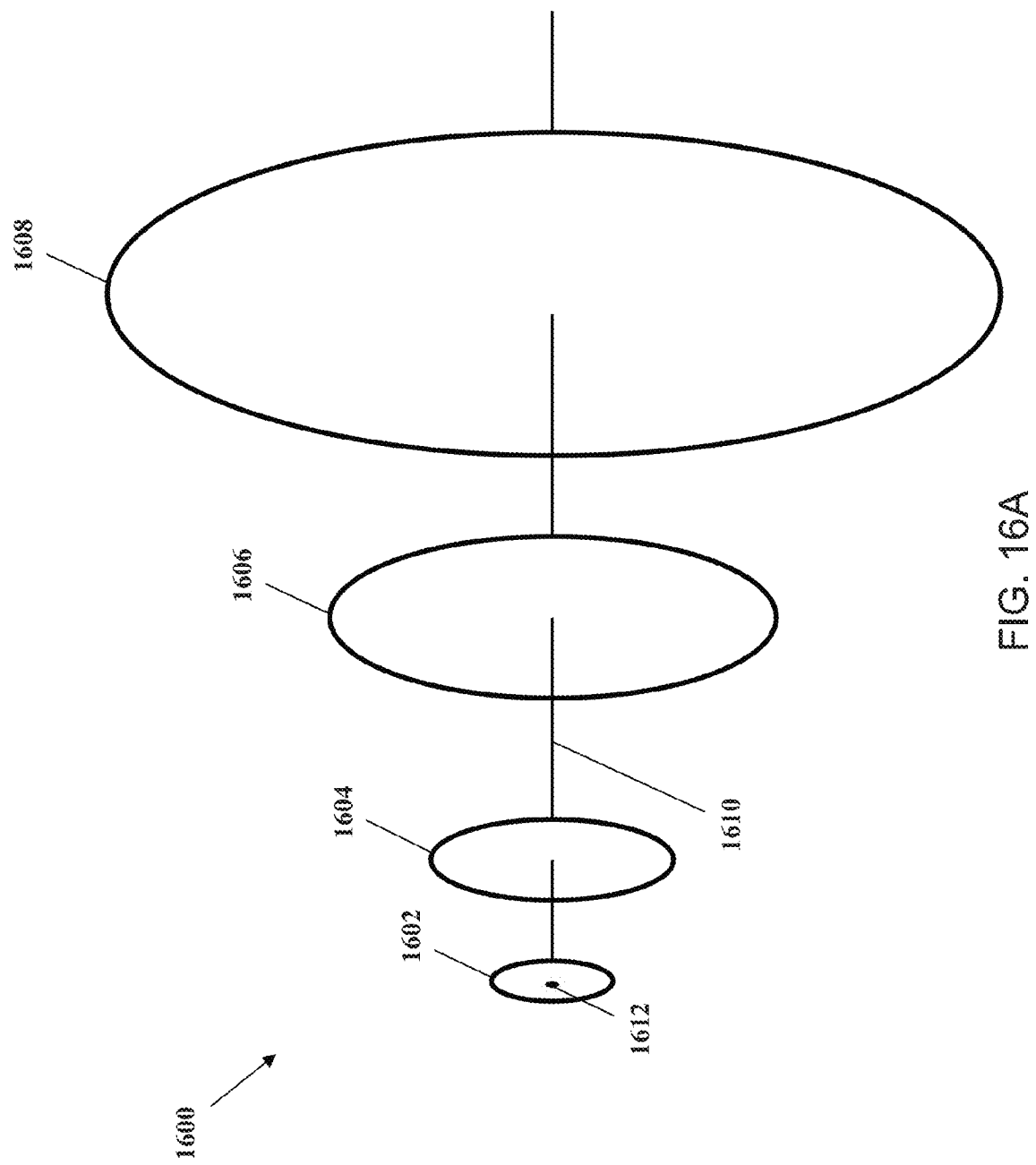

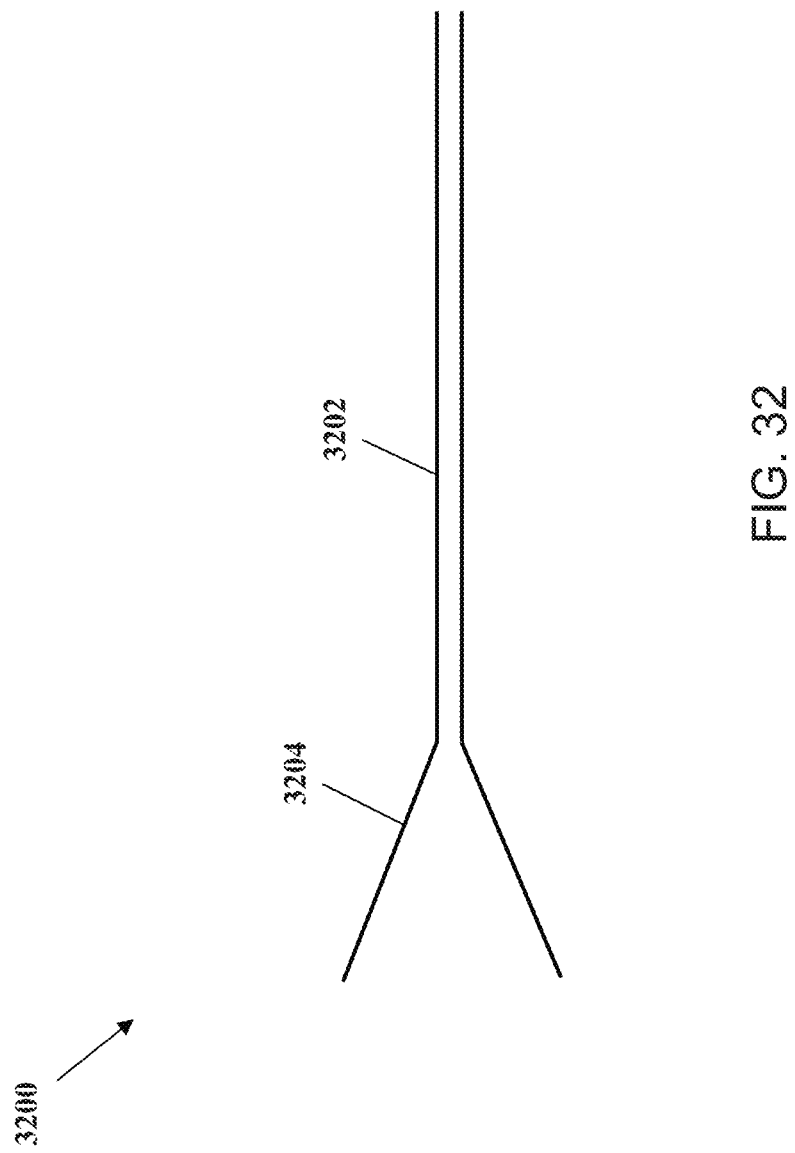

FISTULA TREATMENT DEVICES AND RELATED METHODS

CROSS-REFERENCE TO RELATED APPLICATIONS

This application claims priority under 35 U.S.C. §119(e) to U.S. Provisional Ser. No. 61/497,899, filed Jun. 16, 2011, and U.S. Provisional Ser. No. 61/498,495, filed Jun. 17, 2011, which are hereby incorporated by reference in their entireties.

TECHNICAL FIELD

The present invention relates to medical apparatus and methods. More specifically, the present invention relates to implantable devices for closing fistulas and methods of using such devices.

BACKGROUND

Fistulas are a major cause of morbidity and mortality, as there are over one hundred thousand cases of pathologic fistulas a year, which account for over ten thousand deaths. They cost the healthcare system billions of dollars each year to treat.

Fistulas are tissue-lined connections between body cavities and hollow organs or between such cavities or organs and the surface of the body. The fistula tract includes a void or potential void in the soft tissues extending from a primary fistula opening to a blind ending or leading to one or more secondary fistula openings, sometimes following along tissue planes of organs or between organs. Fistulas frequently develop as a consequence of infections or accompany abscess formations. Although some fistulas are purposely created for therapeutic purposes such as tracheostomy tracts, gastric feeding tube tracts, or arteriovenous fistulas for dialysis access, pathological fistulas are abnormal tracts that typically occur either congenitally or form after surgery, surgery-related complications, or trauma. They are most often open tracts that have epithelialized, endothelialized, or mucosalized.

Fistulas can form between almost any two-organ systems, or multiple organs between different sites of the same organ. For example, they may occur between internal organs and skin (enterocutaneous fistulas, gastrocutaneous fistulas, anal fistulas, rectovaginal fistulas, colocutaneous fistulas, vesiclocutaneous fistulas, intestinocutaneous fistulas, tracheocutaneous fistulas, bronchocutaneous fistulas, etc.) or between internal organs themselves (tracheal-esophageal fistulas, gastrointestinal fistulas, colovesicular fistulas, palatal fistulas, etc.). Fistulas may also form between blood vessels such as arteriovenous fistulas.

Although fistulas may form in many locations in the body, they are almost universally highly morbid to patients and difficult for clinicians to treat. For example, enterocutaneous fistulas are one of the most feared complications of abdominal surgery. Enterocutaneous fistulas are abnormal connections that form between the bowel and skin and can occur after abdominal surgery, after trauma, or as a complication of Crohn's disease. Some reports estimate that enterocutaneous fistulas may form in as many as 1% of patients that undergo major abdominal surgery. They often require months of supportive care and/or major abdominal surgery. The overall mortality rate for patients that develop enterocutaneous fistulas remains high at around 20%.

Current options for treatment of enterocutaneous fistulas include long-term conservative management or major surgery. In a first option, the patients are placed on restricted enteric intake and managed with parenteral nutritional support. The fistula leakage is controlled using a stoma bag. If the fistula output is high, drains are sometimes placed to try and control the fistula output. Spontaneous closure is relatively low at around 25%. If fistulas fail to spontaneously close with current management after 5 weeks of bowel rest, then many surgeons advocate surgical treatment at this point, though supportive care could continue indefinitely. Patients with open fistula tracts often have ongoing associated malnutrition and electrolyte imbalance issues as well as chronic non-healing abdominal wounds.

A second option is a major surgery, which has a mortality rate near 30%. The surgery involves resection of the diseased intestinal segment, extirpation of the fistula, and debridement of the fistulous tract through the abdominal wall and subcutaneous tissue. This major abdominal surgery often requires blood transfusion and post-operative ICU admissions. As a result of chronic inflammation and having abdomens that have been previously operated on, these patients typically form dense adhesions and have highly friable tissues. In addition, these patients can be severely malnourished. These conditions make operations on enterocutaneous fistulas extremely difficult and dangerous. After the surgery the patient is put on total parenteral nutrition ("TPN") for several more days before the patient can be weaned off TPN and slowly introduced to normal foods.

Other treatment options may include implantable devices designed to aid in the closure of the fistula. These devices, however, may cause adverse immunological reactions in patients, may allow leakage of fluid around them, or may migrate or become dislodged when the patient exerts himself, such as during exercise. There is a need in the art for an implantable device for closing a fistula that reduces the chance of adverse immunological reactions, and the leakage of fluid through the fistula tract, and that has a reduced chance of migration or dislodgement during use.

SUMMARY

Disclosed herein are implantable fistula closure devices and related kits and methods. In some embodiments, a distal anchor for an implantable fistula treatment device may comprise a suture, and a plurality of foldable members including at least a distal-most foldable member and a proximal-most foldable member, wherein the distal-most foldable member comprises a suture attachment structure, wherein the proximal-most foldable member is configured to couple to a surface of a body lumen at a distal opening of a fistula, wherein the proximal-most foldable member is configured to occlude the fistula at the distal opening, wherein the proximal-most foldable member is configured to slide along the suture attached to the suture attachment structure, wherein the proximal-most foldable member comprises a proximal first average dimension substantially parallel to a longitudinal axis of the suture, a proximal second average dimension orthogonal to the proximal first average dimension, and a proximal third average dimension orthogonal to the proximal first and second average dimensions, the proximal first average dimension being no greater than 10% of the greater of the proximal second and third average dimensions, and wherein the distal-most foldable member comprises a distal first average dimension substantially parallel to the longitudinal axis of the suture, a distal second average dimension orthogonal to the distal first average dimension, and a distal third average dimension orthogonal to the distal first and second average dimensions, the distal first average dimension being no greater than 30% of the greater of the distal second and third average dimensions. The distal anchor may comprise at least one additional foldable member positioned between the distal-most foldable member and the proximal-most foldable member. The proximal second average dimension of the proximal-most foldable member of the distal anchor may be larger than the distal second average dimension of the distal-most foldable member. The distal second average dimension of the distal-most foldable member of the distal anchor may have less than or equal to 20% of the proximal second average dimension of the proximal-most foldable member.

The proximal-most foldable member of the distal anchor may comprise a generally circular perimeter. The proximal-most foldable member of the distal anchor may comprise a generally concave shape. The distal-most foldable member of the distal anchor may comprise a generally concave shape, and a radius of curvature of the distal-most foldable member may be smaller than a radius of curvature of the proximal-most member.

The distal anchor may comprise coupling members on opposing surfaces of at least two of the plurality of foldable members. The coupling members of the distal anchor may comprise complementary protrusions or recesses on the surfaces of the members. The complementary protrusions of the distal anchor may comprise teeth. The coupling member of at least one foldable member of the distal anchor may comprise a curing agent. The coupling member of the at least one foldable member of the distal anchor may comprise a capsule enclosing the curing agent. The capsules of the distal anchor may be configured to rupture upon contact with another foldable member. The coupling members of at least two foldable members of the foldable members may be configured to produce attracting electromagnetic forces.

Each of the foldable members may decrease in flexibility from the proximal-most to the distal-most foldable member. The proximal first average dimension of the proximal-most foldable member may be less than the distal first average dimension of the distal-most foldable member. A density of the proximal-most foldable member of the distal anchor may be less than a density of the distal-most foldable member.

A proximal surface of the proximal-most foldable member of the distal anchor may comprise a grapple configured to attach the proximal-most foldable member to a surface of the body lumen. A distal surface of the proximal-most foldable member of the distal anchor may comprise a grapple activation structure configured to activate the grapple upon contact with the proximal surface of another foldable member. The grapple activation structure of the distal anchor may comprises a protrusion.

At least one of the plurality of foldable members of the distal anchor may include a protrusion configured to resist relative movement between at least two of the plurality of foldable members. At least one other of the plurality of foldable members of the distal anchor may include a recess configured to receive the protrusion. At least one of the plurality of foldable members of the distal anchor may comprise at least two protrusions configured to resist relative movement between the at least two of the plurality of foldable members.

The distal-most foldable member of the distal anchor may be pre-attached to the suture at the suture attachment mechanism. The proximal-most foldable member may not be pre-attached to the suture.

In some embodiments, a method of sealing a fistula tract may comprise positioning a first sealing member adjacent a distal opening of a fistula tract at a location outside of the fistula tract and positioning a second sealing member against the first sealing member at a location outside of the fistula tract, wherein at least one dimension of the second sealing member is larger than the first sealing member. The method of sealing a fistula tract may also comprise passing the first sealing member through the fistula tract before positioning the first sealing member at the location outside of the fistula tract. Positioning a second sealing member in the method of sealing a fistula tract may comprise positioning an interfit structure of the second sealing member against a complementary interfit structure of the first sealing member. The method of sealing a fistula tract may comprise positioning a third sealing member against the second sealing member at a location outside of the fistula tract, wherein at least one dimension of the third sealing member is larger than the second sealing member. The method of sealing a fistula tract may comprise positioning a porous body within the fistula tract after positioning the second sealing member against the first sealing member. The method of sealing a fistula tract may comprise tensioning a tether member attached to the first sealing member to deform an aggregate distal anchor comprising the first and second sealing members toward the distal fistula tract. The method of sealing a fistula tract may comprise sealing the aggregate distal anchor at an outer edge seal and an inner seal that is spaced apart from the outer edge seal. The method of sealing a fistula tract may comprise securing the tether to maintain the tensioning of the tether member. Securing the tether in the method of sealing a fistula tract may comprise securing the tether to a resilient structure.

In some embodiments, a fistula irrigation catheter may comprise a tubular member, where the tubular member may comprise a proximal end, a distal end and a wall portion therebetween, the wall portion having a plurality of apertures therethrough, wherein the distalmost aperture of the plurality of apertures is located at least about 2 centimeters from the distal end of the tubular member, and wherein the plurality of apertures are oriented to provide non-orthogonal irrigation therethrough. The plurality of apertures of the fistula irrigation catheter may be configured to provide bidirectional irrigation. The fistula irrigation catheter may also comprise a brushing member configured to brush a fistula tract.

In some embodiments, a method of irrigating a fistula tract comprises inserting an irrigation catheter into the fistula tract, grasping both a proximal end of the irrigation catheter and a distal end of the irrigation catheter, and moving the irrigation catheter proximally and distally within the fistula tract to irrigate different portions of the fistula tract. The irrigation catheter of the method of irrigating a fistula tract may comprise a brushing member, and the method may comprise brushing the fistula tract.

While multiple embodiments are disclosed, still other embodiments fistula treatment devices, kits and methods will become apparent to those skilled in the art from the following Detailed Description. As will be realized, the devices, kits and methods are capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 15A is a superior view of the proximal retaining structure in FIG. 14; FIG. 15B is a schematic side elevational view of an embodiment of a delivery instrument for the device depicted in FIG. 14; FIGS. 15C and 15D are examples of an expandable member actuator and delivery catheter, respectively.

FIGS. 16A and 16B depict an exemplary embodiment of a distal anchor comprising multiple discs in a separated and a collapsed configuration, respectively.

FIG. 32 is a schematic cross-sectional view of a loading device for a fistula treatment device.

DETAILED DESCRIPTION

Figure 1A:
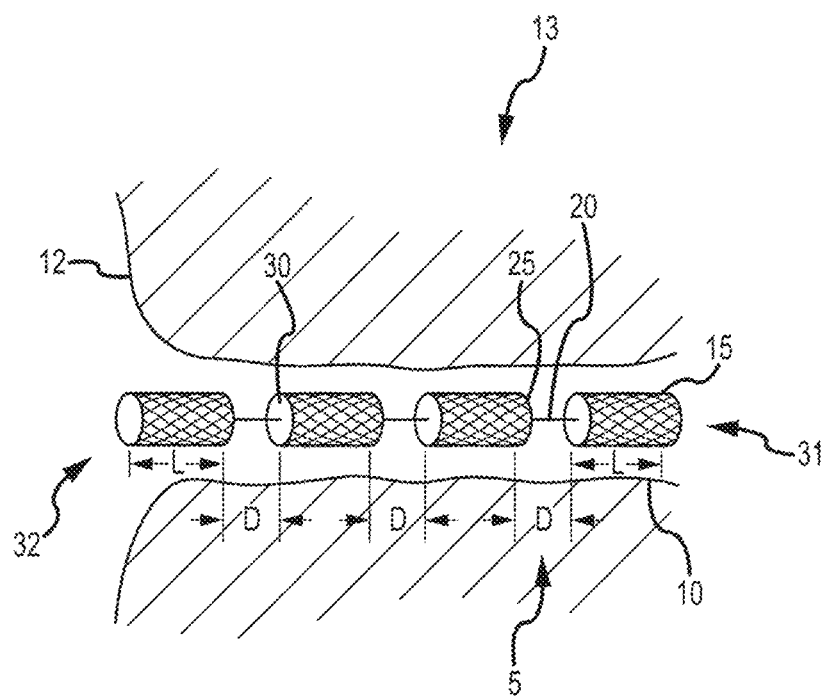
FIG. 1A is an isometric view of an embodiment of an implantable fistula closure device having a segmented body and located in a fistula tract in a compressed or non-expanded state.

Fistula tracts 10 can be nonlinear or curvilinear and contain cavities of varying sizes at different intervals within the tract. Fistulas may also comprise multiple interconnected passages.

An implantable fistula closure device 5 disclosed herein employs advantageous design, configuration techniques and attributes to accommodate such constraints.

For example, and referring to FIGS. 1A-1D, in some embodiments, the device 5 may have a segmented expandable body 13 formed of a plurality of individual expandable bodies or members 15 that are coupled together. The members 15 may be coupled together in an immediately adjacent abutting fashion or in a spaced-apart fashion (as shown). Upon insertion of the device 5 into the fistula tract 10 with the expandable members 15 in a collapsed or compressed state, the expandable members 15 are allowed to expand to fill the portion of the fistula tract 10 in which each expandable member 15 is located. It should be noted that the collapsed or compressed state allows for convenient insertion of the device 5 into the fistula tract 10. Additionally, the segmented nature of the body 13 of the device 5 or, more specifically, the fact that the device's body 13 is formed of a plurality of individual members 15, allows the body 13 to be more easily placed in, and to more readily conform to, the tortuous and diametrically varying configuration of a fistula tract 10 when expanded within the fistula tract. Thus, once the body 13 is allowed to expand within the fistula tract, the device generally completely fills the fistula tract.

In certain embodiments, when the body 13 expands to fill the fistula tract, the device may generally stop, resist or slow fluid flow from the bowel from running out through the fistula tract. The device may do this by occluding the distal end of the tract via a distal end of the device body 13 that is generally non-porous or has an ability to seal the distal end of the tract. However, generally speaking, a fistula tract will leak fluid from within the tissue walls surrounding the fistula tract. Some of this fluid will be absorbed by the device. The remaining fluid will drain out of the proximal end of the tract, potentially through the proximal end of the device body 13, which is generally porous or has the ability to allow the passage of fluids while generally occluding or filling the tract.

The time to closure and the necessity for surgery may be reduced (e.g., significantly) by preventing or reducing bodily fluids that originate at the distal end of the tract (e.g., bowel fluids) from passing through a fistula tract 10 and, in some embodiments, also by reducing the amount or rate of flow through the fistula tract for body fluids originating in the tract itself. In certain embodiments, the devices 5 disclosed herein may reduce or eliminate the passage of fluids through the tract 10 while also providing a matrix that promotes tissue growth. The devices 5 may be utilized to treat a variety of clinically significant fistulas 10, as appropriate, including enterocutaneous fistulas, anal fistulas, bronchopleural fistulas, non-healing g-tube tracts, tracheal-esophageal fistulas, and others.

Referring again to FIGS. 1A and 1B, the device 5 is depicted as located in a fistula tract 10 in a compressed or non-expanded state (FIG. 1A) and in a non-compressed or expanded state (FIG. 1B). The device 5 includes a proximal end 31, a distal end 32, and the expandable body 13, which is formed of a plurality of individual porous bodies 15 operably connected via a connecting member 20. Each porous body 15 includes a proximal end 25 and a distal end 30. Additionally, each porous body 15 is adapted to expand from a compressed or non-expanded state (FIG. 1A) to a non-compressed or expanded state (FIG. 1B) after insertion into the tract 10, thereby filling any cavities within the tract 10 and approximating the fistula tract walls.

As can be understood from FIG. 1A, in some embodiments, when the bodies 15 are in a compressed or non-expanded state, the bodies 15 will be spaced apart from each other along the length of the device 5, thereby forming a segmented configuration for the device body 13. In some embodiments, the spaced-apart distances D between adjacent proximal and distal ends 25, 30 of the bodies 15 in a compressed or non-expanded state is between approximately zero mm and approximately five mm. In one embodiment, the spaced-apart distances D between adjacent proximal and distal ends 25, 30 of the bodies 15 in a compressed or non-expanded state are between approximately zero mm and approximately 25 mm. Where the distance D between immediately adjacent bodies 15 is approximately zero mm when the bodies 15 are in a non-expanded state, the bodies 15 will be said to be in an abutting or touching configuration, as opposed to a spaced-apart condition. Regardless, the device body 13 will still be considered to be segmented on account of the device body 13 being formed of a plurality of individual porous bodies 15.

In some embodiments, the spaced-apart distances D between adjacent proximal and distal ends 25, 30 of the bodies 15 in a compressed or non-expanded state are between approximately zero percent and approximately two and one-half percent of the overall non-expanded length L of a body 15. Where the distance D between immediately adjacent bodies 15 is approximately zero percent of the length L of a body 15 when the bodies 15 are in a non-expanded state, the bodies 15 will be said to be in an abutting or touching configuration, as opposed to a spaced-apart condition. The device body 13 will still be considered to be segmented, however, on account of the device body 13 being formed of a plurality of individual porous bodies 15.

Regardless of whether the bodies are in a spaced-apart configuration or an abutting or touching configuration when the bodies 15 are in the compressed state, the segmented configuration of the device body 13 facilitates the device body 13 being inserted in and conforming to the tortuous diametrically varied route formed by the tract 10.

Figure 1B:
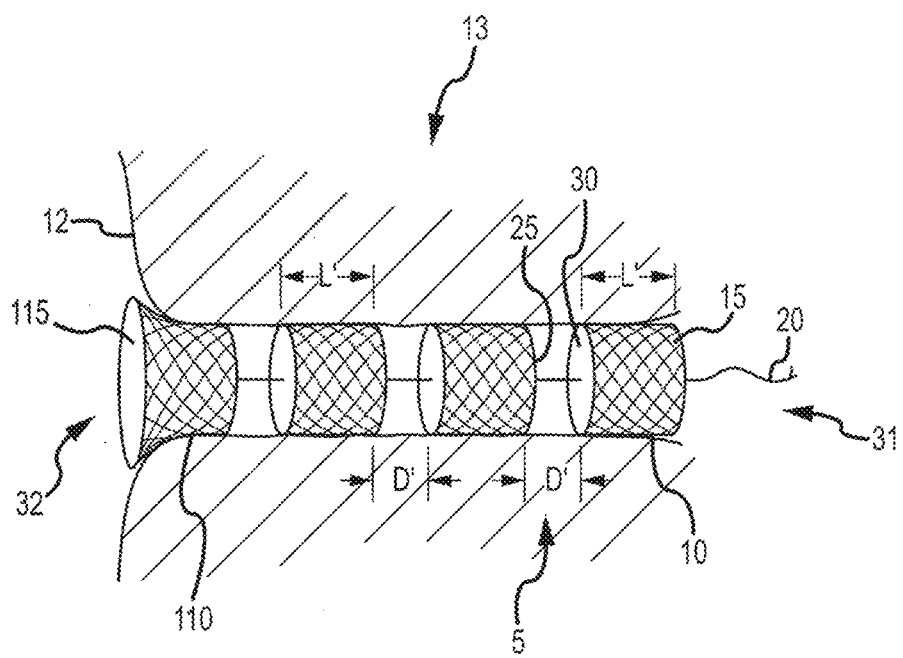
FIG. 1B is the same view as FIG. 1A, except the implantable fistula closure device is in a non-compressed or expanded state within the fistula tract.

As can be understood from FIG. 1B, when the bodies 15 are fully expanded within the tract 10, the spaced-apart distances D' between adjacent proximal and distal ends 25, 30 of the bodies 15 in a non-compressed or expanded state may be between approximately zero mm and approximately five mm. In some embodiments, the spaced-apart distances D' between adjacent proximal and distal ends 25, 30 of the bodies 15 in a non-compressed or expanded state may be between approximately zero percent and approximately two and one-half percent of the overall expanded length L' of a body 15. The expansion of the bodies 15 after insertion into the fistula tract 10 allows the device body 13 to approximate the walls of the fistula tract, as well as fill open cavities. Because the segmented configuration of the device body 13 allows the device to closely conform to the tortuous and diametrically varied route formed by the tract 10, the bodies 15, when in an expanded state within the tract 10, generally fill the tract 10 in a manner that minimizes voids and dead space. Minimizing voids and dead space lowers the chance of sepsis and other complications.

While a segmented body 13 has been described, some embodiments of tissue treatment devices may comprise a non-segmented body (i.e., a body 13 that is a continuous, single-piece body 13 as opposed to being formed from multiple bodies 15).

Any suitable methods may be used to deliver or deploy the fistula treatment devices described herein.

In one embodiment, and as illustrated in FIGS. 10A-10F, the device 5 may be loaded in a lumen of a catheter, sheath or guidewire. As can be understood from FIGS. 10A and 10B, the loaded catheter or sheath 900 or guidewire (not shown) is then inserted into the tract 10. Next, and as shown in FIG.

Figure 10A:
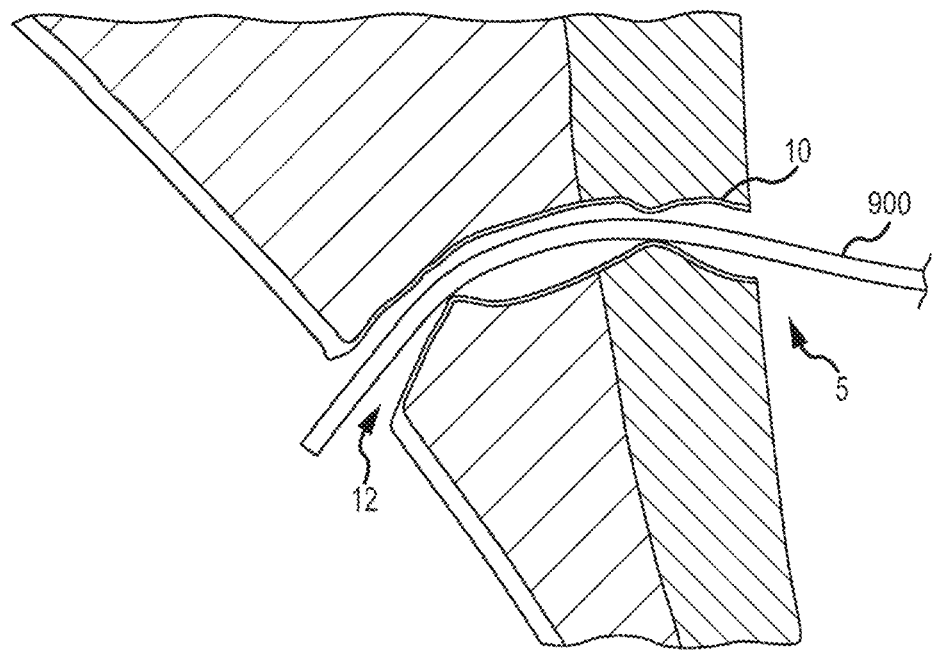
FIGS. 10A-10F are isometric views of a fistula closure device illustrating one embodiment of a method of treating a fistula.
Figure 10B:
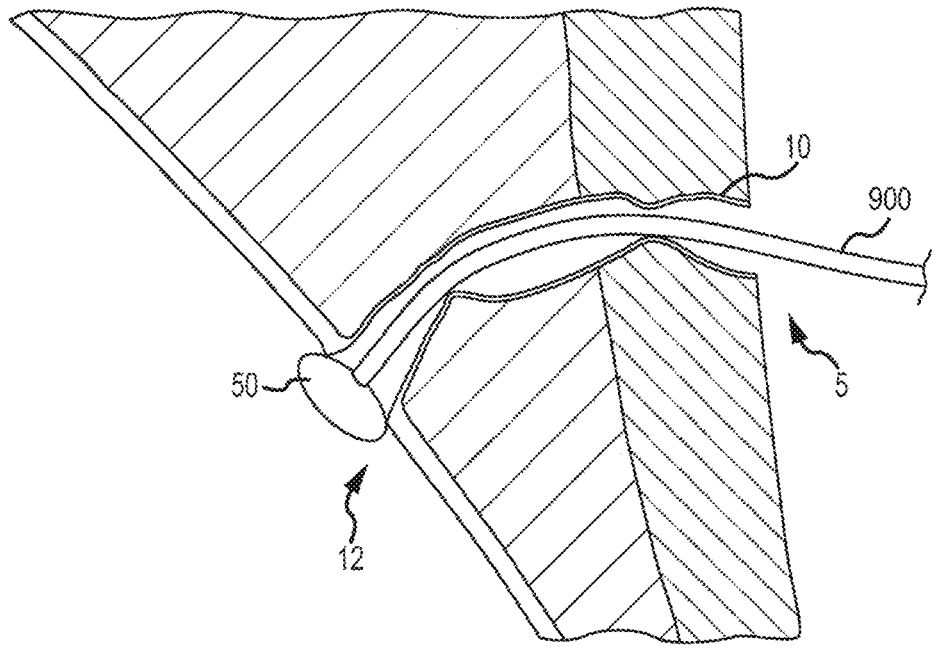
Figure 10C:
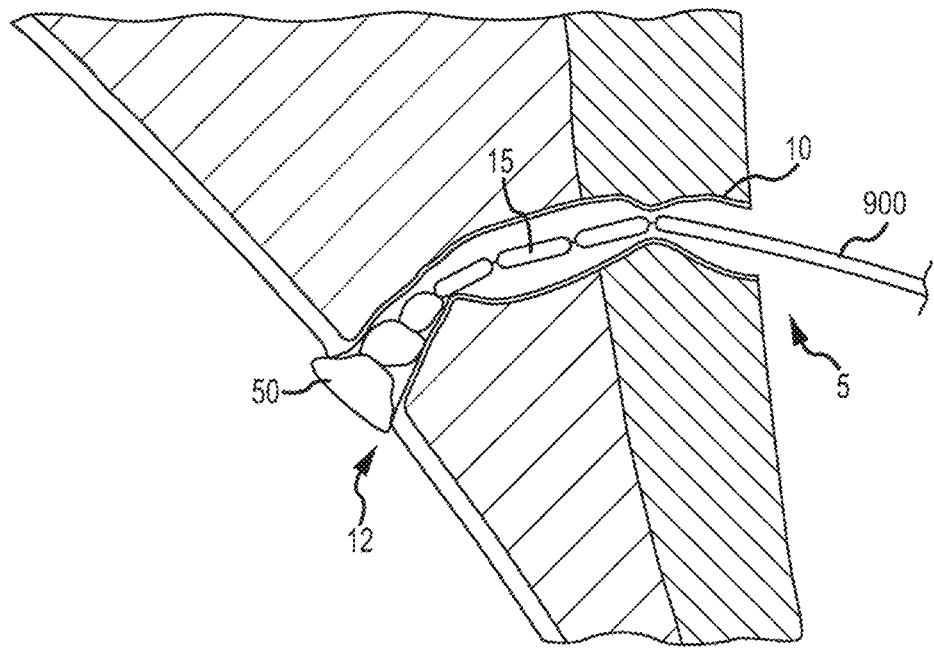
Figure 10D:
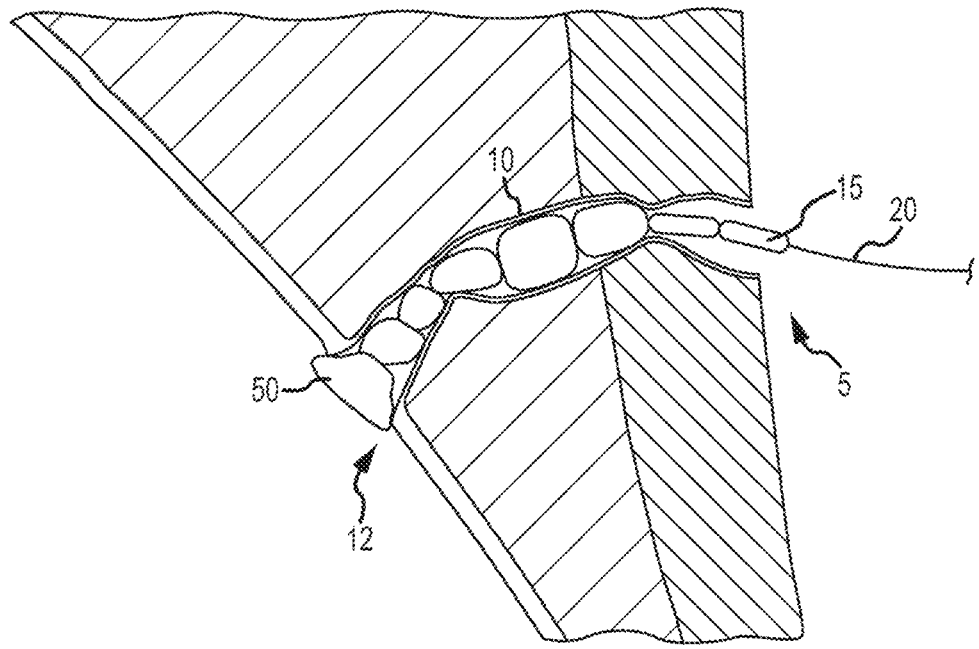
Figure 10E:
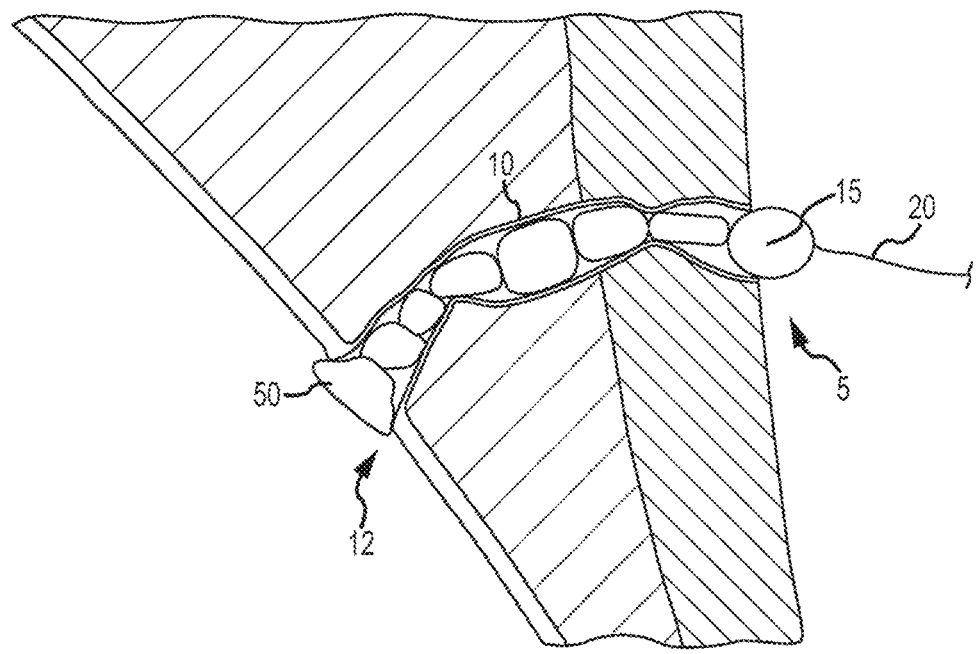
Figure 10F:
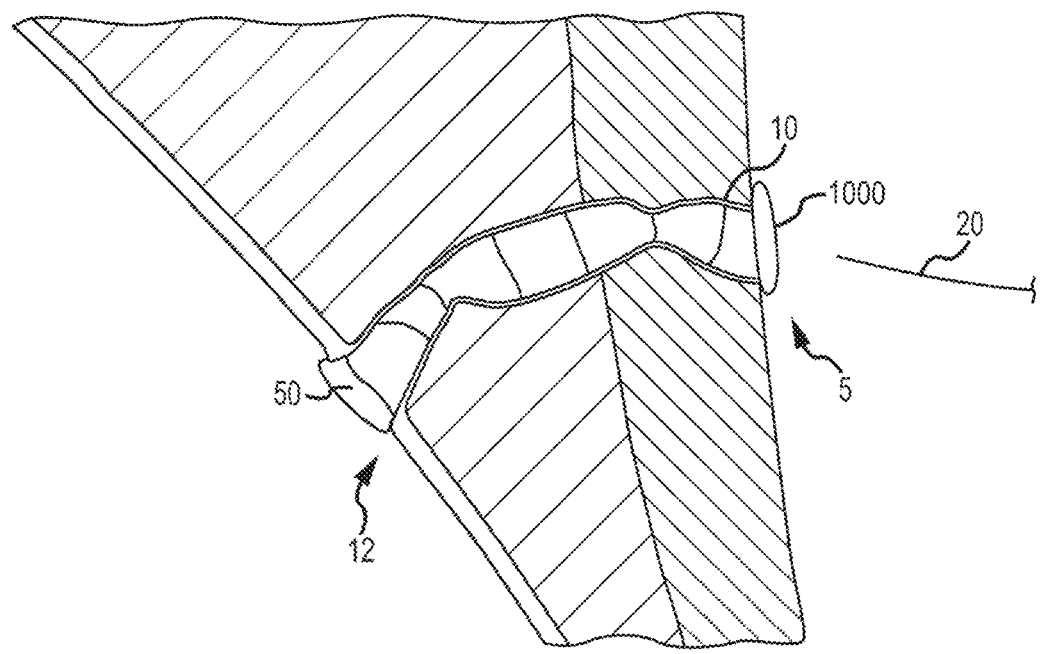

10C, the loaded catheter or sheath 900 or guidewire is withdrawn from about the device body 13 to leave the device body 13 within the tract 10. As indicated in FIGS. 10C-10F, the device body 13 then softens and/or expands to fill and occlude the tract 10. As illustrated in FIG. 10F, a proximal clip 1000 may be used at the proximal end of the device 5 to further secure the device 5 in the tract 10. Other proximal members may alternatively or additionally be used, as appropriate, and as discussed in more detail below.

Figure 9A:
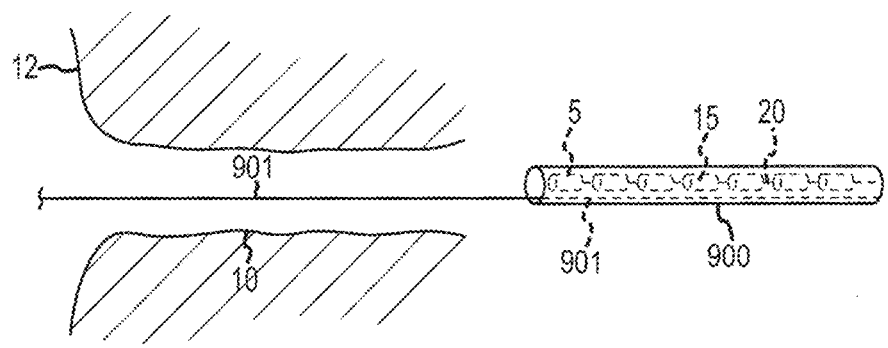
FIG. 9A is a side view of an embodiment of a delivery device for an implantable fistula closure device, where a portion of the delivery device is inserted into a fistula tract.
Figure 9B:
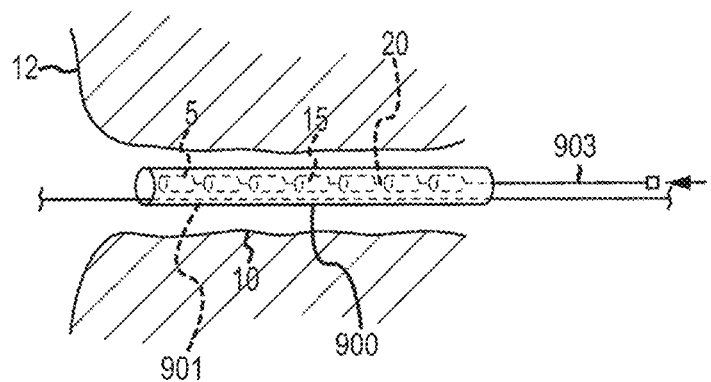
FIG. 9B is the same view as FIG. 9A, except the entire delivery device is shown inserted into the fistula tract.
Figure 9C:
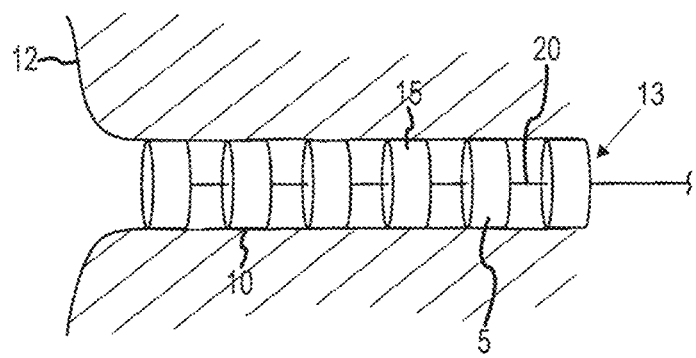
FIG. 9C is the same view as FIG. 9A, except the delivery device is withdrawn from about the device body and the device body is fully expanded.

In another embodiment, and as shown in FIGS. 9A-9C, the catheter or sheath may be a dual lumen catheter 900, where one lumen contains the device 5 and the other lumen contains a guidewire 901. In certain embodiments, the catheter may be a multi-lumen catheter where at least one lumen is shaped like a "D". In some embodiments, a delivery device may include a central or main lumen through which the fistula closure device 5 may pass and a secondary lumen through which the guidewire 901 may pass. As can be understood from FIGS. 9A and 9B, the guidewire 901 is inserted into the fistula tract 10 and the catheter 900 is tracked over the guidewire 901. As shown in FIG. 9C, the device 5 is deployed and the catheter 900 is withdrawn from about the device body 13 to leave the device body within the tract 10. The device body 13 then expands to fill and occlude the tract 10.

In some embodiments, a catheter comprising a peel-away sheath may be used. For example, a skive, score, partial cut, mechanical joint or formed groove may create a longitudinally extending stress concentration for causing the catheter to peel along the stress concentration.

In certain embodiments, the delivery device 900 may be tracked over a guidewire 901 with the fistula occlusion device 5 residing in the main lumen. Once properly positioned in the fistula tract, the delivery device 900 can be removed from about the closure device 5. The removal of the delivery device 900 from about the closure device 5 may be accomplished by grasping an exposed portion of the delivery device 5 or a grasping member, for example, and then pulling or pushing the delivery device relative to the closure device 5. Alternatively, a hooked member having a hook or other engagement feature that engages an end of the delivery device 900 may be employed where the hooked member can be used to pull the delivery device 900 from about the closure device 5.

In other embodiments, the device 5 may be deployed via a guidewire with a hook-like feature at one end. Such a delivery device can be used for an anal fistula 10, where there is access at both a proximal and a distal end of the fistula tract 10 (in contrast to an enterocutaneous fistula, which has one external access point). The guidewire with the hook-like feature may be inserted into the fistula tract at a first end and passed through the tract 10 such that it can be used to pull the device 5 through the tract 10 by the hook to a second end. The distal end of the device 5, which may already be in an expanded state, may anchor the device 5 into the fistula tract. This embodiment of the delivery device may reduce the amount of work required of the surgeon as the hook may be used to pull the delivery device into place. In an additional embodiment, a guidewire or stylet may be extended through the device body 13 generally parallel to the connecting member 20. In other words the device body 13 may be threaded onto the guidewire or stylet. The guidewire or stylet may then be used to negotiate the device body 13 into the tract 10. Once positioned in the tract 10, the stylet or guidewire may be withdrawn from the device body 13. Where the device body 13 is threaded onto the stylet or guidewire, the bodies 15 may have holes therein for receiving the stylet or guidewire. Also, the bodies 15 may have slots through their sides that lead to the holes so the stylet or guidewire can be inserted into the holes without having to be placed therein via a threading motion. In versions of such embodiments, the slots and/or holes in the bodies 15 for receiving the stylet or guidewire in a threaded arrangement are configured to close after the stylet or guidewire is withdrawn from the bodies 15. The closure of the slots and/or holes may result from the expansion of the bodies 15.

Regardless of whether a catheter, sheath, guidewire or stylet or combination thereof is used to deploy the device 5 in the tract 10, once located within the tract 10, the device body 13 will begin to expand and fill the voids of the tract 10. Expansion of the bodies 15 may be a result of being free of the constraints of the lumen of the sheath, catheter or guidewire used to deliver the device 5. Expansion of the bodies 15 may be a result of being free of the constraints of a restraining mechanism such as a biodegradable ring, sheath, member, etc. extending about the bodies 15 when first deployed in the tract 10. Expansion may be a result of being exposed to body fluids or temperature within the tract 10. Expansion may be a result of any one or more of these aforementioned expansion methods.

As can be understood from FIG. 1B, the porous bodies 15 at the proximal and/or distal ends 31, 32 of the device 5 may be configured to protrude from the distal and/or proximal fistula openings when implanted in the fistula tract 10. As depicted in FIG. 1B, the protruding end 115 of the most distal body 110, or the entirety of the most distal body 110, may be configured to expand more than the rest of the porous bodies 15. Such an over-expanding capability at the distal ends 32 of the device 5 when within the fistula tract may produce an occluding and anchoring effect. Additionally or alternatively, the same concept may be applied to the most proximal body 15 at the device proximal end 31. Such embodiments can be considered to have at least one body 15 with a magnitude of expansion that is different from (i.e., exceeds) the magnitude of expansion of the other bodies 15. In one embodiment, a device 5 with a distal most body 110 that is configured to have increased expansion as compared to its fellow bodies 15 will be positioned in the tract 10 such that the most distal body 110 is partially within the tract 10 and partially extending from the distal opening 12 into, for example, the bowel lumen. Thus, as illustrated in FIG. 1B, once the distal portion of the device 5 is in place, the distal most body 110 of the device 5 expands to contact the edges of distal opening 12 of the fistula tract 10, thereby occluding the distal opening 12 of the fistula tract 10. The device 5 also expands to fill the rest of the fistula tract 10. To facilitate a generally complete sealing of the distal opening 12, the distal most body 110 of the device 5 may include an impermeable coating.

In a manner similar to that discussed above with respect to the distal most body 110, the proximal most body at the proximal end 31 of the device 5 may be adapted and configured to anchor or otherwise hold the device 5 in place within the fistula tract. Where both the distal and proximal most bodies are so configured, the distal and proximal most bodies will provide a counter force or counter balance to each other through the connecting member 20. In some embodiments, the proximal most and/or distal most bodies may be or include an adhesive layer to further strengthen the seal around the respective fistula tract openings.

Figure 1C:
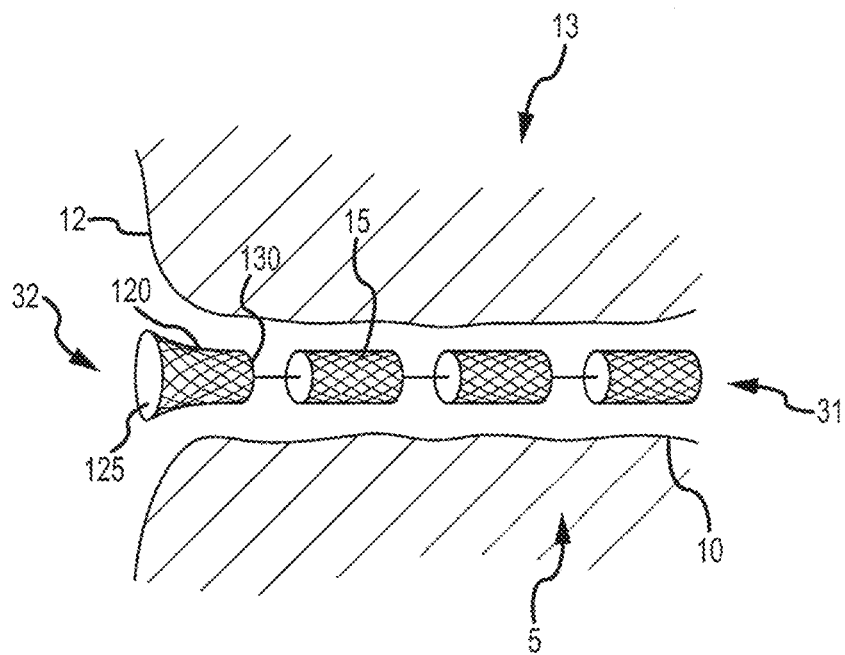
FIG. 1C is an isometric view of the implantable fistula closure device located in a fistula tract in a compressed or non-expanded state, where the distal most body of the device body has a conical shape, as opposed to a cylindrical shape.
Figure 1D:
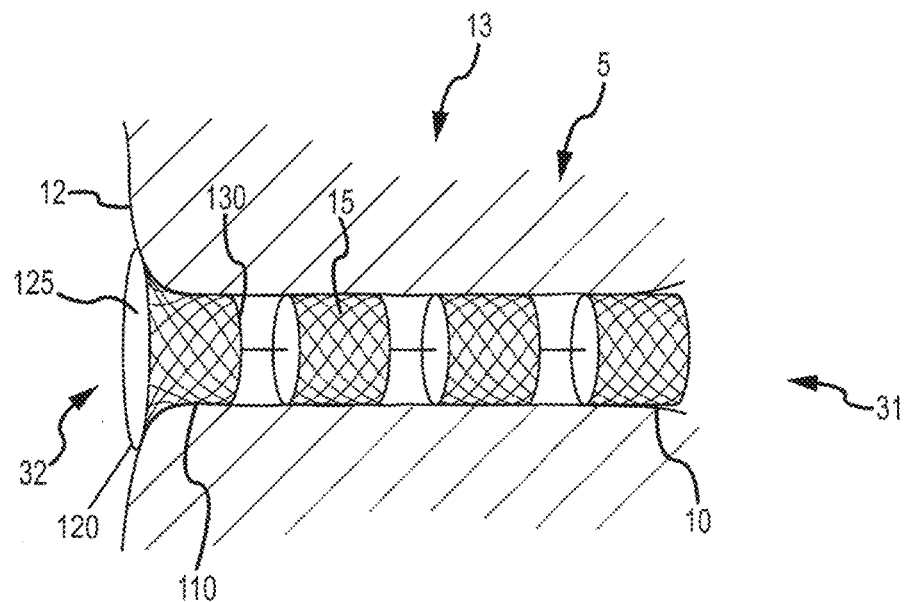
FIG. 1D is the same view as FIG. 1C, except the implantable fistula closure device is in a non-compressed or expanded state within the fistula tract.

For a discussion of distal most or proximal most bodies 15 having shapes other than generally cylindrical, reference is made to FIGS. 1C and 1D, which are respectively the same as FIGS. 1A and 1B, except illustrating the differently shaped bodies 15. As shown in FIGS. 1C and 1D, the distal most body 120 may have a shape that is non-cylindrical and, more specifically, conical. While not shown here, in some embodiments, the proximal most body 15 at the proximal end 31 of the device 5 may also have a conical shape as opposed to a cylindrical shape.

In some embodiments, the conically shaped most distal body 120 is generally shaped such that its distal end 125 is generally greater in diameter than its proximal end. The distal end 32 of the device 5 may be advanced into the distal opening 12 of the fistula tract 10 such that a distal portion 125 of the body 120 extends from the tract opening 12 into, for example, the bowel lumen. As illustrated in FIG. 1B, once the distal end of the device 5 is in place, the distal end 125 of the body 120 expands to contact the edges of the distal opening 12 of the fistula tract 10, thereby occluding the distal opening 12 of the fistula tract 10. The rest of the device body 13 also expands to generally fill the rest of the fistula tract 10 as described above. In some embodiments, the proximal end 31 of the device 5 does not extend beyond the edge of the fistula tract, while in other embodiments it does.

In some embodiments, the difference in diameter of the distal end 125 could be a result of a difference in the distance by which the different parts of the distal body 120 can expand. For example, the diameter of the cylinder in the compressed or non-expanded state is uniform; however, when the cylinder expands, the proximal end of the cylinder may reach the wall of the fistula tract 10, while the distal end may have a greater distance to expand before reaching the wall of the fistula tract 10 which corresponds to its target area of expansion. In this case, the diameter of the cylinder in a non-expanded state is uniform, but the diameter of the cylinder in the expanded state forms a conical shape.

Figure 2A:
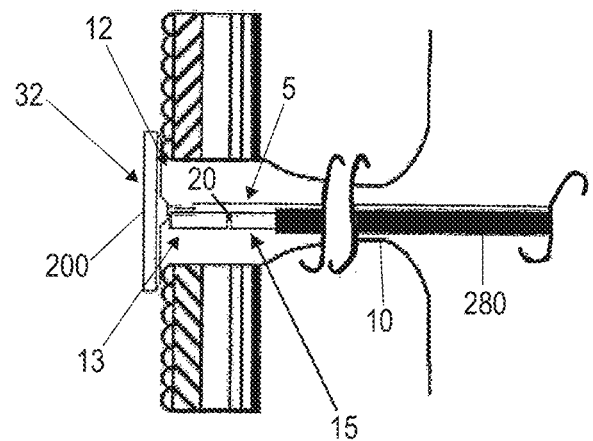
FIGS. 2A-2D provide an illustrative depiction of an embodiment of a method of sealing a fistula tract using a fistula treatment device.
Figure 2B:
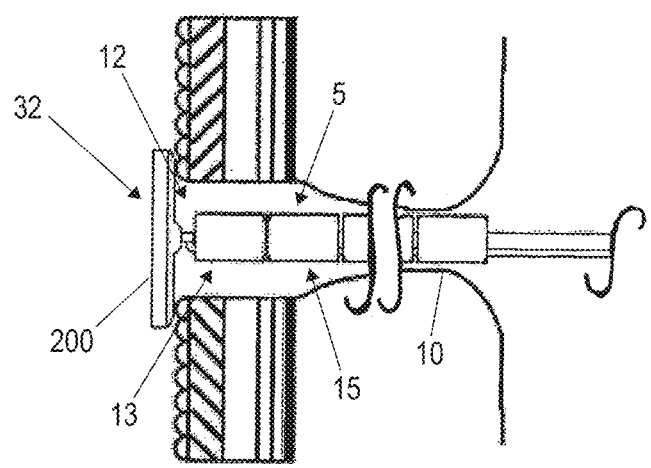

In FIGS. 2A and 2B, the device body 13 is similar to that discussed above with respect to FIGS. 1A and 1B, in that the device body 13 includes individual porous bodies 15 (delivered here by a delivery catheter 280) coupled together via a connecting member 20. However, here, and as indicated in FIGS. 2A and 2B, the distal end 32 of the device 5 terminates in an expandable member 200, which is coupled to the distal end of the connecting member 20. The expandable member 200 serves to anchor the device distal end in place at the fistula distal opening 12 and/or to seal the fistula distal opening 12.

The expandable member 200 may have any appropriate configuration, and in some cases may include a gel-filled or otherwise readily deformable member sandwiched between a pair of generally rigid discs. In some embodiments, the expandable member 200 may be shaped like a wagon wheel, with the outer rim being the sealing part and the spokes helping to distribute air and/or any other suitable inflation fluids. The expandable member 200 may, for example, comprise a generally flat and circular configuration, or may be thicker and non-circular, including oval or rectangular shaped devices. Although the expandable member 200 is depicted as comprising a generally planar configuration, in other variations, the expandable member may comprise a concave proximal surface and a convex distal surface, which can resiliently deform toward a flattened or everting configuration The expandable member 200 may be configured to be collapsed for delivery to the target location and to re-expand when deployed. In some examples, the expandable member 200 may comprise a resilient material that re-expands upon removal of any restraint acting on the collapsed body, such as the removal or withdrawal of a delivery catheter, or the cessation of suction or vacuum acting on the collapsed body. For example, the body may be molded (e.g., injection or blow molded) using polyurethane, polyvinyl chloride or any other suitable resilient polymeric material into its base configuration that may then be collapsed using suction or vacuum. In some examples, the expandable member 200 may comprise a shape-memory or superelastic material, including but not limited to nickel-titanium alloys or shape-memory polymers. In other examples, re-expansion may be facilitated by the infusion or inflation of a liquid or gas into the expandable member 200. The expandable member 200 may generally comprise any suitable material or materials. For example, in some cases the expandable member 200 may comprise one or more biocompatible polymers and/or one or more biodegradable or bioabsorbable materials. Expandable members are described, for example, in U.S. Patent Application Publication No. US 2010/0228184 A1, which is incorporated herein by reference in its entirety.

As shown in FIG. 2A, the delivery catheter 280 may be advanced (e.g., over a suture) to the target site. In some cases, the delivery catheter 280 may be advanced to the target site through a sheath (not shown). Once the distal end of the delivery catheter 280 is positioned at the target site, an actuator (not shown) may be inserted into the delivery catheter 280 until it is positioned against the proximal most expandable member 15. The position of the actuator may then be maintained while the delivery catheter 280 is proximally withdrawn to deploy the expandable members 15 into the fistula tract 10. The actuator and the delivery catheter 280 may then be proximally withdrawn from the sheath. It should be understood that this is only one example of a delivery method, and other suitable delivery methods may also be used, as appropriate.

In some embodiments, the expandable member 200 may comprises at least one inflatable balloon, chamber or cavity. The inflatable balloon may, for example, be advanced in a non-inflated state through the distal opening 12 of the fistula tract 10. Once in position, the balloon may be inflated (e.g., via a lumen in the connecting member 20) with a material such as air or saline, or another biocompatible fluid or solidifying gel. The balloon may be a fluid-inflatable or expandable disc-shaped balloon adapted to occlude the distal tract opening. Alternatively, the balloon may be a fluid-inflatable or expandable flat cone-shaped balloon adapted to occlude the distal tract opening. Other suitable shapes or configurations may also be used, e.g. a curved configuration with a distal convex surface and a proximal concave surface, as mentioned earlier. Tension may then be applied to the device 5 via the connecting member 20, to thereby cause the balloon to occlude the distal opening 12 of the fistula tract 10. In some variations, the expandable member 200 may be sufficiently resilient to achieve its expanded configuration when any collapsing force or structure is removed, but wherein the inflation chambers may be used to alter the resiliency, rigidity or other mechanical characteristics of the expandable member.

In some embodiments, one or more actuation mechanisms may be used to expand the expandable member 200, while in other embodiments, the expandable member 200 may be expanded without any actuation mechanisms. For example, the expandable member 200 may expand upon exposure to body fluids or a temperature differential within the tract 10, or via its own biased nature. In addition to the expandable member 200 expanding to anchor the device 5, the device body 13 expands to generally fill the rest of the fistula tract 10 as described above, and as depicted in the progression from FIG. 2A to FIG. 2C.

In some embodiments of a fistula closure device 5 equipped with an expandable member 200, the device 5 and its expandable member 200 in a non-expanded state are configured to pass through a lumen of catheter size of nine French or smaller, and in some embodiments, twenty French or smaller.

In certain embodiments, the expandable member 200 may comprise an adhesive coating adapted to adhere to the tissue surface of the region adjacent the distal opening 12 of the fistula tract 10, while in other examples, the adhesive may be light curable, where the light is provided via a fiberscope inserted into the fistula tract (with or without the delivery tool or a cannula in place), or in some variations, via the lumen of the gastrointestinal tract. The adhesive may activate after exposure to a fluid (e.g., body fluid) or body temperature. The adhesive may initially strengthen the bond of the member 200 to the tissue and then gradually degrade in strength as fistula tract healing occurs or after fistula tract healing. Depending on the embodiment, the adhesive may create a fluid impermeable seal for at least 7, 14, 21, 28, 35, 60 or any other number of days.

In certain embodiments, an expandable member 200 may include attachment members, such as micro hooks or tines. Such attachment members may be located on a surface of the expandable member 200 intended to contact the tissue surface area forming the opening 12, thereby facilitating the adherence of the expandable member to the tissue surface bordering the distal tract opening and the occlusion thereof.

In some embodiments, an expandable member 200 or various components thereof may be resorbable and adapted to occlude the fistula tract and then resorb after the tract 10 has closed at least about 45%, 55%, 65%, 75%, 85%, 95%, 100% or any other percentage. The expandable member 200 or various components thereof may be biodegradable and/or adapted to fall away from the distal fistula opening 12 and be extruded through the gastrointestinal tract. For example, the expandable member 200 or various components thereof may be secreted from the body after the tract 10 has progressed towards closure (e.g., after at least 7, 14, 21, 28, 35 or any other number of days adequate to achieve sufficient closure).

In some embodiments, the connecting member 20 may be a biocompatible polymer string extending through the tract from the expandable member 200. The connecting member 20 may be formed of one or more resorbable materials and may resorb after the tract 10 has closed at least about 45%, 55%, 65%, 75%, 85%, 95%, 100%, or a percentage range between any two of the above percentages. The connecting member 20 may provide tensile force substantially perpendicularly to the expandable member 200, thereby pulling the expandable member 200 against the tract's distal opening 12 and anchoring the expandable member 200 in place to occlude the distal tract opening.

Figure 3A:
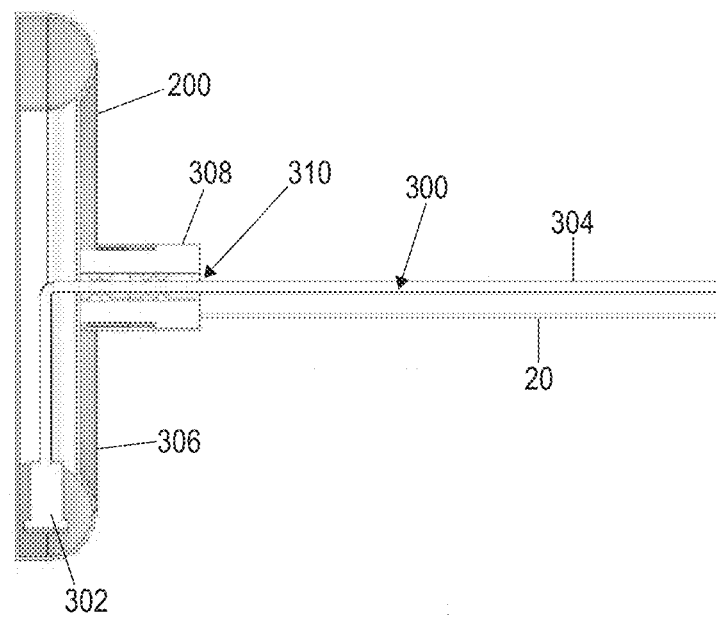
FIGS. 3A and 3B illustrate the sealing of an embodiment of an expandable member of a fistula treatment device.
Figure 3B:
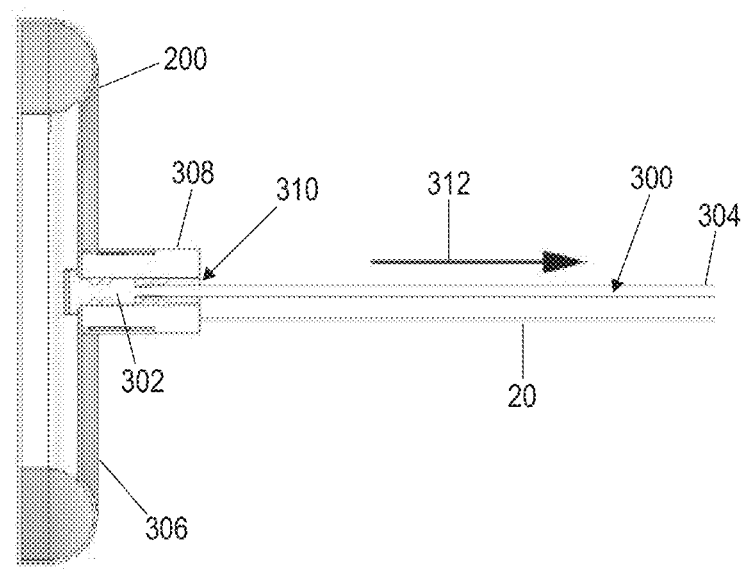

Expandable members or components 200 may have any suitable shape or configuration, and may be actuated using any appropriate mechanism. In some cases, a plugging mechanism may be used to seal an expandable member 200 (e.g., after the expandable member has been positioned at a target site and expanded). For example, FIGS. 3A and 3B show an expandable member 200 coupled to a connecting member 20 (e.g., that may be used for loading one or more porous bodies 15), where a plug member 300 is used to seal the expandable member when it is expanded. As shown, the plug member 300 comprises a plug portion 302 and an elongated member 304 (e.g., a suture) coupled to or integral with the plug portion. The expandable member 200 in this embodiment comprises a disc-shaped portion 306 and a tip portion 308, although other configurations may also be used. In FIG. 3A, the expandable member 200 has not yet been sealed. However, in FIG. 3B, the plug member 300 has been actuated to move the plug portion 302 into the tip portion 308 of the expandable member, and to thereby seal an aperture 310 in the tip portion. The plug member 300 may be actuated, for example, by proximally withdrawing the elongated member 304 (i.e., in the direction of arrow 312). While not depicted here, in certain embodiments, it may also be possible to undo the seal (e.g., by pushing on the elongated member 304 and thereby disengaging the plug portion 302 from the tip portion 308).

Figure 5A:
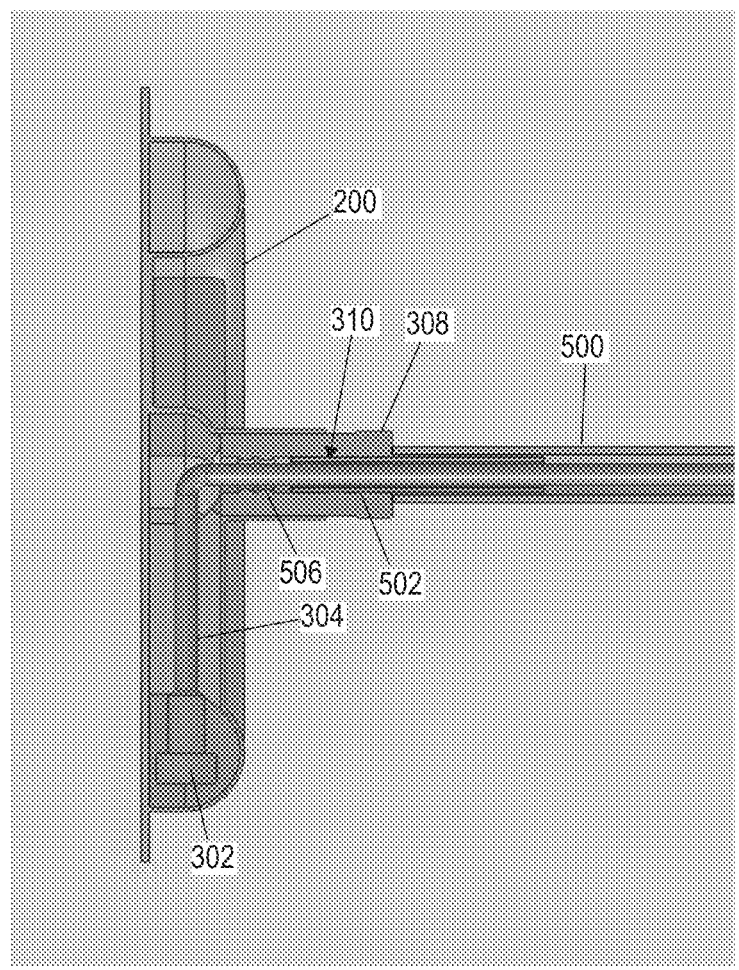
FIGS. 5A-5C depict the sealing of an embodiment of an expandable member of a fistula treatment device.
Figure 5B:
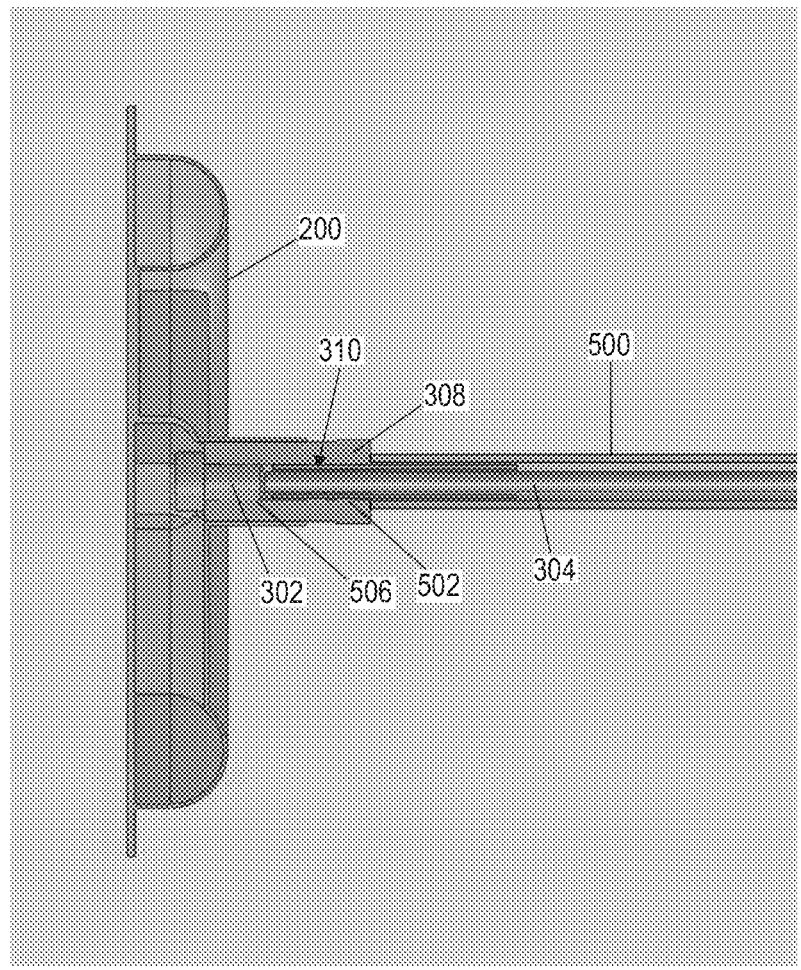
Figure 5C:
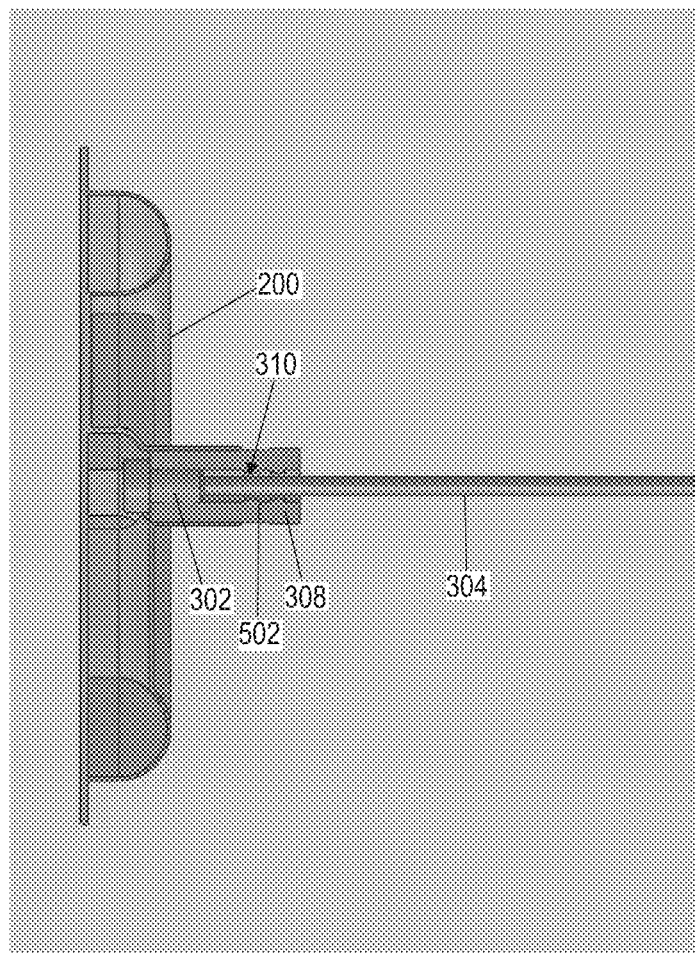

FIGS. 5A-5C similarly depict the sealing of an embodiment of an expandable member 200. First, as shown in FIG. 5A, the expandable member 200 has been delivered to the target site, but is not yet sealed. The delivery catheter 500 engages ribs 502 of the tip portion 308 of the expandable member 200 and thereby stabilizes the position of the expandable member 200. In some embodiments, the expandable member 200 may be expanded by injecting inflation fluid in the proximal end of the delivery catheter 500, such that the inflation fluid travels through the delivery catheter 500 into the expandable member 200 and thereby inflates the expandable member 200.

In FIG. 5B, the elongated member 304 has been proximally withdrawn to move the plug portion 302 into the aperture 310 in the tip portion 308 of the expandable member 200. This positions the plug portion 302 in the sealing position, where it seals the expandable member 200. As shown, the plug portion 302 now engages ribs 506 of the tip portion 308 of the expandable member 200. Finally, FIG. 5C shows the sealed expandable member 200, when the delivery catheter 500 has been disengaged therefrom (e.g., by being proximally withdrawn).

While plug members comprising elongated members and plug portions have been described, other embodiments of plug members having different components and/or configurations may also be used, as appropriate. For example, a plug member may comprise multiple plug portions and/or a plug portion having a different configuration.

Figure 4:
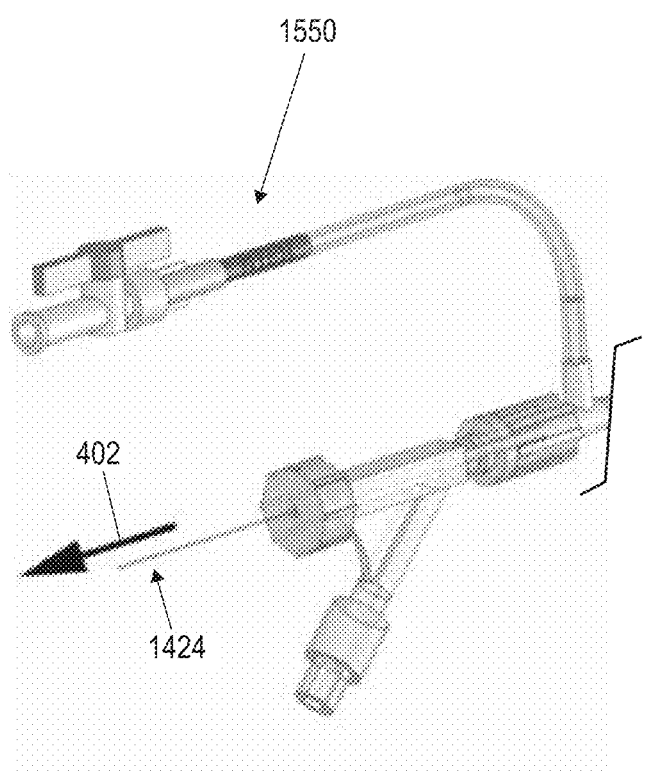
FIG. 4 illustrates the actuation of an embodiment of a fistula treatment device to seal the expandable member shown in FIGS. 3A and 3B.

Once the expandable member 20 has been expanded, it may be used to seal the distal opening of a fistula tract. FIG. 4 depicts the actuation of a delivery instrument 1550 (shown in its entirety in FIG. 15B), by pulling on the tether 1424 in the direction of arrow 402, to tension the tether and thereby seal the distal opening of the fistula tract 10 with expandable member 20. While one actuation mechanism is shown, other appropriate actuation mechanisms may alternatively or additionally be used.

As discussed above, in some embodiments of the device 5, the proximal end of the device may be adapted and configured to receive a proximal clip that secures the device in place. The clip may, for example, be disc-shaped, or may have a different (e.g., polygonal) shape. The clip may be made of any biocompatible material, such as PGLA, PVA or PVC, or any other suitable biocompatible polymer or plastic. The material may also be resorbable. In use, the clip may extend across the proximal end of the fistula tract 10 and may be generally flush or slightly raised relative to the proximal end of the fistula tract 10. The clip may help to maintain tension on the connecting member 20 that couples the expanding member 50 with the clip, thereby helping to maintain or anchor the device 5 in the tract 10. The clip may be coupled to the connecting member 20 in any appropriate fashion, such as via friction, pinching, suturing or any other suitable method.

Features of the clip and/or proximal end 31 of the device 5 may be transparent to allow visual inspection of the tract. In some embodiments, the clip and/or proximal end of the device may be adapted to cover the proximal end of the fistula tract without completely sealing the proximal end of the tract, thereby allowing accumulating fluids to drain or escape from the proximal end of the tract. In some cases, the clip may comprise a mesh-like membrane that permits drainage of accumulating fluids from the proximal end of the tract. After the tract 10 heals, the proximal clip may resorb or otherwise be removed.

Referring back to FIGS. 2C-2F, in addition to effectively anchoring the distal end of a device 5 (as shown, using an expandable member 200), the proximal end of a device may also be stabilized or positioned with a proximal anchor 250.

In FIGS. 2C-2F, tethers 254 and 256 that are attached to the expandable member 200 may be used to apply tension to the expandable member 200 to thereby seal the fistula tract 10. In some examples, at least one of the tethers (e.g., tether 256) may be provided to as a guide element for delivery of the expandable members 15 of the body 13 along the fistula tract 10. At least one or both of the tethers 254 and 256 may be secured using the proximal anchor 250. This securing of the tethers 254 and 256 makes distal sliding or displacement of one or both of the tethers less likely, as the proximal anchor 250 provides an increased surface area or transverse dimension that resists collapse or entry of the proximal anchor 250 into the fistula tract. The proximal anchor 250 may help to maintain the tension in one or both of the tethers 254 and 256.

In use, the proximal anchor 250 may be slid onto one or both of the tethers and positioned adjacent the skin surface (e.g., after the expandable members 15 have been expanded in the fistula tract 10 by, for example, infusing saline into the fistula tract). While maintaining tension on the tension tether 254 through the proximal anchor 250, the delivery tether 256 may be sutured or otherwise attached to the surrounding tissue using a free needle passed through the proximal anchor 250 and tied to the tissue with the desired tension. At a location opposing the delivery tether 256 on the proximal anchor 250, a free needle may be used to pass through the proximal anchor 250 and to suture the tension tether 254 to the surrounding tissue. Additional sutures (e.g., 3-0 or 4-0 nylon) may be used to further secure the proximal anchor 250 to the surrounding superficial tissue as needed.

The size and shape of the proximal anchor 250 may depend, for example, upon the particular fistula being treated. In some embodiments, the proximal anchor 250 may have a diameter or maximum transverse dimension that is at least the same as that of the expandable member 200. In further examples, the diameter or maximum transverse dimension may be at least two times, three times, or four times or greater than the corresponding dimension of the expandable member 200. The expandable member 200 and the proximal anchor 250 may both have the same shape (e.g., circular) or may have different shapes.

The proximal anchor 250 may also comprise one or more securing apertures 258 that may permit the attachment of the proximal anchor 250 to the skin or a bandage surrounding the dermal fistula opening. These securing apertures 258 may be spaced around the periphery of the proximal anchor 250, closer to the outer edge rather than the center of the proximal anchor 250. Any suitable number of apertures having any appropriate size may be used. In other examples, the proximal anchor 250 may comprise an adhesive surface that contacts the skin surrounding the fistula and resists movement. The tethers 254 and 256 of the device may be secured to the proximal anchor 250 by any of a variety of mechanisms, including a clamping structure, adhesive, or by a deformable slit that provides a releasable friction fit interface for the tethers 254 and 256. The attachment site of the tethers 254 and 256 on the proximal anchor 250 may further comprise access openings that may be used to infuse therapeutic agents into the fistula, and/or to permit passive or active fistula drainage, or the application of negative pressure therapy to the fistula.

Figure 2C:
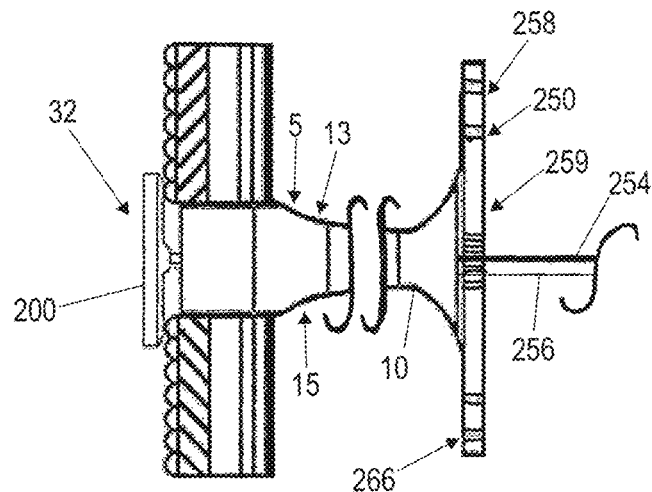

FIG. 2C depicts a proximal anchor 250 comprising just a single body 259. However, in FIGS. 2D and 2E, the proximal anchor 250 is depicted as comprising a first portion 260 and a second portion 262 that is movably coupled to the first portion by a plurality of resilient members 264. The first portion 260 is the more distal portion of the proximal anchor 250, and may have a tissue contact surface 266 that is configured to resist passage into a fistula of the type being treated (e.g., an enterocutaneous fistula). The first portion 260 also comprises an aperture 267 that permits slidable coupling to at least one tether (e.g., tethers 254 and 256). The second portion 262 is the more proximal portion of the proximal anchor 250, and comprises a tether-fixing structure 268 configured for affixation of at least one tether (e.g., tethers 254 and 256) thereto. For example, at least one tether may be tied to the tether-fixing structure 268.

Figure 2D:
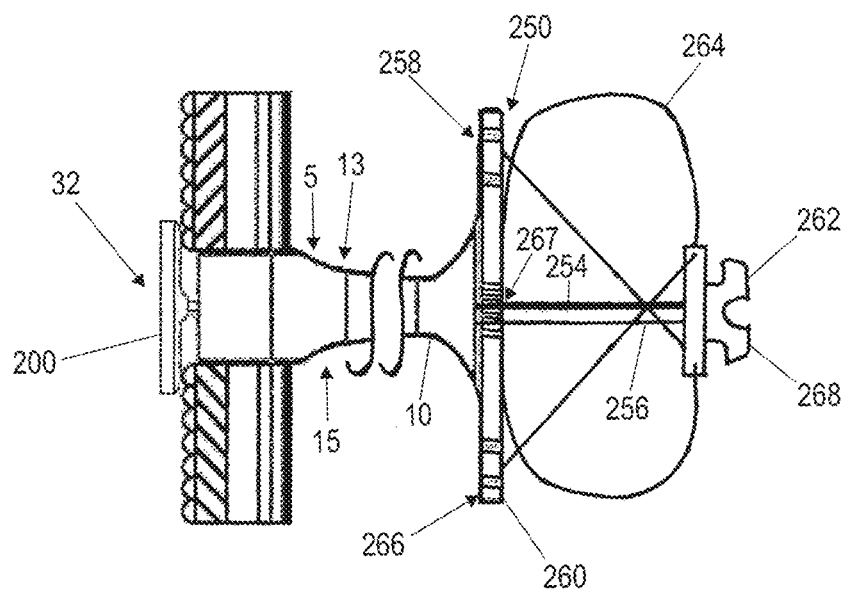

During use, when the first and second portions 260, 262 are coupled to a tether, the first and second portions can move relative to each other to accommodate changes in the length of tether between them. For example, movement by the patient may necessitate having a lesser or greater length of tether between the first and second portions. The ability of the first and second portions to move relative to each other may allow for such a change to take place without, for example, resulting in tether breakage or excessive tether slackness. While the first and second portions 260, 262 of the proximal anchor 250 of FIGS. 2D and 2E are allowed to move relative to each other as a result of the resilient members 264, in other embodiments, different portions of a proximal anchor 250 may be movably coupled to each other in other ways, as discussed in additional detail below.

It should be noted that any of the proximal anchors described herein may be configured to allow for negative pressure transmission (e.g., negative pressure wound therapy), as appropriate. For example, the proximal anchors may include one or more apertures configured for negative pressure wound therapy. A vacuum pump may be applied to suction out fluid and/or collapse dead space to facilitate healing.

Figure 6A:
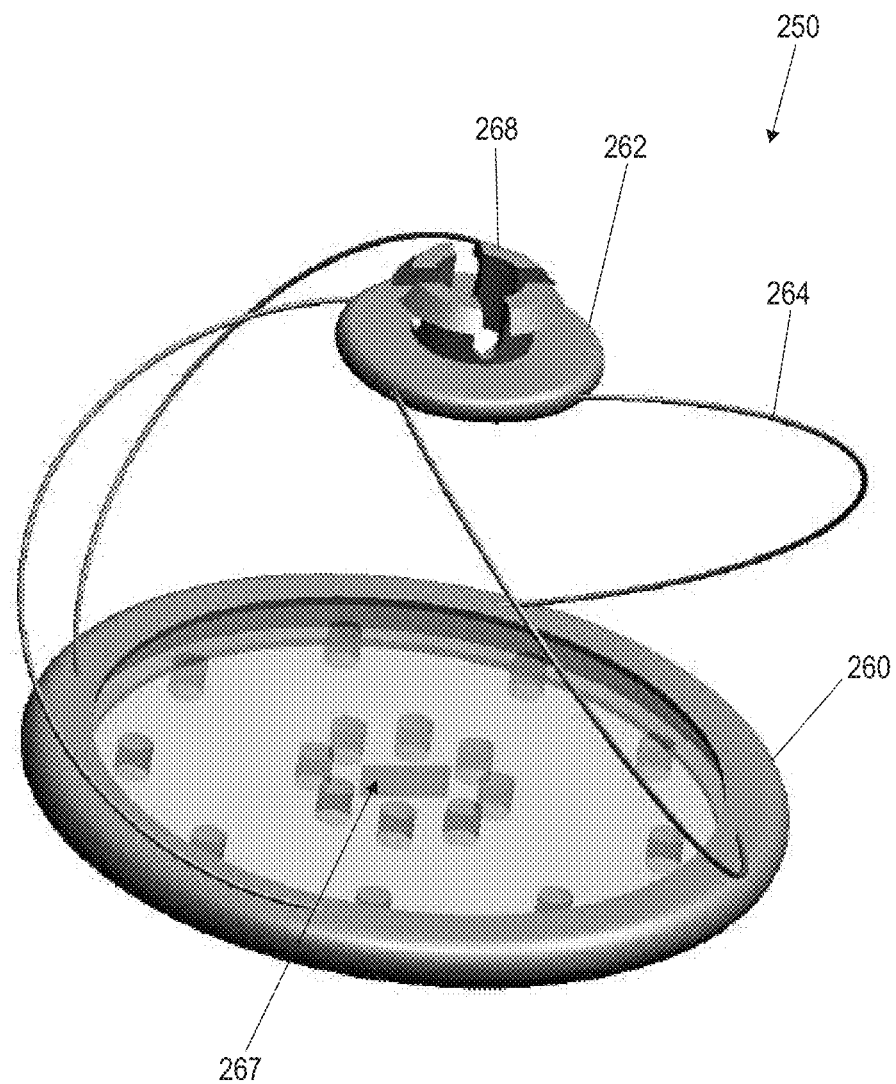
FIG. 6A is a perspective view of an embodiment of a proximal anchor of a fistula treatment device.
Figure 6B:
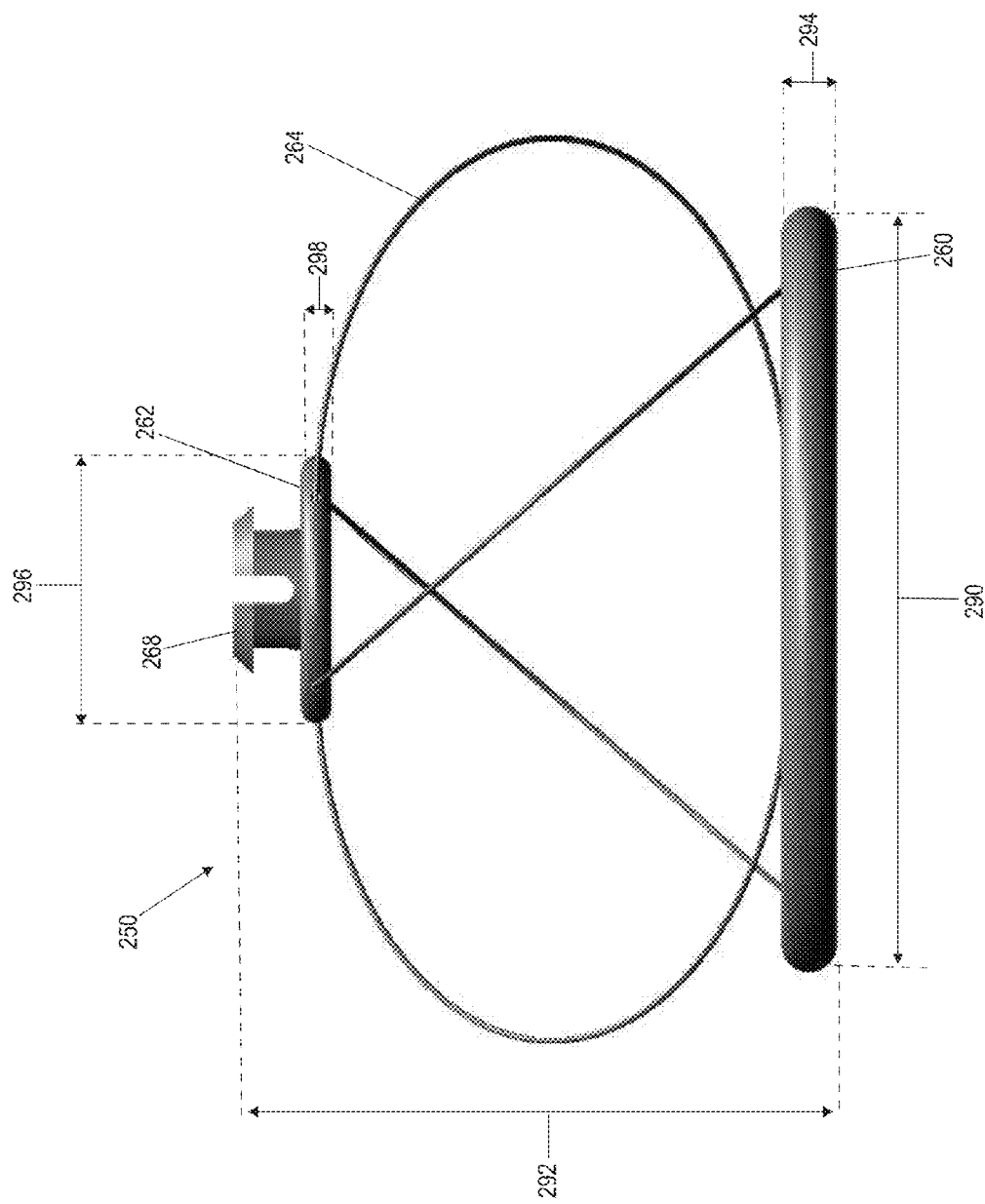
FIG. 6B is a side elevational view of the proximal anchor of FIG. 6A.
Figure 6C:
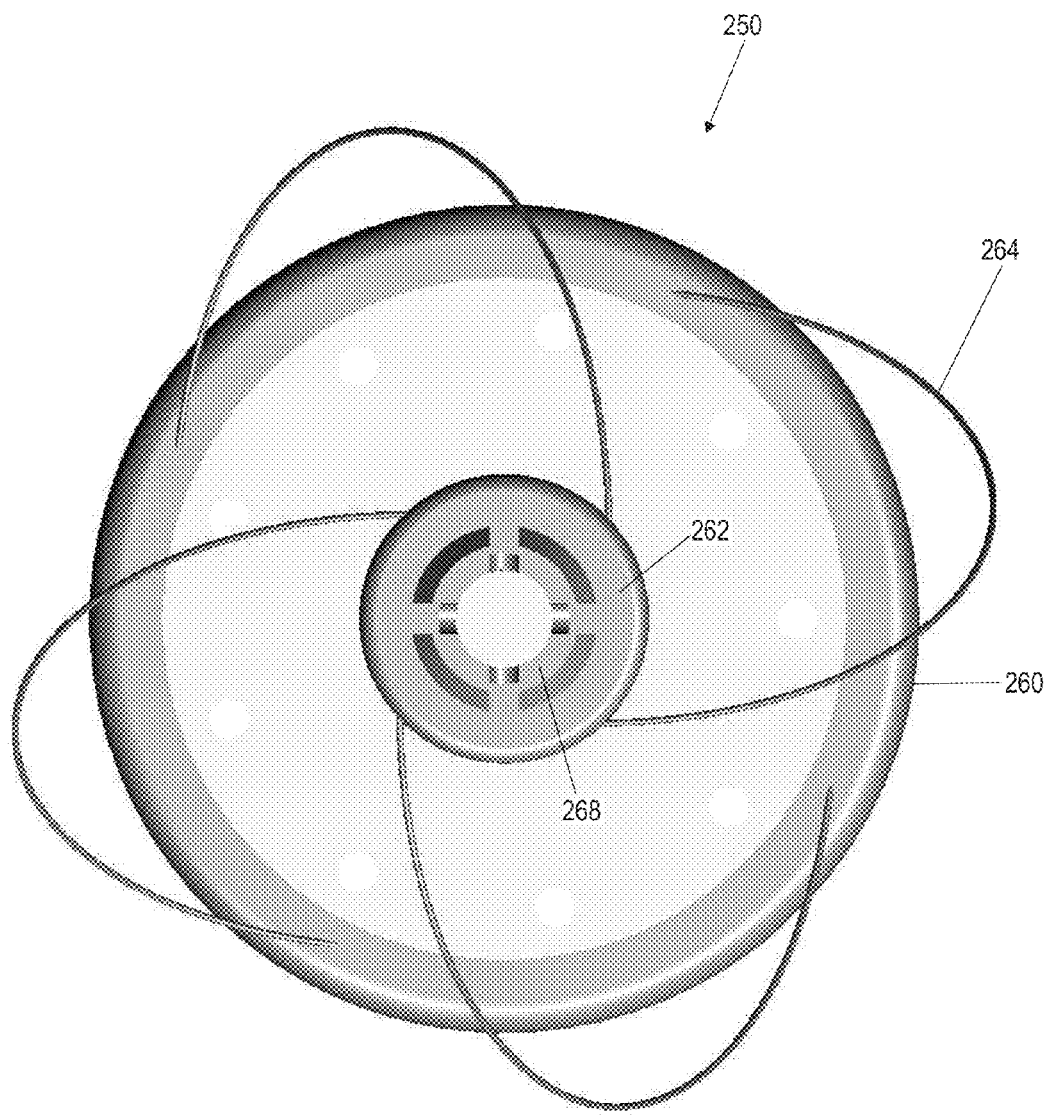
FIG. 6C is a top view of the proximal anchor of FIG. 6A.

FIGS. 6A-6C provide enlarged views of the proximal anchor 250 comprising first and second portions 260, 262. As shown in FIG. 6B, proximal anchor 250 has an overall height 292, first portion 260 has dimensions 290 and 294, and second portion 262 has dimensions 296 and 298. In some embodiments, overall height 292 may be from about 0.25 inch to about 0.75 inch, dimension 290 may be from about 0.5 inch to about 1.5 inches, dimension 294 may be from about 0.1 inch to about 0.5 inch, dimension 296 may be from about 0.15 inch to about 0.5 inch, and/or dimension 298 may be from about 0.05 inch to about 0.25 inch. Proximal anchor 250 may be made of any suitable material or materials, including but not limited to polymers, metals (e.g., titanium) and/or metal alloys (e.g., stainless steel). First and second portions 260, 262 may comprise the same material or materials, or may comprise different materials. In certain embodiments, resilient members 264 may comprise one or more metal alloys, such as Nitinol.

Figure 2E:
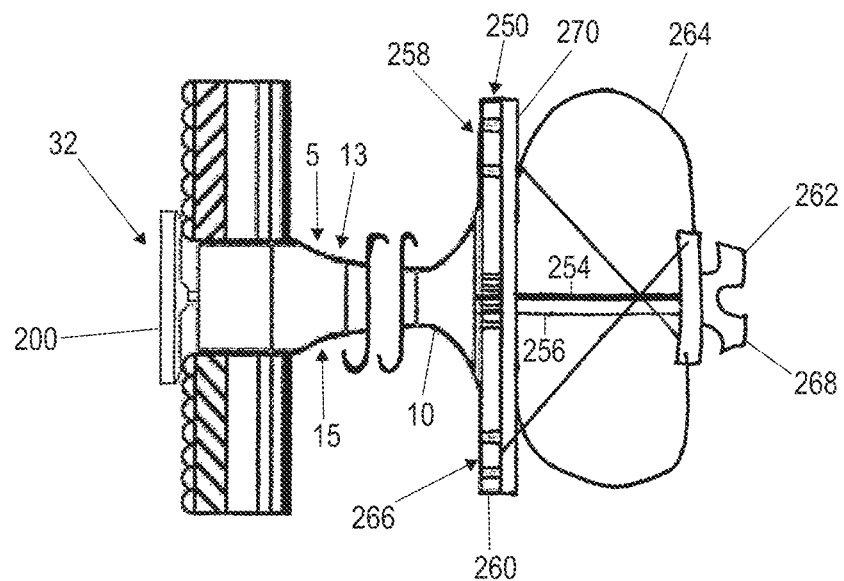
FIG. 2E depicts an embodiment of a dressing being used with the fistula treatment device of FIGS. 2A-2D after the fistula tract has been sealed.
Figure 2F:
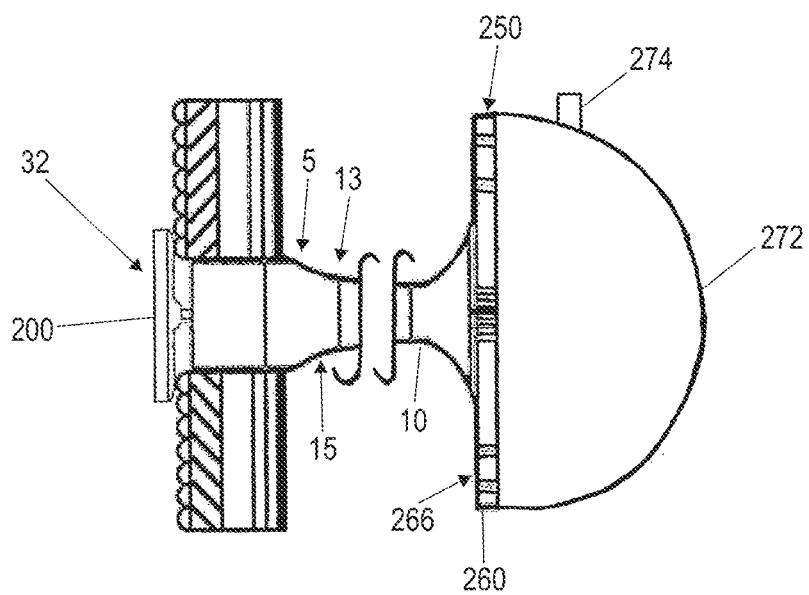
FIG. 2F depicts an embodiment of a seal or cover being used with the fistula treatment device of FIGS. 2A-2D after the fistula tract has been sealed.

Referring to FIG. 2E, in some cases, an absorbent dressing 270 may be positioned securely on top of the proximal anchor 250 to absorb any excess drainage that may occur. Alternatively, active drainage of the fistula/wound may be performed using wound drainage products or negative pressure wound therapy products. In certain cases, a proximal anchor may be configured both to accommodate negative pressure wound therapy and to accommodate an absorbent dressing. Also, prophylactic antibiotics may be optionally provided post-procedure. In some cases, and referring now to FIG. 2F, a protective cap 272 (e.g., that may be relatively rigid) may be provided over the proximal anchor 250. The protective cap 272 may, for example, be formed of one or more polymers, metals and/or metal alloys. As shown, the protective cap may comprise at least one vacuum port 274 (e.g., to allow for negative pressure wound therapy).

Figure 7A:
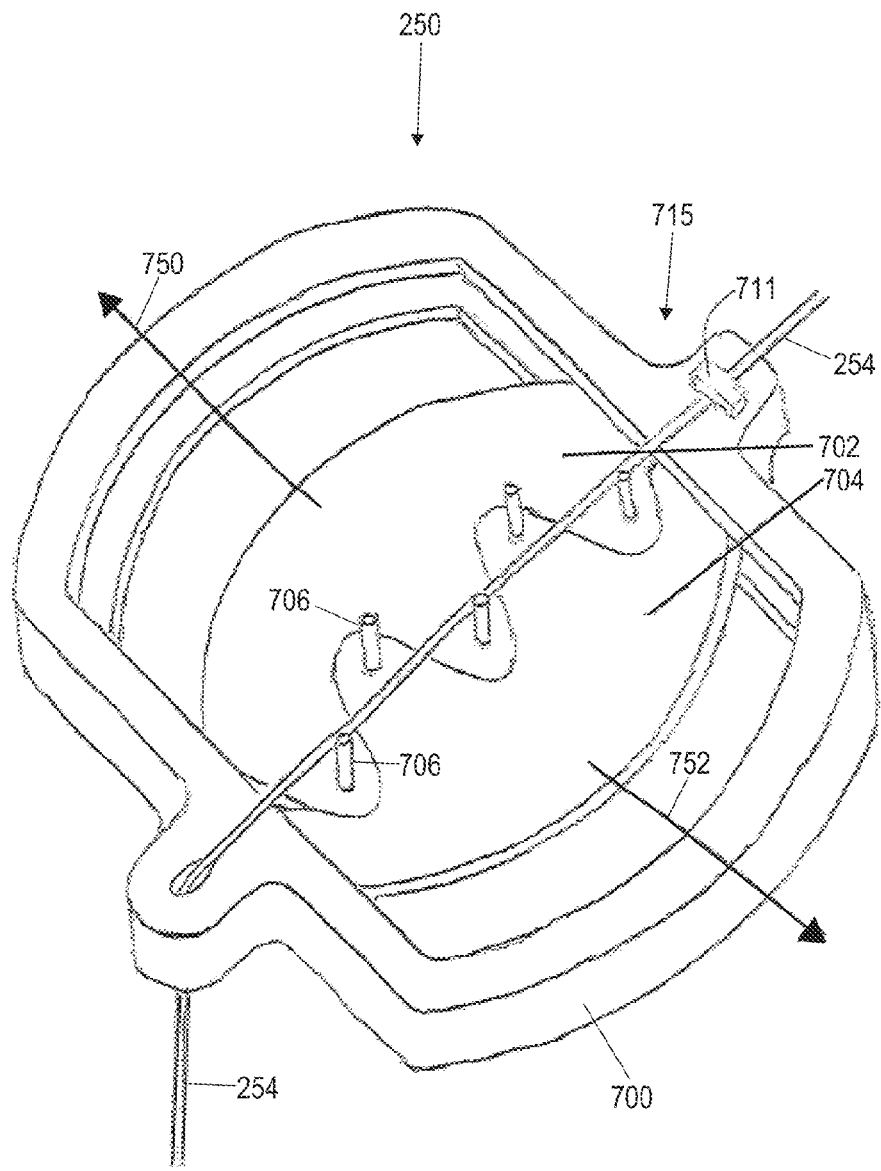
FIGS. 7A and 7B provide an illustrative depiction of a method of using an embodiment of a proximal anchor of a fistula treatment device.
Figure 7B:
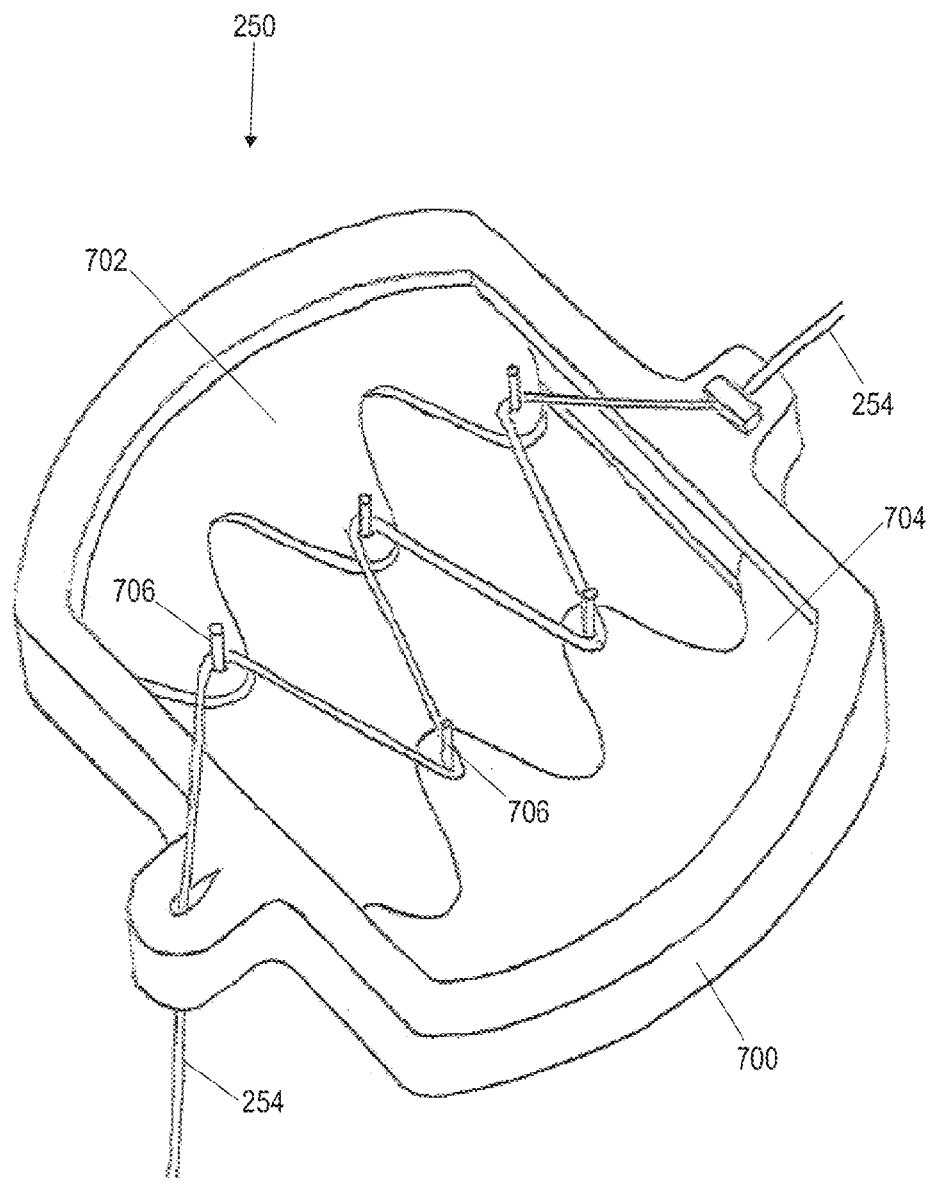

FIGS. 7A and 7B show an alternative embodiment of a proximal anchor 250, in which the direction of force is parallel with the skin surface. In other words, here the tether is tensioned with a force that generally is not directed outward from the body. Drag on the tether may be reduced by using a large radius for the transition in which the tether changes direction during use. The embodiment shown in FIGS. 7A and 7B has an interlocking design that advantageously would minimize the space required to accommodate a relatively long tether length, while still allowing for tether movement. More specifically, in FIGS. 7A and 7B, the proximal anchor 250 comprises a frame member 700 and first and second portions 702, 704 that are slidably coupled to the frame member and that are configured to interlock with each other. While one interlocking configuration is shown, other configurations (e.g., using different interlocking shapes) may also be used, as appropriate.

The first and second portions 702, 704 of the proximal anchor 250 comprise protruding members or pegs 706 through which at least one tether (here, the tension tether 254) may be routed. Additionally, the proximal anchor 250 comprises a tether clamp 711 that may be used to lock or secure the tether 254 at a proximal location 715. During use, the first and second portions 702, 704 may slide away from each other (in the directions of arrows 706, 708) and toward each other, to accommodate for variations in the length of tether extending from the skin surface. For example, in FIG. 7A, a relatively short amount of the tether 254 extends from the skin surface. However, as shown in FIG. 7B, when a greater length of the tether 254 extends from the skin surface, the proximal anchor 250 can accommodate for the difference without decreasing the tension in the tether. Similarly, the length of the tether 254 extending from the skin surface may become shorter without resulting in breakage of the tether. While not shown, in some cases a cover may be positioned over this proximal anchor 250 (e.g., to prevent interference from clothing, blankets, negative pressure wound therapy, or the like).

Figure 11:
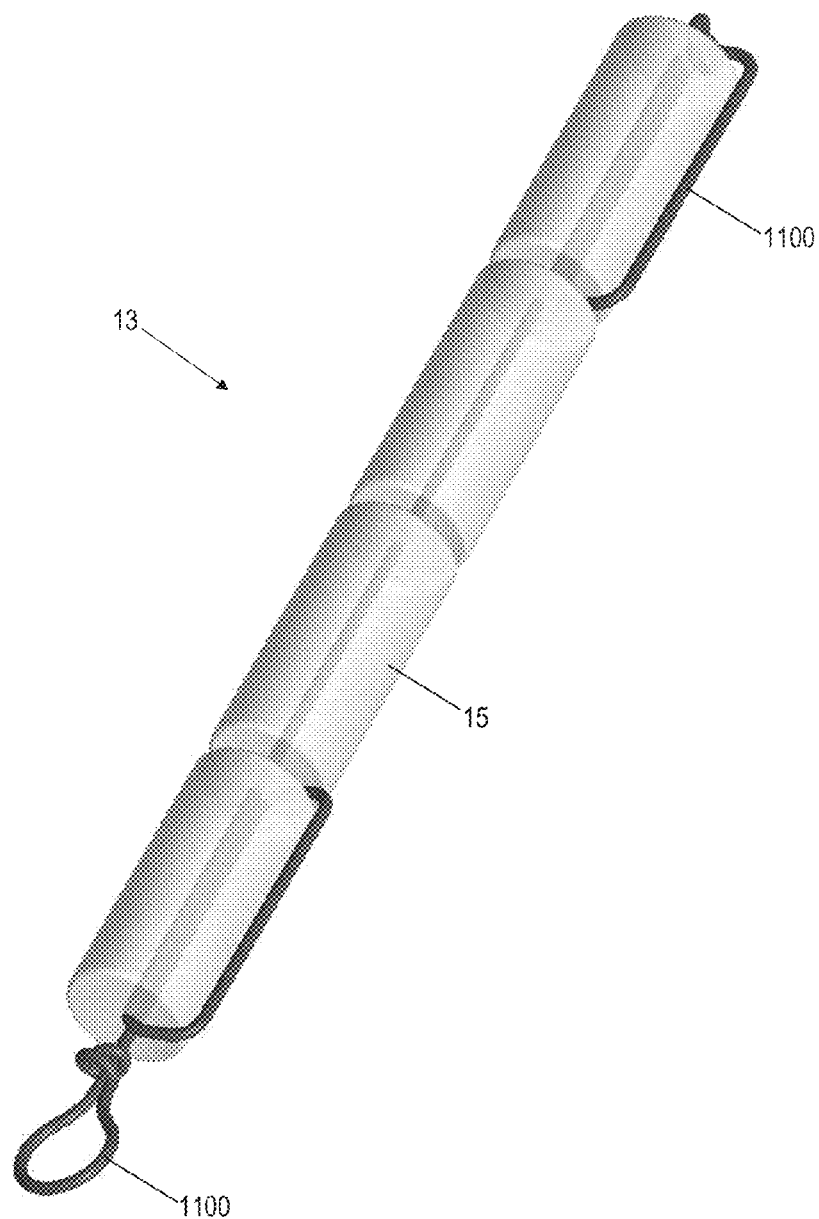
FIG. 11 is a perspective illustration of an embodiment of a component of a fistula treatment device.
Figure 12:
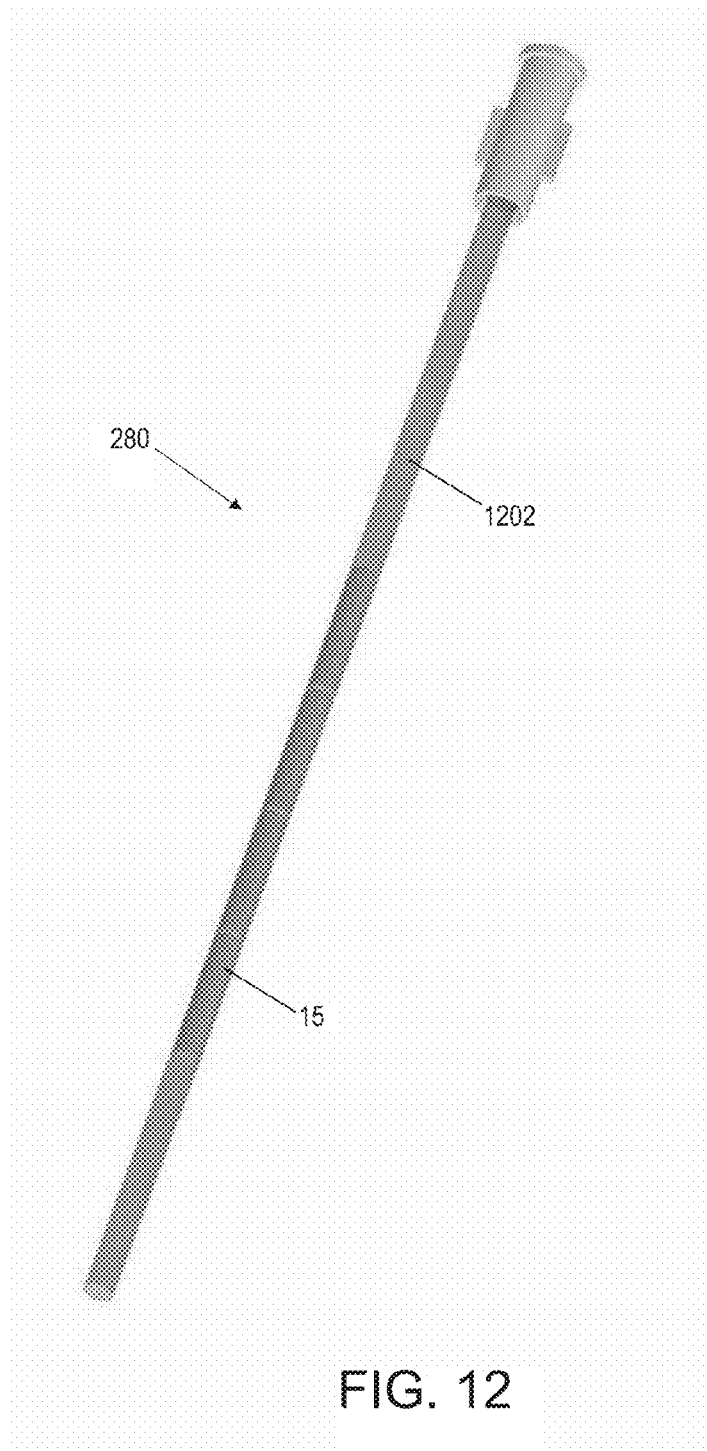
FIG. 12 is a perspective illustration of an embodiment of another component of a fistula treatment device.

As discussed above, methods described herein employ expandable members 15 to fill a fistula tract. Different expandable members 15 and arrangements thereof may be used with the devices, methods and kits described herein, as appropriate. FIG. 11 shows just one example of a device body 13 comprising expandable members 15 coupled together with a suture 1100. Additionally, FIG. 12 shows a delivery catheter 280 comprising a tubular member 1202 and expandable members 15 disposed within the tubular member 1202. The delivery catheter 280 may be used to deliver the expandable members 15 to a target site.

In some embodiments, the expandable members 15 of the device 5 may comprise porous bodies. For example, the expandable members 15 may comprise a compressed open cell polymer and may be made of any synthetic or natural biodegradable, resorbable, biocompatible polymer or polymers, such as collagen, hyaluronic acid and polyglycolic acid ("PGA"). The biodegradability may allow for degradation at a specified rate that matches the rate of tissue ingrowth and fistula tract healing, such that by the time the fistula tract is healed, the material is completely absorbed by the body. It should be noted that in some cases, the fistula tract may heal before the material is completely absorbed by the body. That is, the degradation rate of the device may not match, or may be slower than, the rate of tissue ingrowth and fistula tract healing.

Expansion of the bodies 15 within the tract 10 provides a porous scaffold to the fistula tract and may partially or entirely stop the flow of bodily fluids through the tract. The scaffold provides a matrix that may promote tissue in-growth, allowing the fistula to close. In certain embodiments, one or more antimicrobial agents, such as silver, may be incorporated in the porous bodies 15 and/or in the insertion methodology to actively prevent infection and/or sepsis formation and aid in the healing of the tract. The porous bodies 15 may include wound-healing agents, such as growth factors. In some embodiments, the porous bodies may include fibrosis-promoting agents.

A porous body may be adapted and configured to expand after placement in the fistula tract and to absorb fluid, thereby approximating closely the tract intra-luminal walls. In some embodiments, a porous body may include a porous resorbable open cell polymer foam adapted to expand and serve as a scaffold for tissue growth and closure of the fistula tract.

In certain embodiments, a porous body may comprise collapsed or compressed pores, adapted and configured to increase in size after placement in a fistula tract, thereby filling the fistula tract. In some embodiments, the pores of the bodies may advantageously be of a reduced size. For example, pore size may vary from 5 to 1000 microns with an overall porosity of 25-95%. In certain embodiments, bodies with a controlled pore size (i.e., without a broad distribution of pore sizes) of between approximately 50 microns and approximately 100 microns may be used. A body with a controlled pore size may promote greater angiogenesis, which, in turn, may promote better wound-healing. Examples of materials that may provide some or all of the controlled pore size and porosities include various biomaterials manufactured by Kensey Nash Corporation, CollaPlug® or other collagen products as manufactured by Integra Corporation, and STAR® materials as manufactured by Healionics Corporation.

In some embodiments, the fluid permeability (i.e., porosity or pore size) of the bodies 15 may increase from the distal end of the device 5 to the proximal end of the device 5. For example, a first body 15 at the distal end of the device 5 may have a lower fluid permeability than other bodies 15 of the device 5. That is, in a segmented body 13, a most distal body 15 or the most distal several bodies 15 (i.e., the single body 15 or the few multiple bodies 15 in closest proximity to the distal end of the tract, e.g., at the bowel end of the tract) may have the lowest fluid permeability and the bodies 15 extending proximally away from the most distal body 15 may have a higher fluid permeability. In certain embodiments, the fluid permeability of the bodies 15 proximal to the most distal body or bodies 15 may increase from body to body, moving in the proximal direction. A most distal body 15 or bodies 15 with a lowest fluid permeability may further enhance occlusion of the distal end 12 of the fistula tract 10 and prevent unwanted fluid from the bowel from entering the fistula tract. The bodies 15 proximal of the most distal body 15 or bodies 15 may have a higher fluid permeability to permit drainage of fluids accumulating in the tract and to promote tissue ingrowth to facilitate healing of the fistula tract.

A non-segmented body 13 may have a fluid permeability (i.e., porosity or pore size) that changes along its length. For example, the distal portion of the non-segmented body 13 may have a lower fluid permeability as compared to the proximal portion.

The porous bodies 15 may be in the form of polymer members that are anisotropic. For example, in some embodiments, the polymer members 15 may be anisotropic such that they have substantial radial expansion, but minimal, if any, longitudinal expansion.

In certain embodiments, the porous bodies 15, when in a compressed or non-expanded state, may have a volume that is significantly less than the volume of the bodies 15 when in a non-compressed or expanded state. For example, in some embodiments, the compressed or non-expanded volume of the bodies 15 may be between approximately 10% and approximately 60% of the non-compressed or expanded state volume. In certain embodiments, the compressed volume may be between approximately 20% and approximately 25% of the expanded volume. As a result, the bodies 15 may expand between approximately four and approximately five times their compressed volumes when expanding from a compressed state to an expanded state. For example, a body 15 with a porosity of 80% can be compressed to 20% of its expanded state. In other words, the body 15 may expand approximately five times its compressed volume when expanding from a compressed to a non-compressed state. The body 15 may expand even more if it retains any absorbed fluid from the fistula tract 10.

The porous bodies 15, when in a compressed or non-expanded state, may be relatively easy to insert in a fistula tract 10 and may cause less damage upon insertion due to the reduced size. The compressed porous bodies 15 also may allow for controlled expansion. In other words, the expanded size of a compressed porous body 15 is generally known and may be chosen and optimized based upon the configuration of the fistula tract 10. Thus, use of a compressed porous body 15 may permit greater occlusion of the fistula tract 10 because the compressed porous bodies 15 conform to the tract 10, as opposed to making the tract 10 conform to the body of the device. The porous bodies 15 also may not require fluid to expand or to be maintained in an expanded state. Such controlled expansion porous bodies 15 may be formed of hyaluronic acid, hyaluronic acid mixed with collagen, or any other suitable materials that offer control or specific pore size or porosity.

In some embodiments, the controlled expansion of the bodies 15 may be a function of precompressing the bodies 15 a certain extent (e.g., approximately 80 percent of their non-compressed state) and then releasing the bodies 15 to resume their non-compressed state. Thus, it is possible to readily determine the final fully expanded condition of the bodies 15 because they may only expand to their non-compressed state upon being released to resume the non-compressed state.

As mentioned above with respect to FIG. 1A, the porous bodies 15 of the device 5 may be operably connected by a connecting member 20. The connecting member 20 may be a bioresorbable and biocompatible filament or string, for example. In certain embodiments, the connecting member 20 may also be a filamentous string, which enables the decoupling of the plurality of porous bodies 15 from the connecting member subsequent to implantation of the device 5 in the tract 10.

As shown above in FIGS. 1A and 1B, in some embodiments, the device 5 may include at least two porous bodies 15. The bodies 15 may be adapted and configured to work together to form the device's overall body 13 and separately to allow the device body 13 to conform to the tract 10 and fill all of the tract voids. In other words, the bodies 15 may be separate individual bodies joined together via the connecting member 20 along the length of the device 5, such that the resulting device body 13 has a segmented configuration. In certain embodiments, when the bodies 15 are in an expanded state or even in a non-expanded state, the spaced-apart distances D, D' may be zero, such that the proximal and distal ends 25, 30 of adjacent bodies 15 abut. In such an embodiment, the bodies 15 may appear to form a generally continuous porous device body 13 that is segmented by the interfaces of the adjacent proximal and distal ends 25, 30 of adjacent bodies 15. Thus, regardless of the magnitude of the spaced-apart distances D, D', in some embodiments, the device body 13 can be considered to be a chain or series of individual porous bodies 15 configured to work together and separately, resulting in an overall body 13 of the device 5 that is segmented and capable of conforming to the tract 10. It should be noted that the device 5 does not stent open the tract 10, but rather, the device 5, when in an expanded or non-compressed state, is capable of conforming to the tract 10.

In some embodiments, the device 5 may be configured to fill multi-tract fistulas. For example, the device 5 may comprise multiple device bodies 13 joined together at a common point of the device 5. In other words, the device may have at least two chains of porous bodies 15 joined together to allow a segmented device body 13 to be inserted into each of the tracts 10 of a multi-tract fistula. Alternatively, at least two chains of porous bodies 15 may be joined together to create a device 5 with at least two segmented device bodies 13.

In certain embodiments (not shown), the porous bodies 15 may also include attachment members that are configured to attach and engage the bodies 15 with the tract 10, and that deploy when the bodies 15 are in a non-compressed or expanded state. The attachment members may be unidirectional (e.g., comparable or similar to a fish hook barb) or may have a compressed fishbone-like structure and may be made of any appropriate biocompatible, resorbable material. The attachment members may permit outward removal but not inward traction. That is, when the attachment members are deployed, the bodies 15 may be retracted towards the proximal end without damaging the fistula tract 10, but the bodies 15 may be engaged with the tract 10 such that they will not migrate towards the distal end 12 of the tract 10.

As can be understood from FIG. 9B, in one embodiment, the device 5 may be deployed from the lumen of a delivery sheath or catheter 900 via a long, flexible rod or a "pusher" 903. The pusher 903 may be inserted through the delivery device 900 and may enable the clinician to push or otherwise direct the segmented device body 13 into the tract 10, thereby minimizing the dead space or void that may be left between the individual segments of the device body 13 or between the body 13 and tract 10. In some embodiments, the porous bodies 15 may not be connected via a connecting member 20, but instead may be multiple free bodies 15 that are inserted into the lumen of the sheath 900 for delivery into the tract. Thus, a pusher may enable the clinician to push or otherwise direct the unconnected bodies 15 into the fistula tract 10.

In certain embodiments, the bodies 15 of the fistula closure device 5 may be formed from materials other than a graft, wherein graft is defined as a transplant from animal or human tissue.

In some embodiments, the bodies 15 of the fistula closure device 5 may be formed from materials other than an extracellular matrix ("ECM") material, wherein ECM material is defined as decellularized organic tissue of human or animal origin. Furthermore, in some such embodiments, the bodies 15 of the fistula closure device 5 may be formed from materials other than those that are remodelable, where remodelable is defined as the ability of the material to become a part of the tissue. Instead, in some embodiments, the bodies 15 of the fistula closure device 5 may rely heavily on the amount of induced cross-linking that allows control of the resorption rate. Cross-linking essentially destroys the remodelable properties of a material. While remodelable may not exclude resorbable material completely, in some embodiments, the bodies 15 of the fistula closure device 5 may be formed of material that is completely resorbable and has no remodelable requirements or capabilities.

In some embodiments of the fistula closure device 5, the device body 13 may be formed of multiple bodies 15 to form a segmented body 13. The body 13 may include a distal occlusion member 200 (e.g., an umbrella-like member), the member 200 acting as an occlusion mechanism that is more of an occlusive cover rather than a plug or sealing member.

The fistula closure devices 5 as described herein may be implanted into a fistula tract 10 via various methods. For example, the fistula tract 10 may be visualized via direct visual inspection or medical imaging methods (e.g., Fluoroscopy, CT scan, MRI, etc.). A guidewire may be negotiated through the tract 10. The tract 10 may then be de-epithelializing irrigated. The device 5 may then be threaded over the guidewire and pushed into the tract 10. The distal fistula opening 12 may be occluded via elements of the device 5 (e.g., the most distal body 110 and/or expandable member 200). The device 5 may be trimmed to the length of the tract 10, after which the guidewire is removed. The device 5 and, more specifically, the device body 13, may be irrigated to cause expansion of the body 13. The device 5 may be anchored at the proximal fistula opening with a proximal end piece. For example, a retaining member may be connected to the distal end of the device 5 and secured to the region surrounding the proximal end opening of the tract 10, thereby creating tension in the device 5. The proximal fistula opening may then be covered with a dressing.

In another method of implanting the fistula closure device 5 in a fistula tract 10, a compressed porous scaffold 13 is placed in the fistula tract 10, wherein the scaffold 13 is at least partially inserted into the tract 10. The porous scaffold may be filled with, for example, an injectable polymer fluid, which may form an occlusive plug and may promote tissue growth and hence healing of the fistula tract. The method may further include fixating the device 5 in the tract 10 using a biocompatible connecting member 20, such as a string, which is attached to the device 5. The polymer injected into the tract 10 may be in a form that allows the foam to approximate the walls of the fistula tract 10 and fill any voids in the tract.

In another method of implanting the fistula closure device 5 in a fistula tract 10, a distal end 32 of the device 5 may be placed in such a way as to protect and occlude the distal end 12 of the fistula tract 10. The body 13 of the device 5 may be inserted into the fistula tract 10 in such a way as to at least partially fill the fistula tract 10. The surface load or point load dependent expansion of porous bodies 15 may then be activated within the fistula tract and the device 5 may be anchored in place at the distal and/or proximal ends 32, 31. For purposes of this disclosure, surface load or point load dependent expansion refers to the expansion of the porous bodies where, upon contact between the fistula tract wall (the "load") and a point on the porous body, that point of the porous body will stop expanding. The points on any or all of the rest of the porous body will continue to expand until the remaining points also make contact with the fistula tract wall. Thus, the surface load or point load dependent expansion of the bodies 15 of the device 5 disclosed herein allows the body 13 to generally fill and conform to the tract 10 without distorting the tract 10 or causing the tract to conform or deform due to the expansion of the body 13 in the tract. This ability of the body 13 can be a result of pre-compression of the body 13 and/or the nature of the material used.

Examples of materials from which to form the bodies 15 of the device 5 include: AngioSeal-like products, collagen sponge or other biomaterial materials as manufactured by Kensey Nash Corporation (Exton, Pa.); CollaPlug® or other collagen products as manufactured by Integra Corporation (Plainsboro, N.J.); and STAR® materials as manufactured by Healionics Corporation (Redmond, Wash.). With respect to the CollaPlug® material, in some embodiments, the CollaPlug® material may be compressed prior to delivery into the tract 10, the CollaPlug® material being approximately 90% porous. With respect to the STAR® materials, some such materials are known to have a specific pore size that promotes better angiogenesis. The STAR® materials and some of the materials and products discussed above may be capable of achieving a desirable controlled pore size and overall porosity for purposes of the devices and methods disclosed herein.

In another method of implanting the fistula closure device 5 in a fistula tract 10, the tract may be visualized and a guidewire may be routed into the tract. The tract 10 may be de-epithelialized and irrigated to remove any unwanted internal matter. The fistula closure device 5 may be tracked over the guidewire and the device 5 may then be received into the fistula tract until the distal end of the device 5 extends beyond the distal fistula opening 12. The device 5 may be expanded by irrigation so as to approximate the fistula tract 10. The device 5 may be trimmed if required. The method may include clipping or otherwise securing the proximal end of the device 10 at the proximal tract opening to provide a secure anchor. The proximal opening may then be covered with a dressing. In one embodiment, the segmented body 13 of the device 5, when in an expanded state, generally approximates the volume of the fistula tract with minimal distortion of the fistula tract.

Figure 13A:
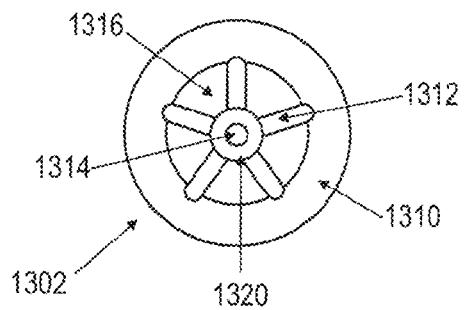
FIG. 13A is a superior view of an embodiment of a fistula closure device comprising a resilient annular collapsible distal end.
Figure 13B:
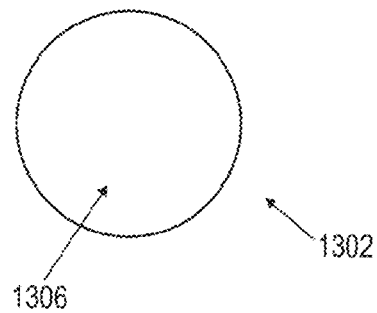
FIGS. 13B and 13C are inferior and side elevational views of the device in FIG. 13A.
Figure 13C:
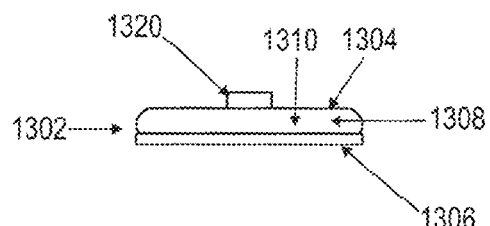

FIGS. 13A-13C depict another example of a fistula closure device, comprising a generally disc-shaped sealing body 1302 having a proximal surface 1304, a distal surface 1306 and an outer side wall 1308 therebetween. To facilitate sealing of the fistula tract, the proximal surface 1304 of the sealing body 1302 may comprise a seal 1310. In the depicted example, the seal 1310 is located along the peripheral edge of the sealing body 1302, but in other examples may be spaced away from the edge. The seal 1310 depicted in FIG. 13A comprises an annular configuration, but in other examples, the seal may have a polygonal, oval, star or square shape, for example, that may be the same or different shape as the sealing body 1302. The seal 1310 may be solid or may comprise a hollow interior. In some instances, a hollow interior may facilitate collapse of the sealing body 1302 for delivery, or facilitate deformation or conformation to the shape of a target location.

As further depicted in FIG. 13A, the sealing body 1302 may also comprise one or more ribs or support structures 1312. The number of support structures 1312 may be in the range of about one to about ten or more, from about two to about eight, about three to about six, or about five support structures, for example. The support structures 1312 may be evenly or symmetrically spaced apart in a radial configuration with respect to the center of the sealing body 1302 or a midline of the sealing body 1302. The support structures 1312 may also be solid or hollow. In some examples comprising at least one hollow support structure 1312 and a seal 1310 that is at least partially hollow, the support structure 1312 and the seal 1310 may be in fluid communication through an access lumen 1314 provided on the sealing body 1302. The access lumen 1314 may permit injection or filling of materials into the body 1302, including but not limited to contrast agents (e.g. barium, contrast saline, etc.) or a bulking material such a silicone. The distal surface 1306 may be generally smooth, which may facilitate passage of materials through the gastrointestinal tract past the implanted sealing body 1302, but in other examples may comprises one or more recesses, openings and/or projections. The proximal surface 1304 may comprise recesses 1316 located between the support structures 1312 and/or the annular seal 1310. In some embodiments, the recesses may reduce the degree of surface contact between the sealing body 1302 and the surrounding tissue, thereby shifting sealing forces along the annular seal 1310.

The sealing body 1302 may further comprise an attachment structure 1320 to facilitate delivery of the sealing body 1302. The delivery catheter, if any, may releasably engage the sealing body 1302 at the attachment structure 1320. The attachment structure 1320 may also be the attachment site for one or more tethers or sutures that may be used in conjunction with the sealing body 1302. In some further examples, the attachment structure 1320 may be located centrally with respect to the overall shape of the sealing body 1302, but in other examples the attachment structure 1320 may be eccentrically located. The attachment structure 1320 may be integrally formed with the access lumen 1314, or may be separate from the access lumen, which may be used to inject materials into the hollow lumens and/or cavities of the support structures 1312 and the annular seal 1310, if any. In other examples, through lumens in the body may permit access to the intestinal lumen for fluid sampling, placement of sensors, and/or therapeutic agent delivery.

Figure 14:
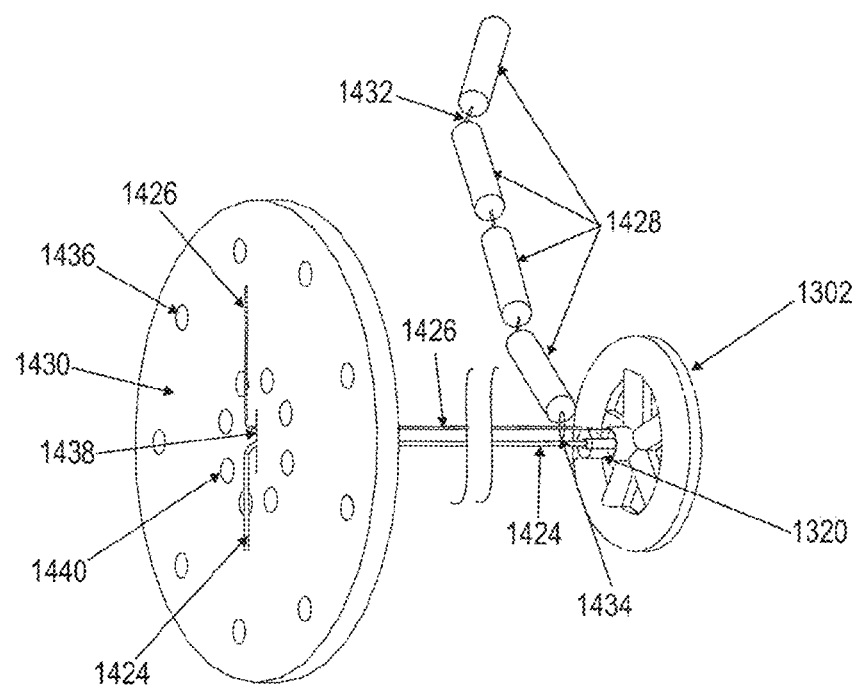
FIG. 14 is a schematic representation of the device in FIGS. 13A-13C used with a proximal retaining structure and a plurality of tethered, expandable members attached to the device.

Referring to FIG. 14, the sealing body 1302 may be a distal portion of a fistula closure device. In use, the sealing body 1302 may seal the fistula tract by tensioning the sealing body 1302 against the intestinal wall of a patient though one or more tethers 1424 and 1426 attached to the sealing body 1302. The tethers 1424 and 1426 may be attached at the attachment structure 1320 or other location of the sealing body 1302, including but not limited to the annular seal 1310 and/or the support structures 1312. The multiple tethers 1424 and 1426 may be color coded to distinguish the various tethers during the implantation procedure. At least one of the tethers 1424 may be used to apply tension to the sealing body 1302 and seal the fistula tract. In some examples, a second tether 1426 may be provided to as a guide element for delivery of the expandable members. In some embodiments, providing separate tethers 1424 and 1426 may reduce the risk of free-floating or unsecured expandable members 1428 should the tensioning tether 1424 rupture. FIG. 14, for example, depicts the second tether 1426 that may be used to deploy one or more expandable members 1428 along the fistula tract. At least one or both of the tethers 1424 and 1426 may be secured using a proximal restraining structure 1430 that resists distal sliding or displacement of the tether 1424 and/or 1426 by providing an increased surface area or transverse dimension that resists collapse or entry of the restraining structure 1430 into the fistula tract.

It should be understood that features and characteristics described herein with reference to specific expandable members 200 and sealing bodies 1302 may be applied to any of the other expandable members and sealing bodies described herein, as appropriate.

As shown in FIG. 14, the expandable members 1428 may comprise generally elongate collagen plugs (or other biocompatible material) that are configured to expand, fill and conform to surrounding tissue structures. The plugs may have a generally cylindrical shape, but in alternative examples may have any of a variety of shapes, including spheres, rectangular blocks, conical or frusto-conical shapes, and the like. Not all of the plugs need to have the same size, shape, orientation and/or symmetry. As further illustrated in FIG. 14, the expandable members 1428 may be interconnected by a plug suture or tether 1432. The plug tether 1432 may form a loop structure 1434 at one end of the plurality of expandable member 1428 that may facilitate delivery of the expandable members 1428 along at least one of the tethers 1426. The expandable members 1428 may be slidably attached or fixedly attached to the plug tether 1432 by a resistance interfit, but in other examples, one or more expandable members 1428 may have an enlarged tether lumen to facilitate sliding or other relative movement with respect to the plug tether 1432. In still other examples, one or more expandable members 1428 may be glued to the tether, or the plug tether 1432 may have a cross-over configuration or stitching through the expandable member to resist relative movement or separation of the expandable member. For example, in some, all or at least the distalmost or free-floating expandable member, the plug tether 1432 may be fixedly attached using any of a variety of attachment interfaces described above. In some further examples, the plug tether 1432 may further comprise one or more knots or other fixedly attached structures along its length to limit sliding or movement of an expandable member to a particular range.

In one exemplary delivery procedure, the fistula tract and surrounding area may be prepped and draped in the usual sterile fashion. Anesthesia may be achieved as needed using topical and/or injectable anesthetics. The fistula tract may then be irrigated with sterile saline, hydrogen peroxide or any other suitable biocompatible irrigation fluid. In some further examples, portions of the fistula tract may be de-epithelialized using silver nitrate sticks, cautery and/or mechanical debridement using a scalpel, for example. The delivery instrument may be removed from its aseptic packaging and placed onto a sterile field. To reduce the risk of dislodging the sealing body 1302, tensioning of the attached sutures 1424 and 1426 may or may not contraindicated. Various extension tubes and stopcocks, if any, may be attached to the delivery instrument 1550 at this time. Flushing, patency/leakage testing of the delivery instrument connections may be performed using saline or similar fluid. The integrity of the sealing body 1302 may also be assessed using saline, contrast agent or a mixture of both and the application of positive and/or negative fluid pressure through the delivery instrument 1550. Prior to delivery, the sealing body 1302 may be evacuated with negative pressure to collapse the sealing body 1302. The same or a separate syringe of saline, contrast agent or combined fluid may be prepared as an inflation syringe for the sealing body.

The fistula tract may be traversed using a guidewire, with or without the assistance of imaging modalities such as plain X-ray, fluoroscopy, CT scanning, endoscopy, or ultrasound, for example. The peel-away sheath may be passed over the guidewire and through the dermal ostium of the fistula tract. A dilator may be used as needed to prepare the fistula tract for passage of the delivery instrument and/or endoscopic instrument. The position of the sheath may be verified with the same or different imaging modality. The procedure may be continued once the desired sheath tip location is achieved or verified, e.g. the distal tip is located beyond the intestinal or central ostium of the fistula tract. The guidewire (and dilator, if any) may then be removed. The sheath may be flushed with sterile saline. The collapsed sealing body 1302 may be wrapped around the distal end of the delivery instrument 1550 by rolling, rather than collapsing the sealing body 1302 like an umbrella. The delivery instrument 1550 may be inserted into the sheath and advanced until the sealing body 1302 is located beyond the distal tip of the sheath. The relative location of the delivery instrument 1550 may be evaluated by imaging, by the distance between proximal ends of the sheath and delivery instrument, and/or by the loss of insertion resistance that may be tactilely felt once the sealing body 1302 has exited the sheath. A 10 cc syringe, for example, may be attached to the delivery instrument and negative pressure may be applied to the sealing body 1302 through one of the stopcocks, which then may be closed to maintain the sealing body 1302 in a collapsed state. The syringe may then be removed and is replaced with a syringe of the same or smaller size. The stopcock is re-opened and the evacuation of the sealing body 1302 may be confirmed by pulling back on the syringe and assessing plunger displacement. A portion of the fluid in the syringe (e.g. 0.5 cc) may then be injected into the sealing body 1302 to inflate it. The stopcock may be closed to maintain the inflation.

While maintaining the position of the delivery catheter (or the Touhy Borst valve), gentle traction may be applied to the tension tether attached to the sealing body 1302 to fully seat the sealing body 1302 to the delivery instrument 1550. The Touhy Borst valve may then be loosened and the sheath may be partially retracted into the fistula tract (e.g., proximal to the central ostium). The sealing body 1302 may then be deployed by disengaging or otherwise separating the lock mechanism between the Touhy Borst valve 1562 and the connector 1556. The remaining distal portions of the delivery instrument 1550 may then be slowly withdrawn from the fistula tract. While maintaining slight tension on the tension tether 1424 to hold the sealing body 1302 against the central ostium of the fistula tract, the sheath may be slid proximal the desired length that is to be filled with the expandable members. Slight tension may be maintained on the tension tether 1424 through the remaining procedure until the tether is anchored to the skin.

The actuator 1572 may be inserted into the plug delivery catheter 1570 until the suture loop 1434 just exits the distal end 1578 of the catheter 1570. The actuator 1572 may then be withdrawn. While maintaining slight tension on the tension tether 1424, the delivery tether 1426 may be threaded through the loop 1434 at the distal end 1578 of the delivery catheter 1570. The catheter 1570 may then be advanced over the delivery tether 1426 until the catheter tip 1578 is located at the desired delivery location. The actuator 1572 may be reinserted into the catheter 1570 until the distal end 1574 of the actuator 1572 contacts the most proximal expandable member 1428 in the catheter 1570. The position of the actuator 1572 may then be maintained while the delivery catheter 1570 is retracted to deploy the distalmost expandable member 1428. The catheter 1570 may or may not be relocated to deploy the remaining expandable members 1428. Once deployment of all the expandable members 1428 is completed, the Luer fittings on the proximal end 1576 of the delivery catheter 1570 and actuator 1572 may be engaged and the catheter 1570 and actuator 1572 may be removed from the sheath. Saline may be optionally infused through the sheath to facilitate expansion of the expandable members 1428. Using separately supplied catheters 1570 and actuators 1572, additional expandable members may be deployed using the above procedure to fill the fistula to the desired level. Sealing body 1302 placement may be reconfirmed by imaging techniques to ensure that the sealing body 1302 is located against the central ostium.

While maintaining tension on the tension tether 1424, the restraining structure 1430 may be separated from the sheath and the sheath may be removed from the fistula tract. While continuing to maintain slight tension on the tension tether 1424 through the restraining structure 1430, the delivery tether 1426 may be sutured or otherwise attached to the surrounding tissue using a free needle passed through the restraining structure and tied to the tissue with the desired tension. At a location opposing the delivery tether 1426 on the restraining structure 1430, a free needle may be used pass through the restraining structure 1430 and to suture the tension tether 1424 to the surrounding tissue. Additional sutures (e.g., 3-0 or 4-0 nylon) may be used to further secure the restraining structure 1430 to the surrounding superficial tissue as needed. Final imaging confirmation of the sealing body 1302 placement along the central ostium may be performed at this point using the imaging modalities as previously described, but also including double-contrast x-ray studies and colonoscopy/enteroscopy. An absorbent dressing may be securely on top of the restraining structure 1430 to absorb any excess drainage that may occur. Alternatively active drainage of the fistula/wound may be performed using wound drainage products or negative pressure wound therapy products. Prophylactic antibiotics may be optionally provided post-procedure.

The size and shape of the restraining structure 1430 may be different depending upon the particular fistula being treated, but in some examples, the restraining structure 1430 may have a diameter or maximum transverse dimension that is at least the same as the sealing body 1302. In further examples, the diameter or maximum transverse dimension may be at least two times, three times, or four times or greater than the corresponding dimension of the sealing body 1302. The restraining structure 1430 may also comprise one or more securing apertures 1436 that may permit the attachment of the restraining structure 1430 to the skin or a bandage surrounding the dermal fistula opening. These securing apertures 1436 may be spaced around the periphery of the restraining structure 1430, closer to the outer edge rather than the center of the restraining structure 1430. In other examples, the restraining structure 1430 may comprise an adhesive surface that contacts the skin surrounding the fistula and resists movement. The tethers 1424 and 1426 of the device may be secured to the restraining structure 1430 by any of a variety of mechanisms, including a clamping structure, adhesive, or by a deformable slit 1438 that provides a releasable friction fit interface for the tethers 1424 and 1426. The attachment site of the tethers 1424 and 1426 on the restraining structure 1430 may further comprise access openings 1440 that may be used to infuse therapeutic agents into the fistula, and/or to permit passive or active fistula drainage, or the application of negative pressure therapy to the fistula. FIG. 15A depicts the restraining structure 1430 without the attached tethers.

Referring to FIG. 15B, positioning of the sealing body 1302 and tethers 1424 and 1426 may be performed using a delivery instrument 1550 that comprises an elongate tubular element 1552 that is configured with a distal end 1554 that releasably attaches to the attachment structure 1320 of the sealing body 1302. The interface between the attachment structure 1320 and the tubular element 1552 may comprise a resistance interfit, but may alternatively comprise a mechanical interlocking fit such as a helical threaded interface, for example. In some embodiments, attachment of the sealing body 1302 to the tubular element 1552 may also be provided by tensioning the tether 1424 that passes through the tubular element 1552 and other portions of the delivery instrument 1550. To prepare the sealing body 1302 for delivery, the sealing body 1302 may be collapsed or compressed around the distal end 1554 of the tubular element 1552 and held in that configuration using a cannula or introducer. In some examples, applying suction or a vacuum may facilitate collapse of the sealing body 1302. Although delivery of the sealing body 1302 may be performed through the fistula tract and toward the gastrointestinal site, in other examples, the cannula or introducer may be configured to pierce tissue so that delivery instrument 1550 may be used to deliver the sealing body 1302 and at least one tether 1424 along a secondary tract other than the fistula tract. This secondary tract may be a pre-existing tract or a tract formed by the insertion delivery instrument.

As shown in FIG. 15B, other features of the delivery instrument 1550 may include one or more connectors 1556, 1564 that permit the attachment or use of access lines 1558 and stopcocks 1560, 1566, for example, which may facilitate the aspiration or infusion of materials, or the insertion of endoscopic tools or sensors during the delivery procedure. The delivery instrument 1550 may include a hemostasis valve 1562 or other fluid-sealed interface that permits passage of items such as the tether 1424 while resisting fluid leakage.

The expandable members 1428 may be provided in a rigid or flexible tubular catheter 1570, as depicted in FIG. 15D. To expel or release the expandable members 1428, a push element or actuator 1572, depicted in FIG. 15C, may be used to serially release the expandable members 1428 from the distal end 1578 of the catheter 1570. This may be performed by pushing the distal tip 1574 of the actuator 1572 through the proximal end 1576 of the catheter 1570 while holding the catheter 1570 in place, or by holding the actuator 1572 in place while withdrawing the catheter 1570, for example.

To perform the procedures described above, a kit may be provided that contains the delivery instrument 1550 along with the sealing body 1302 and attached tethers 1424 and 1426. The sealing body 1302 and attached tethers 1424 and 1426 may be coupled to the instrument 1550 at the point-of-manufacture or at the point-of-use, and therefore may be provided in the kit either pre-attached or separate from the instrument 1550. The kit may also comprise an actuator pre-filled catheter 1570 with one or more expandable members 1428 that are pre-attached with a plug tether 1430. Additional catheters 1570 with expandable members 1428 may be also be packaged and provided separately. In further examples, the kit may also contain one or more other items, including but not limited to a guidewire (e.g. 0.038" guidewire), a peel-away sheath (e.g. 7F, 8F, 9F, 10F, or 12F sheath), one or more syringes (e.g. 0.5 cc, 1 cc, 5 cc, and/or 10 cc syringes), saline or biocompatible fluid, contrast media, a scalpel, one or more free needles, and non-resorbable sutures (e.g. 3-0 or 4-0 nylon suture) that may be used to attach the restraining structure 1430 to the adjacent skin or to a bandage. A fistula tract dilator may also be provided in the kit.

Fistula treatment devices described herein may in some cases be provided in a kit. The kit may also include any other appropriate devices or components, such as delivery tools or other fistula treatment devices (i.e., a kit may include multiple fistula treatment devices). The contents of a kit may be provided in sterile packages. Instructions may be provided on or with the kit, or alternatively via the internet or another indirect method, and may provide direction on how to employ the kit (e.g., outlining a deployment method such as one of those described herein).

Figure 8:
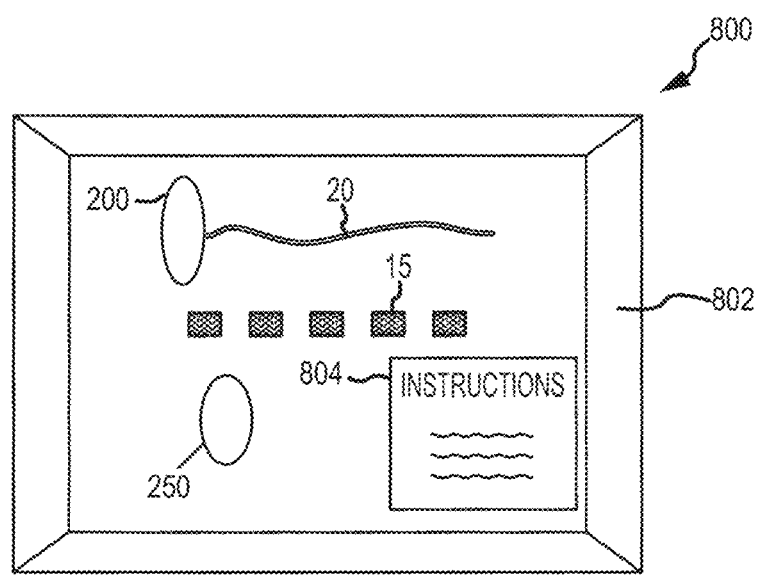
FIG. 8 shows an embodiment of a fistula treatment kit.

FIG. 8 depicts an exemplary kit 800. As shown there, the various components of the fistula closure device 5 are provided in a sterile package 802. For example, the sterile package 802 may contain the connecting member 20, the expandable member or distal anchor 200, the proximal anchor 250, and individual porous bodies 15 for threading over the connecting member 20. Instructions 804, which may be provided on or with the kit 800, or alternatively via the internet or another indirect method, provide direction on how to employ the kit. The instructions may, for example, outline a deployment method similar to those described above. It should be understood that the concept of kits may readily be applied to any of the devices and device components disclosed herein, as appropriate.

Figure 16B:
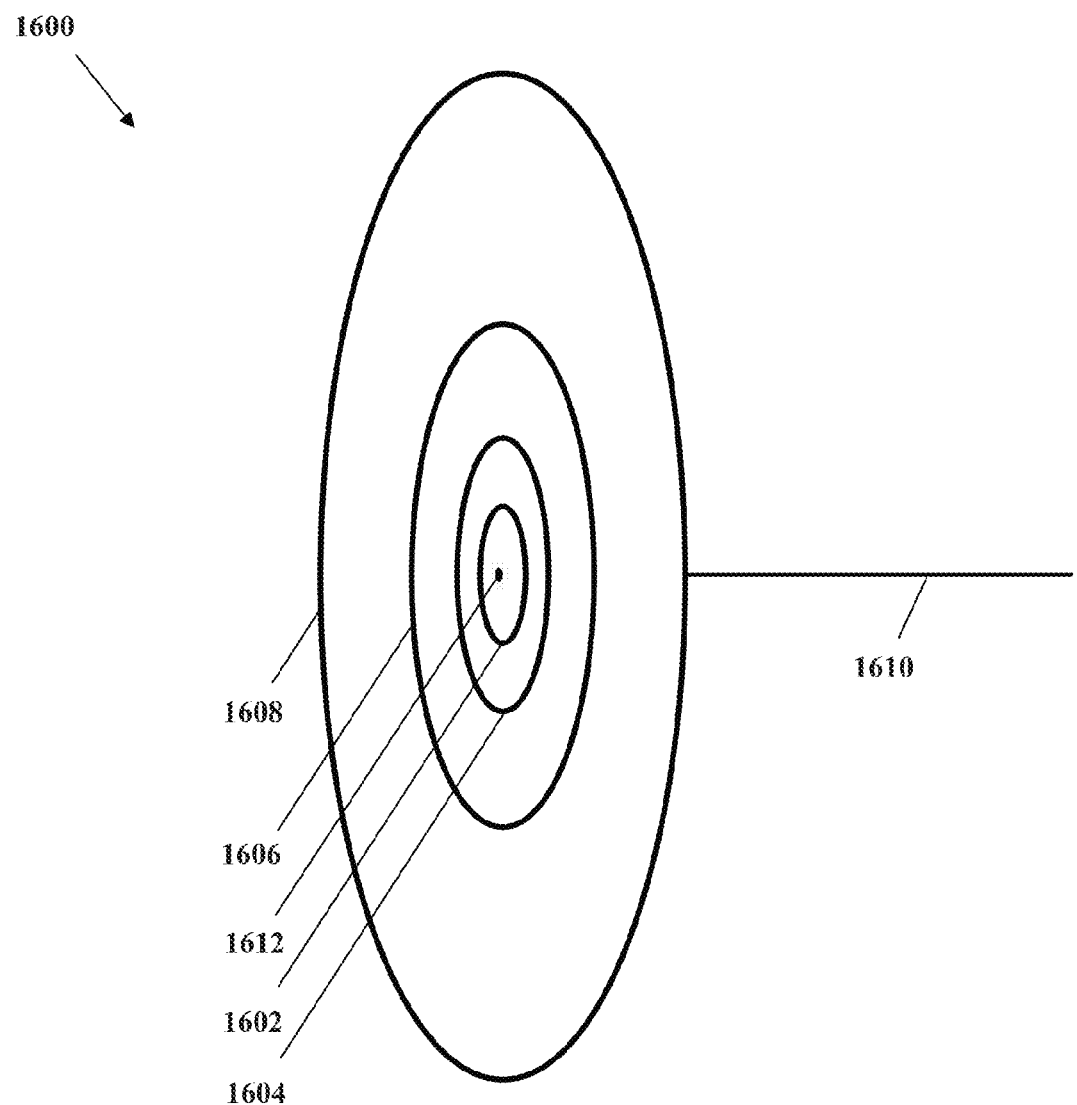

FIGS. 16A and 16B depict another example of a distal anchor 1600 for occluding a distal opening of fistula tract. As depicted therein, distal anchor 1600 may comprise a plurality of foldable members 1602, 1604, 1606, and 1608 threaded on a suture 1610. FIGS. 16A and 16B illustrate, respectively, an expanded and a restrained configuration of distal anchor 1600. The expanded configuration illustrated in FIG. 16A may represent the configuration of the distal anchor 1600 when it has been released from an insertion device into a body lumen. The restrained configuration illustrated in FIG. 16B may represent the configuration of the distal anchor when a restraining force is exerted on the distal anchor 1600 by tensioning the suture 1610 while the distal anchor 1600 is positioned over a distal opening of a fistula tract. As can be appreciated by comparing FIGS. 16A and 16B, flexible members 1604, 1606, and 1608 are configured to slide along suture 1610. Proximal-most foldable member 1608 may be further configured to occlude a distal opening of the fistula tract. Distal-most foldable member 1602 may be configured to reduce or prevent rupturing at the center of foldable member 1608 when the suture 1610 is tensioned during positioning of the distal anchor 1600. Distal-most foldable member 1602 may be configured to a size and shape that distributes the force exerted by the suture over a wider area—the area of contact between foldable member 1602 and the next foldable member, first inner foldable member 1604. In this way, pressure exerted on foldable member 1608 by tensioning suture 1610 can be reduced. Inner foldable members 1604 and 1606 may also serve to reduce or prevent rupturing of the proximal-most foldable member 1608 by further distributing the force exerted on foldable member 1608. Distal-most foldable member 1602 may also comprise a suture attachment structure 1612 for attaching suture 1610.

Each foldable member comprises a large dimension (diameter) and a small dimension (thickness). In some variations, the diameter is considerably larger than the thickness. For example, the foldable members of distal anchor 1600 comprise a very large diameter relative to their thickness so that the foldable members take on a "pancake" appearance. In some variations, the small dimension of the foldable members are characterized as percentages of the large dimension, and may sometimes be less than or equal to 1%, 2%, 3%, 4%, 5%, 6%, 7%, 8%, 9%, 10%, 15%, 20%, 30%, 40% or 50%, or any percentage range between any two of the above percentages. The foldable members are configured so that the large dimension is oriented generally in parallel to a surface of a body lumen when the foldable members are deployed.

In some variations, the foldable members may reduce in diameter from the proximal-most foldable member 1608 to the distal-most foldable member 1602. The diameter of the distal-most foldable member may be characterized as a percentage from 1% to 100% of the diameter of the proximal-most foldable member 1602, and may sometimes be about 5%, 10%, 20%, 25%, 30%, 35%, 40%, 45%, 50%, 55%, 60%, 65%, 70%, 75%, 80%, 85%, 90%, or 95%, or any percentage range between any two of the above percentages. In other variations, the diameter difference may be approximately equal to a percentage between any of the foregoing percentages. The diameters of the inner foldable members 1604 and 1606 may also be characterized as a percentage from 1% to 100% of the diameter of the proximal-most foldable member

1602, and may sometimes be about 5%, 10%, 20%, 25%, 30%, 35%, 40%, 45%, 50%, 55%, 60%, 65%, 70%, 75%, 80%, 85%, 90%, or 95%, or any percentage range between any two of the above percentages. In other variations, the diameter difference may be approximately equal to a percentage between any of the foregoing percentages. In some variations, the diameter of the proximal-most foldable member may be sized to occlude a distal opening of a fistula tract. In some variations, the diameter of the proximal-most foldable member may be in the range of about 4 mm to about 50 mm, sometimes about 8 mm to about 30 mm, and other times about 10 mm to about 45 mm, and still other times about 12 mm to about 30 mm. Further, although four foldable members are illustrated in FIGS. 16A and 16B, other variations may include any number of foldable members, including 2, 3, 5, 6, 7, 8, 9, 10 foldable members.

In some variations, one or more of the foldable members are non-circular. A non-circular outline can be understood to be any shape in which the perimeter is not a constant radius from a center point. Non-circular shapes include shapes with first-derivative discontinuities at one or more locations. Non-circular shapes may also be Non-circular shapes may also be Non-circular shapes a generally circular shape with protrusions or recesses on the perimeter to accommodate a predetermined surface of a body lumen. Non-circular shapes may include, but are not limited to, ovals, ellipses, rectangles, lenses, deltoids, and bell-shapes. When non-circular, a diameter of a foldable member may be understood to mean a length of the member in one dimension. For example, a line taken through a center point or a widest span of the member. In such variations, the diameters of the distal-most and inner foldable members may be characterized as a percentage from 1% to 100% of the diameter of the proximal-most foldable member, and may sometimes be about 5%, 10%, 20%, 25%, 30%, 35%, 40%, 45%, 50%, 55%, 60%, 65%, 70%, 75%, 80%, 85%, 90%, or 95%, or any percentage range between any two of the above percentages. In some variations, some of the foldable members take a shape different from one or more of the other foldable members. For example the distal members may be circular, but the proximal-most foldable member may be shaped to occlude a non-circular fistula opening. In some other variations, the distal foldable members are also non-circular in order to achieve a desired distribution of forces, for example.

Suture attachment structure 1612 is illustrated on a distal surface of foldable member 1602, but in some variations is positioned on a proximal surface of distal-most foldable member 1602. When on the distal surface, the suture attachment structure may comprise an aperture to allow the suture to pass through the foldable member and an additional feature to fixedly couple the suture to the foldable member. When positioned on the proximal surface, the suture attachment structure may include a loop or other feature to fixedly couple the suture to the foldable member. In some variations, the suture attachment structure includes a recess on the distal surface of the distal-most foldable member 1602. Distal-most foldable member 1602 may also comprise reinforcing structure (not shown) for the suture attachment structure 1612. In some variations, the reinforcing structure is a wire mesh embedded within distal-most foldable member 1602 and configured to distribute the force resulting from tensioning the suture across all or some of the distal-most foldable member 1602. In other variations, the reinforcing structure might include a button-shaped suture attachment structure, wherein the expanded areas of the button-shaped suture attachment structure serve to distribute the force over a wider area.

In some variations, the foldable members 1604, 1606, and 1608 may include apertures (not shown) to permit the members to slide along suture 1610. Although illustrated in FIGS. 16A and 16B as passing through the center of the foldable members, in some variations the suture does not pass through the centers of one or more foldable members. For example, when the surface of a distal opening of a fistula tract does not lie in a plane orthogonal to the axis of the fistula tract, tensioning of the suture may cause an unequal distribution of force on the proximal-most disk. In such a scenario, the apertures may be off-center to redistribute the forces to provide an even, reduced pressure on the proximal-most foldable member. In some variations, the apertures may be reinforced by a ring or grommet. The reinforcement structure, if any, may be fully embedded with the foldable member, or may be partially exposed on either the distal and/or proximal surface of the member. In some further variations, the reinforcement structure may also comprise an interlocking structure to interlock with a complementary interlocking structure of the reinforcement structure of an adjacent foldable member. Other examples of inter-member locking features are described below.

As described above, the foldable members 1602, 1604, 1606, and 1608 are configured to be released from an insertion device. In some variations, the foldable members are configured to be reduced in size to fit within an insertion rod of a given diameter. For example, one or more of the foldable members may be configured to reduce its cross-sectional profile by folding or rolling, thereby facilitating entry into the insertion rod, as described in more detail later. In some variations, the flexibility of the foldable members may be increased as the diameters increase to facilitate folding or rolling of the foldable members to a predetermined cross-sectional profile for insertion. In some variations, a flexibility of a foldable member may be characterized by a thickness of the foldable member. In some variations, a flexibility of the foldable members may be characterized by its percentage thickness, from 1% to 100%, of the thickness of the distal-most foldable member, and may sometimes be about 5%, 10%, 20%, 25%, 30%, 35%, 40%, 45%, 50%, 55%, 60%, 65%, 70%, 75%, 80%, 85%, 90%, or 95%, or any percentage range between any two of the above percentages. In some variations, a flexibility of the foldable members may be characterized by its percentage density, from 1% to 100%, of the density of the distal-most foldable member, and may sometimes be about 5%, 10%, 20%, 25%, 30%, 35%, 40%, 45%, 50%, 55%, 60%, 65%, 70%, 75%, 80%, 85%, 90%, or 95%, or any range between any of the two percentages. In some variations, a flexibility of the foldable members may be characterized by its percentage coefficient of resistance to deformation, from 1% to 100%, of the coefficient of resistance to deformation of the distal-most foldable member, and may sometimes be about 5%, 10%, 20%, 30%, 40%, 50%, 60%, 70%, 80%, 90%, or 95%, or any percentage range between any two of the above percentages. In some variations, the flexibility of a foldable member may be constant across the member. In other variations, the flexibility of a foldable member may vary across the member by, for example, a variance in the density and/or thickness in different regions of the foldable member. This flexibility variance may be controlled to facilitate folding the member or to facilitate coupling two foldable members.

Figure 17A:
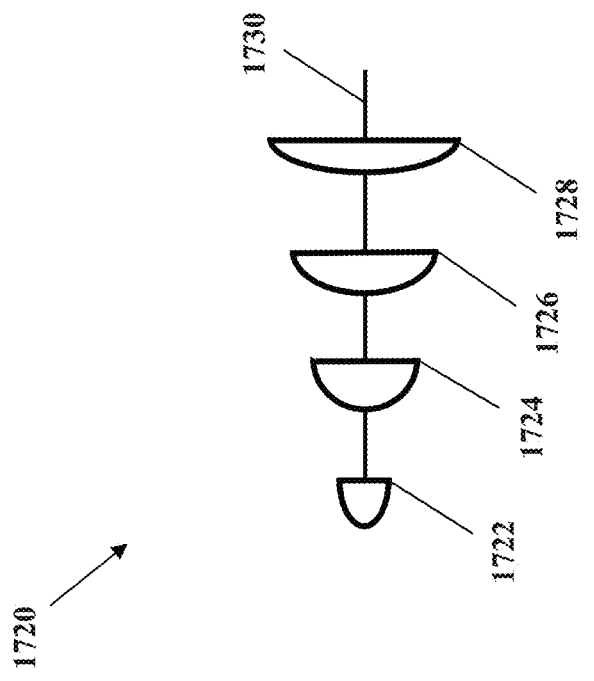
FIGS. 17A and 17B illustrate various embodiments of multi-disc anchor configurations.
Figure 17B:
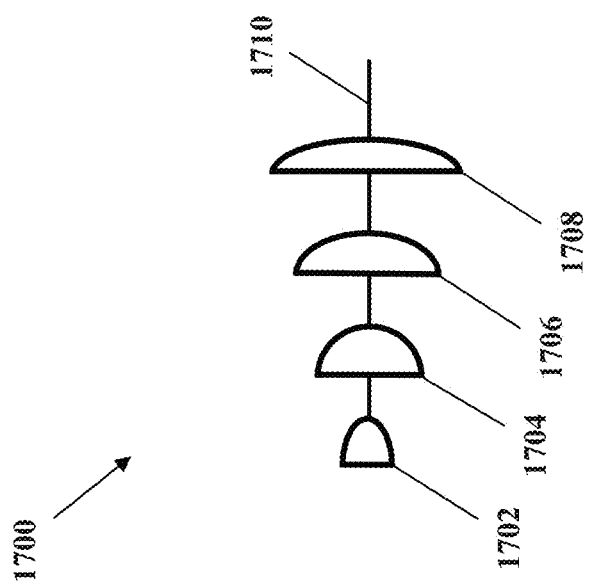

Foldable members 1602, 1604, 1606, and 1608 are depicted in FIGS. 16A and 16B as generally planar. In some variations, the foldable members are non-planar. For example, the foldable members may be generally concave. A concave geometry may advantageously distribute pressure in a predetermined field when the foldable members are fully restrained. A generally concave shape may also reduce the propensity of the distal anchor to pucker and result in a central region of the distal anchor lying proximal to an outer region when the distal anchor is in the deployed configuration. When the distal anchor is in the deployed configuration, a relatively large quantity of pressure may focus in the central region of the distal anchor, possibly resulting in a structural fracturing of the distal anchor at the central region. A concave geometry may also advantageously limit the distal anchor's re-entry into the fistula tract as a result of puckering, that is, may limit the propensity of a central region of the distal anchor to lie proximal to an outer region when the distal anchor is fully restrained. The generally concave geometry of the foldable members may be characterized by a cross-sectional curve with a zero first derivative when the foldable member is rotated 90 degrees clockwise (that is, when the foldable member is turned on its side). When rotated back 90 degrees anti-clockwise, the zero first derivative may be located at a proximal-most or distal-most point of the curve. FIGS. 17A and 17B illustrate side views of two exemplary sets 1700 and 1720, respectively, of generally concave foldable members with zero first derivatives at the proximal-most and distal-most points of the curve, respectively. FIG. 17A depicts a side-view of a set 1700 of foldable members 1702, 1704, 1706, and 1708 with zero first derivatives located at the proximal-most point of the curves, that is, the geometry of the cross-sections of the foldable members forms a reverse "C." Foldable members 1702, 1704, 1706, and 1708 are slidably connected by suture 1710. FIG. 17B depicts a side-view of a set 1720 of foldable members 1722, 1724, 1726, and 1728 with zero-derivatives located at the distal-most point of the curves, that is, the geometry of the cross-section foldable members forms a "C." Foldable members 1722, 1724, 1726, and 1728 are slidably connected by suture 1730. Although each foldable member depicted in FIGS. 17A and 17B comprises a constant radius of curvature, some variations may include one or more foldable members with a non-constant radius of curvature. Such shapes may include, but are not limited to, a bell, a cone, a mushroom head, or a box. In some variations, the geometry of a foldable member may be characterized as a 180 degree revolution of a curve about a line through a point of zero first derivative. For example, the geometries illustrated in FIGS. 17A and 17B may be generated by rotating an arc of fixed radius about its minimum point of zero first derivative. In other variations, the geometry may be defined by rotating a parabolic curve about a point of zero first derivative, wherein a parabolic curve is defined by the equation $y=Cx^2$, where (x, y) comprise a range in a Cartesian plane and C is any real, non-zero number. In other variations, the geometry may be defined by a rotating the two-dimensional polynomial equation $y=\Sigma a_n x^n$, where (x, y) comprise a range in a Cartesian plane, $a_n$ is any real number, and n is any integer.

Although the geometries described above are generated by a single curve defining both the distal and proximal surface of each foldable member—that is, the foldable member has a constant thickness—other variations may have different curves to respectively define the proximal and distal surfaces. Further, although the curves above are discussed with respect to an (x,y) Cartesian plane, it should be understood that the cross-section of the foldable member may not be positioned in a fistula tract so that the curve remains in that orientation. For example, although a cross-sectional area of a foldable member may be described in (x,y) coordinates so that its first derivatives are at the top or bottom of a curve, in some variations, the foldable member is rotated for insertion so that the minimum point is now at a vertical mid-point.

Further, the curves and shapes described above refer to a general or overall shape of a foldable member, the foldable members may have additional surfaces features. For example, a foldable member's overall shape may be augmented with any of the recesses, protrusions, and coupling members described herein.

As depicted in FIGS. 17A and 17B, the relative curvature of the foldable members increases from the proximal-most foldable member to the distal-most foldable member, that is, the radius of curvature decreases from the proximal-most foldable member to the distal-most foldable member. In some variations, the radius of curvature of the distal-most foldable member and inner foldable members may be characterized as a percentage, from 1% to 100%, of the radius of curvature of the proximal-most foldable member, and may sometimes be about 5%, 10%, 20%, 30%, 40%, 50%, 60%, 70%, 80%, 90%, or 95%, or any percentage range between any two of the above percentages. In some variations, the curvature decreases from the proximal-most foldable member to the distal-most foldable member, that is, the radius of curvature increases from the proximal-most foldable member to the distal-most foldable member. In some variations, the radius of curvature of the proximal-most foldable member and inner foldable members may be characterized as a percentage, from 1% to 100%, of the radius of curvature of the distal-most foldable member, and may sometimes be about 5%, 10%, 20%, 30%, 40%, 50%, 60%, 70%, 80%, 90%, or 95%, or any percentage range between any two of the above percentages. In other variations, the curvature of the members may be constant. A variation in curvature among the foldable members may be determined to account for a variation in flexibility among the foldable members. For example, a less flexible member may be more likely to resist deformation when fully restrained and so less curvature may be necessary. A variation in curvature among the foldable members may also be determined to account for a variation in pressure exerted on the foldable members in the restrained configured and its effect on each foldable member's relative deformation. For example, a more distal foldable member is likely to deform more due to the pressure being exerted more directly on that member. In some variations, the unrestrained curvature of each foldable member may be determined to generate a predetermined shape of the distal anchor in the restrained configuration. That is, the curvature of the unrestrained foldable members may be determined so that a predetermined shape is achieved once all the foldable members are restrained and coupled to each other. In some variations, the predetermined shape is planar. In others, the predetermined shape is non-planar. In some variations, the curve may be a bell-shape curve so that the revolved curve may include outside edges with a lower curvature than a central region. In other variations, the curve may include outside edges with a higher curvature than a central region. Also, although the exemplary embodiments depicted herein comprise multi-member distal anchors that generally comprise a reduced member size from proximal to distal, in other variations, the members may be generally of the same size, and may or may not vary in curvature from proximal to distal, as described above.

Returning to FIGS. 16A and 16B, foldable members 1602, 1604, 1606, and 1608 are depicted as being generally smooth on their distal faces. In some variations, one or more foldable members include additional features to restrict relative movement of the foldable members in a direction generally transverse to the direction of the force exerted by the suture. In some variations, movement is restricted by surface features on one or more foldable members that fixedly couple the one or more foldable members to adjacent foldable members. In other variations, a pair of adjacent foldable members include electromagnetic elements that produce attractive electromagnetic forces, such as opposing magnetic poles, that fixedly couple the adjacent foldable members. In other variations, an adhesive may be used to fixedly couple the one or more foldable members to adjacent foldable members. For example, one surface of a foldable member may include an adhesive or complementary interconnecting structures, including but not limited to hook-and-loop attachment structures. In some variations, one surface of a foldable member may comprise a curing agent. In yet further variations, the curing agent may be enclosed in one or more capsules, where the capsule is configured to rupture open exposure to an agent included on the opposing surface of the adjacent foldable member. In other variations, the capsule may rupture as a result of the pressure exerted when the distal anchor is restrained by a suture.

In some variations, the proximal surface of the proximal-most foldable member may be structured to facilitate a secure and lasting coupling of the distal anchor to the surface of a body lumen. In some variations, the structure may be a grapple, as described herein. In some variations, an adhesive may be added to the proximal surface of the proximal-most member. The adhesive may be applied by a physician before inserting the proximal-most foldable member into the body lumen or applied after insertion. In other variations, the adhesive may be applied during a manufacturing process and covered with a liner. In some variations, the liner is removed by the physician prior to insertion. In other variations, the liner is configured to dissolve upon contact with bodily fluid or after a force is applied to the distal anchor. The adhesive may initially strengthen the bond of the proximal-most foldable member to the tissue and then gradually degrade in strength as fistula tract healing occurs or after fistula tract healing. Depending on the variation, the adhesive may create a fluid impermeable seal for at least 7, 14, 21, 28, 35, 60 or any other number of days. The structure for a secure and lasting coupling may also comprise microneedles, such as hooks and/or barbs. The microneedles may be distributed throughout the proximal surface of the proximal-most member, but may also be distributed at predetermined locations. In some variations, the microneedles are distributed along a perimeter of the proximal surface, but in other variations the microneedles may be distributed at a position where contact is anticipated, such as the inner sealing regions described herein.

In some variations, a drug-eluting or therapeutic agent may be added to the distal anchor or the suture associated therewith. The drug-eluting or therapeutic agent may include healing factors, antibiotics, or other healing agents, for example. In some variations, the drug-eluting agent is coated on a foldable member or a suture. In other variations, the therapeutic agent is impregnated within a foldable member or a suture and may be configured for latent release.

In some variations, one or more of the foldable members or the suture may comprise a radio-opaque material or radio-opaque markers. In this way, the distal anchor or suture can be viewed in vivo by using an X-ray, CT scanner, or similar imaging devices.

Figure 18:
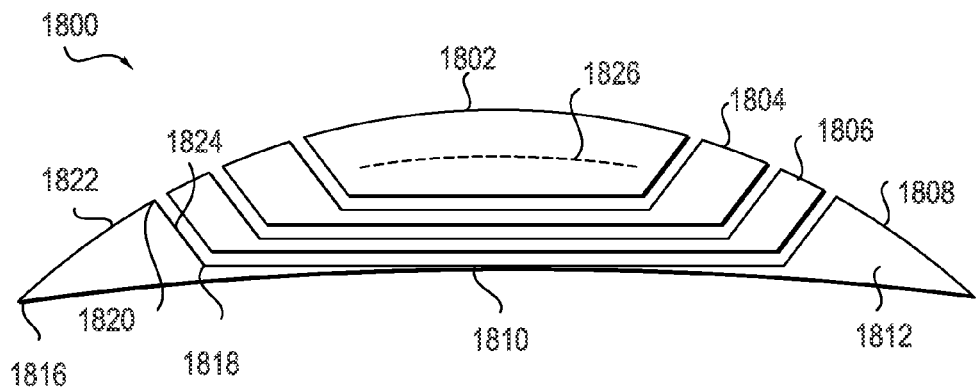
FIG. 18 is a cross-sectional side elevational view of one example of a multi-disc anchor.

FIGS. 18 to 24 depict cross-sectional views of exemplary topographical features for coupling adjacent foldable members. FIG. 18 depicts a cross-sectional view of distal anchor 1800 comprising foldable members 1802, 1804, 1806, and 1808 in the deployed configuration. The cross-sectional profile of each foldable member can be characterized as having two dimensions, a width dimension (horizontal dimension as viewed in FIG. 18) and a height dimension (vertical dimension as viewed in FIG. 18). The foldable members are configured to generally orient the width dimension of the distal anchor 1800 in parallel with the surface of a body lumen when the distal anchor is in the restrained configuration. Each of the foldable members 1802, 1804, 1806, and 1808 include topographical features configured to restrain relative movement of the foldable members in a direction parallel to the width of the foldable member. In this way, distal anchor 1800 may be rigidly coupled to the surface of the body lumen.

A proximal surface of each of the distal-most foldable member 1802, first inner foldable member 1804, and second inner foldable member 1806 is contoured to receive a distal surface of the first inner foldable member 1804, second inner foldable member 1806, and proximal-most foldable member 1808, respectively. The surface contours of each of the foldable members serve to relatively restrain the foldable members in the width dimension. Because the cross-sectional view shown in FIG. 18 is at least partially revolved about an axis generally oriented in the height dimension, the surface contours of each of the foldable members serve to relatively restrain the foldable members in a plane orthogonal to the height dimension. Further, because a suture restrains the foldable members in the height dimension, the foldable members of the distal anchor 1800 is relatively restrained in three orthogonal dimensions, thereby securely holding the distal anchor in position on the surface of a body lumen at the distal opening of a fistula tract.

Proximal-most foldable member 1808 may be generally described as having an inner region 1810 and an outer region 1812 on its distal surface. Inner region 1810 may be defined as a generally smooth surface, such as a surface with a constant radius of curvature. Outer region 1812 may be defined as beginning at a point at which the constant radius of curvature ends—such as the angular region 1818 identified in FIG. 18—and continuing until the peripheral edge of foldable member 1808. Outer region 1812 may be a distal protrusion 1814 and inner region 1810 may be a recess, such as depicted in FIG. 18. In other variations, an inner region is a distal protrusion and an outer region is a recess. The proximal surface of the foldable member adjacent to the proximal-most foldable member may be contoured to relatively restrain the adjacent foldable member. For example, second inner foldable member 1806 comprises a proximally protruding inner region and a recessed outer region, as depicted in FIG. 18.

Distal protrusion 1814 of proximal-most foldable member 1808 restrains the second inner foldable member 1806 in the width dimension. Protrusion 1814 may be characterized by angular region 1816, angular region 1818, angular region 1820, and the length of the sides 1822 and 1824 connecting angular region 1816 to angular region 1820 and angular region 1820 to angular region 1818, respectively. Angular region 1816 may be characterized as the angle between a proximal surface of the proximal-most foldable member 1808 and the side 1822 of the proximal-most foldable member 1808. In some variations, this angle may be any angle between 0 and 90 degrees, including 0°, 10°, 20°, 30°, 40°, 50°, 60°, 70°, 80°, and 90°, or any range between any two of the above angles. Angular region 1818 may be characterized as the angle between the side 1824 of the proximal-most foldable member 1808 and the surface of the inner region 1810 of the proximal-most foldable member 1808. In some variations, this angle may be any angle between 180 and 270 degrees, including 180°, 190°, 200°, 210°, 220°, 230°, 240°, 250°, 260°, and 270°, or any range between any two of the above angles. In some further variations, angular region 1818 may include an angle greater than 270 degrees to provide a "snap-fit" with an opposing surface of an adjacent foldable member. Angular region 1820 may be characterized as the angle between the side 1822 of the proximal-most foldable member 1808 and the side 1824 of the proximal-most foldable member 1808. In some variations, this angle may be any angle between 0 and 180 degrees, including 0°, 10°, 20°, 30°, 40°, 50°, 60°, 70°, 80°, 90°, 100°, 110°, 120°, 130°, 140°, 150°, 160°, 170°, and 180°, or any range between any two of the above angles. Although angles 1816, 1818, and 1820 are depicted in FIG. 18 as sharp corners, other variations may include filleted or rounded angles. Sides 1822 and 1824 may be linear or non-linear. For example, side 1822 may be curved where side 1824 may be flat. In other variations, side 1822 may be flat and side 1824 may be curved. In yet other variations, sides 1822 and 1824 may be both curved or both flat. Sides 1822 and 1824 may be characterized as a percentage of the width of the proximal-most foldable member 1808 and may sometimes be about 5%, 10%, 20%, 30%, 40%, 50%, 60%, 70%, 80%, 90%, or 95%, or any percentage range between any two of the above percentages.

The relative widths of the inner regions and outer regions may be varied. In some variations, the width of the inner region is characterized as a percentage of the width of the outer region and may sometimes be about 5%, 10%, 20%, 30%, 40%, 45%, 50%, 60%, 70%, 80%, 90%, or 95%, or any percentage range between any two of the above percentages. In some variations, the width of the outer region is characterized as a percentage of the width of the inner region and may sometimes be about 5%, 10%, 20%, 30%, 40%, 45%, 50%, 60%, 70%, 80%, 90%, or 95%, or any percentage range between any two of the above percentages.

Proximal-most folding member 1808 is depicted as comprising an inner region which is relatively thin with respect to the total thickness of the distal anchor 1800 in the constrained configuration. In some variations, the thickness of the inner region is characterized as a percentage of the thickness of the distal anchor 1800 in the constrained configuration and may sometimes be about 5%, 10%, 20%, 30%, 40%, 45%, 50%, 60%, 70%, 80%, 90%, or 95%, or any percentage range between any two of the above percentages.

Proximal-most foldable member 1808 is illustrated as comprising a generally concave proximal surface with a constant radius of curvature. In other variations, the proximal surface of proximal-most foldable member 1808 has a non-constant radius of curvature. In yet other, variations the proximal surface of proximal-most foldable member 1808 comprises any of the surface geometries described herein. In some variations, the proximal surface of proximal-most foldable member 1808 is contoured to improve alignment with a non-planar surface of a body lumen.

In some variations, the cross-sectional profile of the foldable members illustrated in FIG. 18 is rotated 180 degrees to generate the three-dimensional geometry of the foldable members. That is, the cross-sectional profile illustrated in FIG. 18 may be representative of any cross-sectional profile taken through a center point of the foldable members. In other variations, the profile is not rotated 180 degrees, that is, the foldable member may not comprise the same cross-sectional profile taken through a center point of the foldable member at every angle. For example, the cross-sectional profile illustrated in FIG. 18 may be repeated for a first range of degrees and then a different cross-sectional profile repeated for a second range of degrees. For example, the cross-sectional profile for the first range may be that depicted in FIG. 18 where the cross-sectional profile for the second range may be generally smooth. This patterning may better facilitate folding of the foldable members, while still relatively restraining the foldable members. In some variations, the first range is larger than the second range.

The second inner foldable member 1806 may comprise a proximal surface that is contoured to align exactly with the contours of the distal surface of proximal-most foldable member 1808. In some variations, the surfaces do not align exactly and may be contoured only as is necessary to provide a predetermined limit on relative movement between the foldable members in the transverse direction. As depicted in FIG. 18, the proximal surface of the second foldable member 1806 has a similar geometry to the proximal surface of the proximal-most foldable member 1808. In other variations, the proximal surface of the second inner foldable member 1806 has a dissimilar geometry to the proximal surface of the proximal-most foldable member 1808. Further, although the inner and outer regions of the second foldable member 1806 have similar widths to the inner and outer regions of the proximal-most foldable member, other variations may have dissimilar widths. Likewise, although the angles on the distal surface of the second inner foldable member 1806 are similar to the angles on the distal surface of the proximal-most foldable member 1808, other variations have dissimilar angles as those on the distal surface of the proximal-most foldable member 1808. Any angular features on first inner foldable member 1804 may take any of the angles described above with respect to proximal-most foldable member 1808. Similarly, any inner and outer regions of inner foldable member may take any of the relative thickness described above with respect to proximal-most foldable member 1808.

Additional inner foldable members may take similar structures and provide similar functions as those described above with respect to second inner foldable member 1806. For example, first inner foldable member 1804 may comprise a proximal surface configured to align exactly with the contours of the distal surface of second inner foldable member 1806, but other variations may not align the opposing surfaces exactly. Any angular features on second inner foldable member 1806 may take any of the angles described above with respect to proximal-most foldable member 1808. Similarly, any inner and outer regions of first inner foldable member 1804 may take any of the relative widths described above with respect to proximal-most foldable member 1808.

Similarly, the proximal surface of distal-most foldable member 1802 may take similar structures and provide similar functions as those described above with respect to the proximal-most foldable member 1808 and the inner foldable members 1804 and 1806. Any angular features on distal-most foldable member 1802 may take any of the angles described above with respect to the inner foldable member 1804 and 1806. Similarly, any inner and outer regions of distal-most foldable member 1802 may take any of the relative thickness described above with respect to proximal-most foldable member 1808.

Distal-most foldable member 1802 may be concave on its distal surface, as depicted in FIG. 18. In some variations, the distal surface of distal-most foldable member 1802 is not concave. In particular, the distal surface of the distal-most foldable member is not constrained by an interaction with the surface of a distally adjacent foldable member. Accordingly, the distal surface of distal-most foldable member 1802 may be smooth to prevent any lodging of external elements, such as partially digested foot particles. In some variations, the distal surface of distal-most foldable member 1802 may take a form that facilitates folding of foldable member prior to deployment. In some variations, the distal surface of distal-most foldable member 1802 comprises a suture attachment structure. In further variations, the suture attachment structure may include reinforcement structure 1826. Reinforcing structure 1826 may be a wire mesh embedded within distal-most foldable member 1802 and configured to distribute the force resulting from tensioning the suture across all or some of distal-most foldable member 1802, thereby reducing the risk of rupturing the foldable member. In other variations, the reinforcing structure might include a button-shaped suture attachment structure, wherein the expanded areas of the button-shaped suture attachment structure serves to distribute the force over a wider area.

Figure 19:
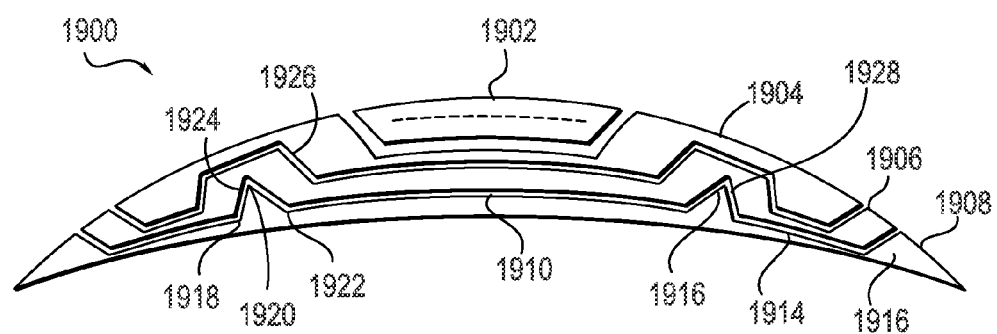
FIG. 19 is a cross-sectional side elevational view of another example of a multi-disc anchor.

FIG. 19 depicts a cross-sectional view of distal anchor 1900 comprising distal-most foldable member 1902, first inner foldable member 1904, second inner foldable member 1906, and proximal-most foldable member 1908 in the deployed configuration. Distal anchor 1900 includes additional distal protrusions on the foldable members for further restraining the relative movement of the foldable members. Proximal-most foldable member 1908 comprises a first inner region 1910, a first distal protrusion 1912, a second inner region 1914, and an outer region 1916. Outer region 1916 may comprise similar features and structures to outer region 1814 described above with respect to distal anchor 1800. Similarly, the first inner region 1910 may comprises similar features to inner region 1810 described above with respect to distal anchor 1800. First distal protrusion 1912 may limit relative movement of second inner foldable member 1906 relative to proximal-most foldable member 1908.

First distal protrusion 1912 of proximal-most foldable member 1908 restrains the second inner foldable member 1906 in the width dimension. Protrusion 1914 may be characterized by angular region 1918, angular region 1920, angular region 1922, and the length of the sides 1924 and 1926 joining angular region 1918 to angular region 1920 and angular region 1920 to angular region 1922, respectively. Angular region 1918 may be characterized as the angle between the second inner region 1914 and the side 1924. In some variations, this angle may be any angle between 180 and 270 degrees, including 180°, 190°, 200°, 210°, 220°, 230°, 240°, 250°, 260°, and 270°, or any range between any two of the above angles. In some further variations, angular region 1918 may include an angle greater than 270 degrees to provide a "snap-fit" with an opposing surface of an adjacent foldable member. Angular region 1920 may be characterized as the angle between the side 1924 and the side 1926. In some variations, this angle may be any angle between 0 and 180 degrees, including 0°, 10°, 20°, 30°, 40°, 50°, 60°, 70°, 80°, 90°, 100°, 110°, 120°, 130°, 140°, 150°, 160°, 170°, and 180°, or any range between any two of the above angles. Angular region 1922 may be characterized as the angle between the first inner region 1910 and the side 1926. In some variations, this angle may be any angle between 180 and 270 degrees, including 180°, 190°, 200°, 210°, 220°, 230°, 240°, 250°, 260°, and 270°, or any range between any two of the above angles. In some further variations, angular region 1922 may include an angle greater than 270 degrees to provide a "snap-fit" with an opposing surface of an adjacent foldable member. Although angles 1918, 1920, and 1922 are depicted in FIG. 19 as sharp corners, other variations may include filleted or rounded angles. Sides 1924 and 1926 may be linear or non-linear. For example, side 1924 may be curved where side 1926 may be flat. In other variations, side 1924 may be flat and side 1926 may be curved. In yet other variations, sides 1924 and 1926 may be both curved or both flat. The length of each of sides 1924 and 1926 may be characterized as a percentage of the width of the proximal-most foldable member 1908 and may sometimes be about 5%, 10%, 20%, 30%, 40%, 45%, 50%, 60%, 70%, 80%, 90%, or 95%, or any percentage range between any two of the above percentages.

The relative widths of first inner region 1910, first distal protrusion 1912, second inner region 1914, and outer region 1916 may be varied. In some variations, the widths of first inner region 1910, first distal protrusion 1912, and second inner region 1914 may be characterized as percentages of the width of outer region 1916 and may sometimes be about 5%, 10%, 20%, 30%, 40%, 45%, 50%, 60%, 70%, 80%, 90%, or 95%, or any percentage range between any two of the above percentages. In some variations, the widths of first inner region 1910, first distal protrusion 1912, and outer region 1916 may be characterized as percentages of the width of second inner region 1914 and may sometimes be about 5%, 10%, 20%, 30%, 40%, 45%, 50%, 60%, 70%, 80%, 90%, or 95%, or any percentage range between any two of the above percentages. In some variations, the widths of first inner region 1910, second inner region 1914, and outer region 1916 may be characterized as percentages of the width of first distal protrusion 1912 and may sometimes be about 5%, 10%, 20%, 30%, 40%, 45%, 50%, 60%, 70%, 80%, 90%, or 95%, or any percentage range between any two of the above percentages. In some variations, the widths of first distal protrusion 1912, second inner region 1914, and outer region 1916 may be characterized as percentages of the width of first inner region 1910 and may sometimes be about 5%, 10%, 20%, 30%, 40%, 45%, 50%, 60%, 70%, 80%, 90%, or 95%, or any percentage range between any two of the above percentages.

Second inner foldable member 1906 may comprise a recess 1928 on its proximal surface corresponding to the first distal protrusion 1912 of proximal-most foldable member 1908. Recess 1928 may be defined by the length of the side surfaces and the angles created where the sides meet each other and where the sides meet the proximal surface of second inner foldable member. The lengths of the side surfaces may be characterized as a percentage of the diameter of the proximal-most foldable member 1908 and may sometimes be about 5%, 10%, 20%, 30%, 40%, 45%, 50%, 60%, 70%, 80%, 90%, or 95%, or any percentage range between any two of the above percentages. The angle may correspond to the angles of the distal protrusion 1912 on proximal-most foldable member 1908.

First inner foldable member 1904 may comprise a recess on its proximal surface corresponding to a distal protrusion on second foldable member 1906. The recess may be defined by the length of the side surfaces and the angles created where the sides meet each other and where the sides meet the proximal surface of second inner foldable member. The lengths of the side surfaces may be characterized as a percentage of the width of the proximal-most foldable member 1908 and may sometimes be about 5%, 10%, 20%, 30%, 40%, 45%, 50%, 60%, 70%, 80%, 90%, or 95%, or any percentage range between any two of the above percentages. The angle may correspond to the angles of the distal protrusion on second inner foldable member 1906.

Distal-most foldable member 1902 may share similar geometries and functions as distal-most foldable member 1802.

Although FIGS. 18 and 19 illustrate one and two distal protrusions, respectively, on a distal surface of the proximal-most foldable member, other variations may have 3, 4, 5, or any number of protrusions. Further, although FIGS. 18 and 19 illustrate a distal protrusion on the perimeters of the proximal-most foldable member, first inner foldable member, and second inner foldable member, other variations may have a distal recess on the perimeter of any of the foldable members.

Figure 20A:
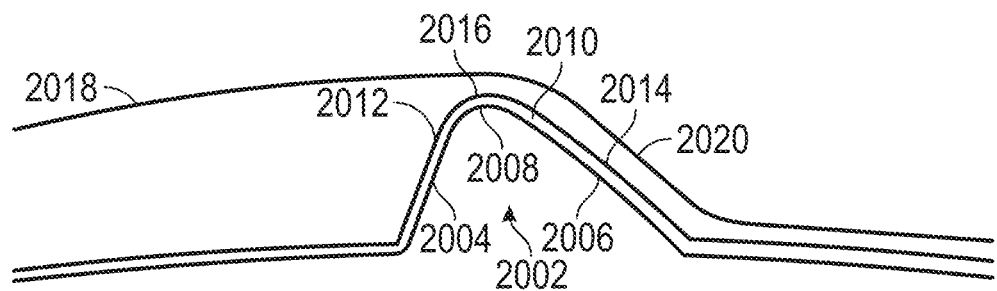
FIGS. 20A-20C depicts various configurations of interdisc interfaces in a multi-disc anchor.
Figure 20B:
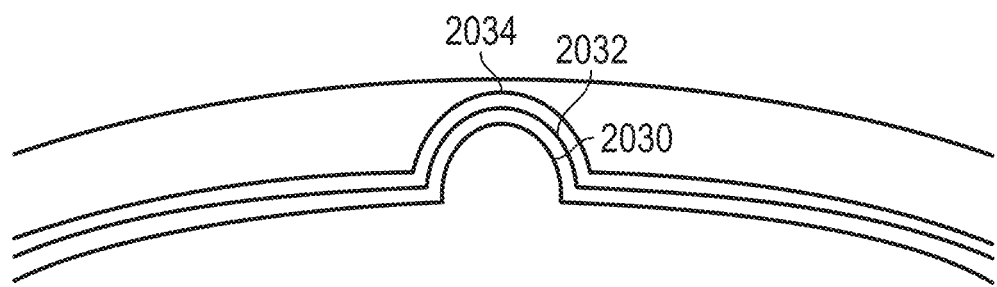
Figure 20C:
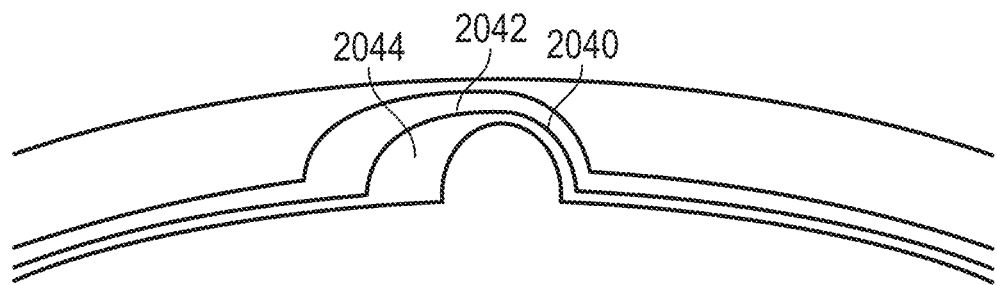

FIGS. 20A to 20C depict various protrusions and recesses configured for coupling adjacent foldable members. FIG. 20A depicts a cross-sectional view of protrusion 2002 of a proximal foldable member configured to be coupled to a recess 2010 of a distal foldable member adjacent to the proximal foldable member. As can be seen in FIG. 20A, protrusion 2002 comprises two angled sides 2004 and 2006 connected by a rounded apex 2008. Recess 2010 comprises an inner proximal surface 2012 and an outer proximal surface 2014 connected by a fillet 2016. The distal foldable member further comprises a distal surface including inner distal surface 2018 and outer distal surface 2020. Inner distal surface 2020 may be oriented approximately in parallel to a distal surface of the proximal foldable member. In this way, the distal foldable member provides more material behind the face at which the recess 2010 and protrusion 2002 are forced together. That is, as the distal foldable member is restrained, the inner proximal surface 2012 of the distal foldable member is forced against the side 2004 of the proximal foldable member. Including additional material behind this point may provide additional support to the distal foldable member when the two foldable members are forced together. By contrast, there is less force exerted on the outer proximal surface 2014. Accordingly, outer distal surface 2020 may be generally parallel to the side 2006, resulting in a thinner outer region of the distal foldable member. This may facilitate folding the foldable member prior to insertion or may provide a reduction in manufacturing costs.

FIG. 20B depicts a cross-sectional view of protrusion 2030 of a proximal foldable member configured to be coupled to a recess 2032 of a thin inner foldable member adjacent to the proximal foldable member, where the recess 2032 is further configured to be coupled to a recess 2034 of a distal foldable member. Introducing a thin inner foldable member between the distal and proximal foldable member may further distribute the pressure on the foldable members when in the restrained configuration. In addition, inner foldable member may comprise an adhesive to strengthen the coupling between the proximal and distal foldable members.

FIG. 20C depicts a cross-sectional view of protrusion 2040 of a proximal foldable member configured to be coupled to a recess 2042 of a distal foldable member. Recess 2042 includes a cavity 2044 which may facilitate coupling of the distal and proximal foldable members without deforming the proximal-most foldable member. More specifically, as the distal foldable member is restrained, the recess 2042 slides laterally on the protrusion 2040 so that the cavity 2044 moves to the other side of protrusion 2040. In this way, no additional forces may be exerted on the protrusion 2040 in the lateral direction due to restraining the distal foldable member.

Figure 21:
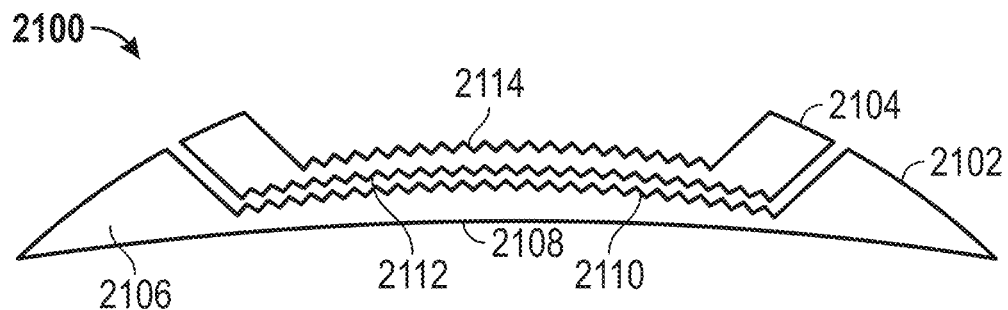
FIG. 21 is a cross-sectional side elevational view of another example of a multi-disc anchor, without the distalmost portion.

FIG. 21 depicts a cross-sectional view of a portion 2100 of a distal anchor, comprising proximal-most foldable member 2102 and first inner foldable member 2104. Proximal-most foldable member 2102 has distal protrusion 2106 in its outer region. Distal protrusion 2106 may comprise the geometry of any of the protrusions described herein. Inner region 2108 of proximal-most foldable member 2102 comprises teeth 2110 configured to restrain relative movement of the first inner foldable member. The proximal surface of the first inner foldable member may also comprise teeth 2112 configured to engage with the teeth 2108 of the proximal-most foldable member. The distal surface of the first inner foldable member 2104 may also comprise teeth 2114 configured to engage with a proximal surface of an adjacent foldable member (not shown).

In some variations, teeth configured to restrain movement may take the form of a series of peaks and troughs. In some variations, the peaks and troughs may be symmetrical. In other variations, the peaks and troughs may not be symmetrical. In some variations, the peaks and troughs may repeat at constant distances. In other variations, the peaks and troughs may be distributed unevenly throughout the surface of the foldable member. In some variations, the peaks and troughs are rounded. In others, some or all of the peaks and troughs have pointed edges. In some variations, an opposing surface of an adjacent foldable member may have a recess configured to receive the teeth. In other variations, the opposing surface of the adjacent foldable member does not include a recess for one or more of the teeth. In some variations, each surface of a foldable member that opposes a surface of an adjacent foldable member has teeth. In other variations, one or more of the foldable members of a distal anchor does not include teeth. In some variations, the teeth protrude the same distance from the surface of the foldable member. In other variations, one or more teeth protrude at a different distance from the surface of the foldable member. In some variations, the distance the teeth protrude from the surface of the foldable member may be characterized as a percentage of the thickness of the foldable member without the teeth and may sometimes be about 5%, 10%, 20%, 30%, 40%, 45%, 50%, 60%, 70%, 80%, 90%, or 95%, or any percentage range between any two of the above percentages. In some variations, the thickness of the foldable member without the teeth may be characterized as a percentage of the distance the teeth protrude from the surface of the foldable member and may sometimes be about 5%, 10%, 20%, 30%, 40%, 45%, 50%, 60%, 70%, 80%, 90%, or 95%, or any percentage range between any two of the above percentages.

Figure 22:
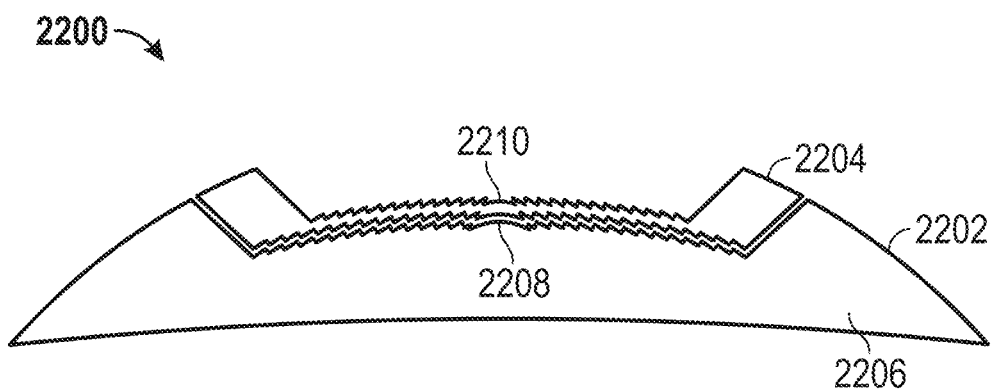
FIG. 22 is a cross-sectional side elevational view of another example of a multi-disc anchor, without the distalmost portion.

FIG. 22 depicts a cross-sectional view of a portion 2200 of a distal anchor comprising teeth between adjacent foldable members 2202 and 2204. Proximal-most foldable member 2202 may have some features which are similar to proximal-most foldable member 2102 described above with respect to FIG. 21. Proximal-most foldable member 2202 may be thicker than proximal-most foldable member 2102, resulting in a wider outer region 2206. First inner foldable member 2204 may have some features which are similar to first inner foldable member 2104 described above with respect to FIG. 21. Proximal-most foldable member 2202 and first inner foldable member 2204 may comprise central regions 2208 and 2210, respectively, without teeth. An aperture may be positioned in central regions 2208 and 2210 for receiving a suture.

Figure 23A:
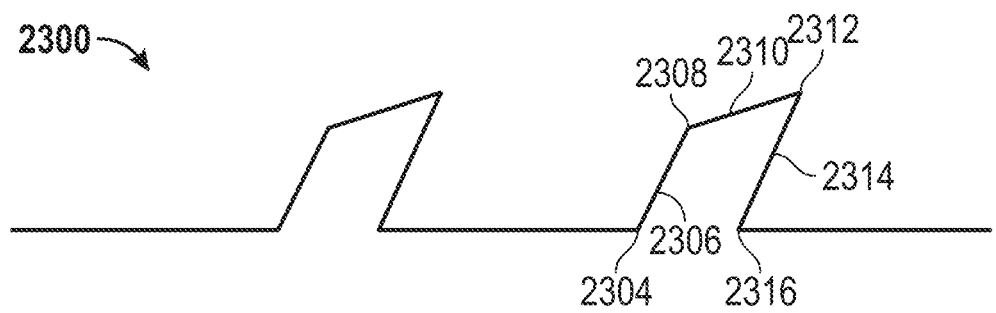
FIGS. 23A-23C depicts various configurations of interdisc interfaces in a multi-disc anchor.

FIG. 23A depicts a cross-sectional view of a set 2300 of teeth configured for coupling adjacent foldable members. Each tooth may comprise a first angular region 2304, a first side 2306, a second angular region 2308, a second side 2310, a third angular region 2312, a third side 2314, and a fourth angular region 2316. First angular region 2304 may be characterized by the angle created by the surface of the foldable member 2302 and the first side 2306, where the angle may sometimes be 180°, 190°, 200°, 210°, 220°, 230°, 240°, 250°, 260°, and 270°, or any range between any two of the above angles. First side 2306 may be characterized as a percentage of the thickness of the foldable member and may sometimes be 5%, 10%, 20%, 30%, 40%, 45%, 50%, 60%, 70%, 80%, 90%, or 95%, or any percentage range between any two of the above percentages. Second angular region 2308 may be characterized by the angle created by the first side 2306 and the second side 2310, where the angle may sometimes be 180°, 190°, 200°, 210°, 220°, 230°, 240°, 250°, 260°, 270°, 280°, 290°, 300°, 310°, 320°, 330°, 340°, 350°, and 360°, or any range between any two of the above angles. Second side 2310 may be characterized as a percentage of the thickness of the foldable member and may sometimes be 5%, 10%, 20%, 30%, 40%, 45%, 50%, 60%, 70%, 80%, 90%, or 95%, or any percentage range between any two of the above percentages. Third angular region 2312 may be characterized by the angle created by the second side 2310 and the third side 2314, where the angle may sometimes be 270°, 280°, 290°, 300°, 310°, 320°, 330°, 340°, 350°, and 360°. Third side 2314 may be characterized as a percentage of the thickness of the foldable member and may sometimes be 5%, 10%, 20%, 30%, 40%, 45%, 50%, 60%, 70%, 80%, 90%, or 95%, or any percentage range between any two of the above percentages. Fourth angular region 2304 may be characterized by the angle created by the surface of the foldable member 2302 and the third side 2314, where the angle may sometimes be 270°, 280°, 290°, 300°, 310°, 320°, 330°, 340°, 350°, and 360°, or any range between any two of the above angles.

Figure 23B:
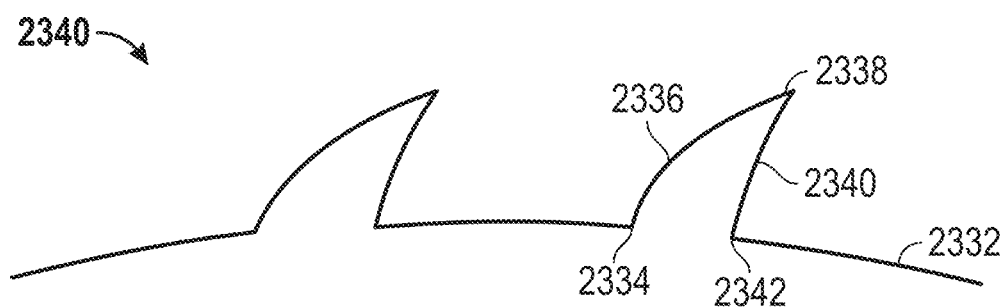

FIG. 23B depicts a cross-sectional view of a set 2330 of teeth configured for coupling adjacent foldable members. Each tooth may comprise a first angular region 2334, a first side 2336, a second angular region 2338, a second side 2340, and a third angular region 2332. First angular region 2334 may be characterized by the angle created by the surface of the foldable member 2332 and the first side 2336, where the angle may sometimes be 180°, 190°, 200°, 210°, 220°, 230°, 240°, 250°, 260°, and 270°, or any range between any two of the above angles. First side 2336 may be curved, wherein the length of the curve is characterized as a percentage of the thickness of the foldable member and may sometimes be 5%, 10%, 20%, 30%, 40%, 45%, 50%, 60%, 70%, 80%, 90%, or 95%, or any percentage range between any two of the above percentages. Second angular region 2338 may be characterized by the angle created by the first side 2336 and the second side 2340, where the angle may sometimes be 180°, 190°, 200°, 210°, 220°, 230°, 240°, 250°, 260°, 270°, 280°, 290°, 300°, 310°, 320°, 330°, 340°, 350°, and 360°, or any range between any two of the above angles. Second side 2340 may be characterized as a percentage of the thickness of the foldable member and may sometimes be 5%, 10%, 20%, 30%, 40%, 45%, 50%, 60%, 70%, 80%, 90%, or 95%, or any percentage range between any two of the above percentages Third angular region 2342 may be characterized by the angle created by the surface of the foldable member 2332 and the third side 2340, where the angle may sometimes be 270°, 280°, 290°, 300°, 310°, 320°, 330°, 340°, 350°, and 360°, or any range between any two of the above angles.

Figure 23C:
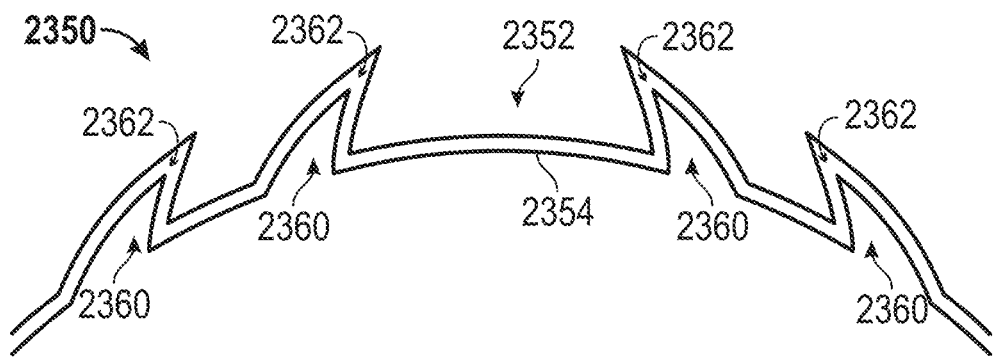

FIG. 23C shows a cross-sectional view of pair 2350 of foldable members, first foldable member 2352 and second foldable member 2354. First foldable member 2352 may comprise recesses 2362 configured to receive teeth 2360 on second foldable member 2354. As can be seen in FIG. 23C, the teeth and recesses are symmetrical about a center point of each foldable member. This may facilitate an annular rib on the foldable member when viewed in three-dimensions, that is, when the cross-section depicted in FIG. 23C is revolved 180 degrees. In other variations, the teeth may not be symmetrical about a center point of each foldable member.

Figure 24:
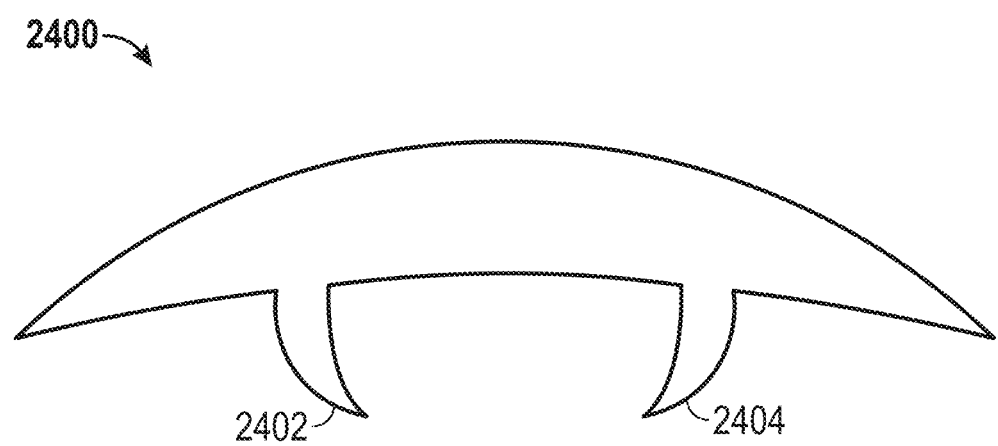
FIG. 24 depicts a tissue-engaging feature of an exemplary anchor.

FIG. 24 depicts a cross-sectional view of foldable member 2400 which comprises teeth 2402 and 2404. Teeth 2402 and 2404 may include a surface of relatively large curvature, thereby facilitating a snap-fit when foldable member 2400 engages recesses in an adjacent foldable member. Teeth 2402 and 2404 may be configured to move transversely within the recess of the adjacent foldable member as the pair of foldable members are forced together.

Figure 25:
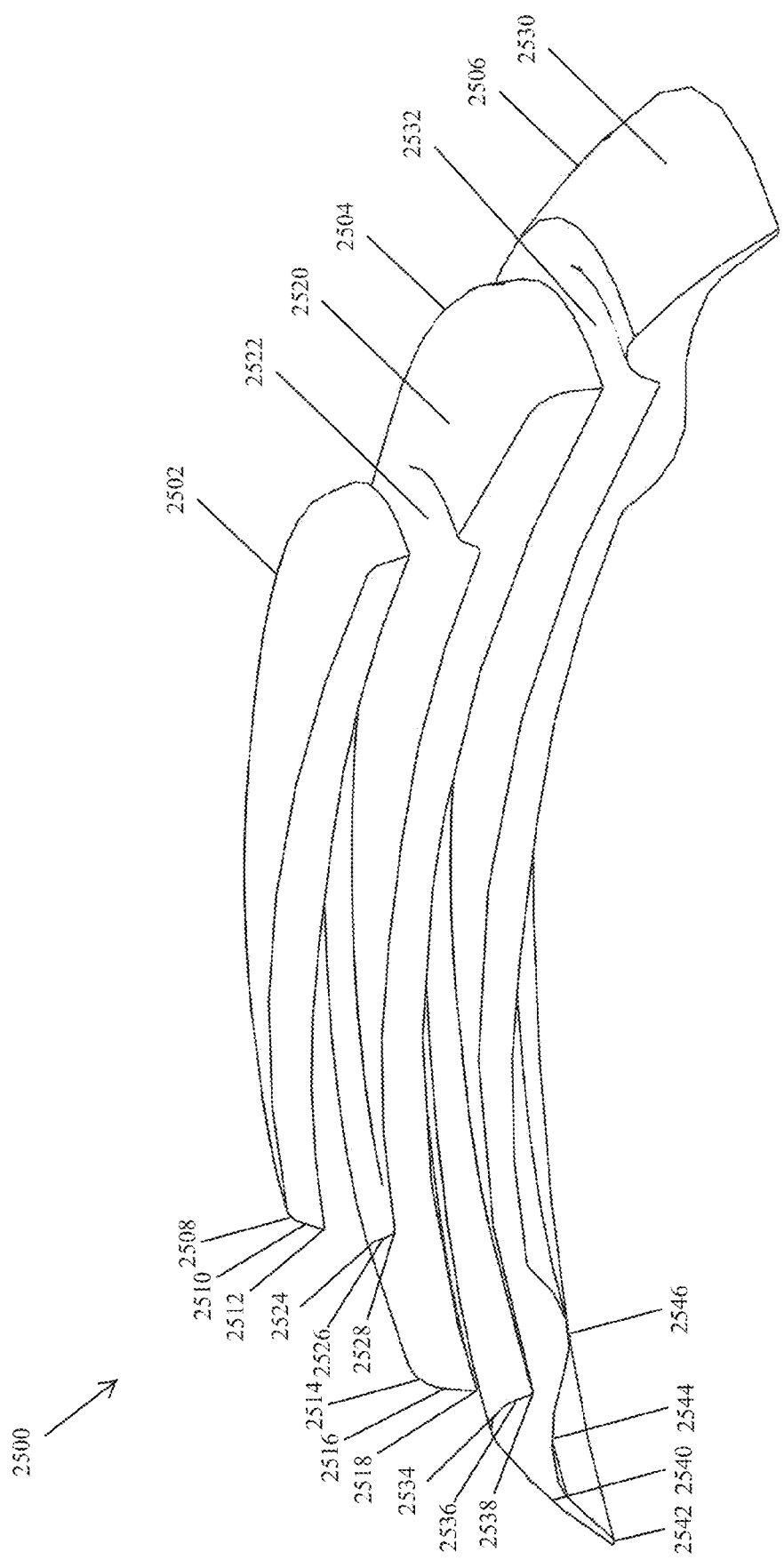
FIG. 25 is a cross-sectional perspective view of another example of a multi-disc anchor.

FIG. 25 illustrates a cut-away, exploded view of a distal anchor 2500 comprising a distal-most foldable member 2502, an inner foldable member 2504, and a proximal-most foldable member 2506. Inner foldable member 2504 and proximal-most foldable member 2506 comprise recesses 2522 and 2532, respectively, configured to receive the distally adjacent foldable member. The design of distal anchor 2500 may serve to relatively restrain the foldable members while sill reducing manufacturing costs. Proximal-most foldable member 2530 may further comprise structure on its proximal surface to enable the distal anchor 2500 to better couple to a surface of a body lumen at the distal opening of a fistula tract.

Distal-most foldable member 2502 comprises generally concave distal and proximal surfaces. As illustrated in FIG. 25, the distal surface of distal-most foldable member 2502 has a greater curvature than the proximal surface, that is, the distal surface of distal-most foldable member 2502 has a smaller radius of curvature than the proximal surface. The greater curvature of the distal surface results in a thicker central region, which may provide additional structural support when a suture (not shown) is attached to a suture attachment structure (not shown) on the distal-most foldable member 2502. In some variations, the radius of curvature of the distal surface may be characterized as a percentage of the radius of curvature of the proximal surface and sometimes may be 75%, 80%, 85%, 90%, 95%, 100%, or any percentage range between any two of the above percentages. In other variations, the proximal surface of the distal-most foldable member 2502 comprises a greater curvature than the distal surface that is, the proximal surface of distal-most foldable member 2502 has a smaller radius of curvature than the distal surface. In some variations, the radius of curvature of the proximal surface may be characterized as a percentage of the radius of curvature of the distal surface and sometimes may be 75%, 80%, 85%, 90%, 95%, 100%, or any percentage range between any two of the above percentages. Distal-most foldable member 2502 also comprises a distal angular region 2508, a perimeter surface 2510, and a proximal angular region 2512. Distal angular region 2508, perimeter surface 2510, and proximal angular region 2512 may be configured to mate distal-most foldable member 2502 with a recess in inner foldable member 2504. Distal angular region 2508 may be an arc with a radius and an angle. In some variations, the radius is characterized as a percentage of the diameter of the distal-most foldable member, and may sometimes be 5%, 10%, 20%, 30%, 40%, 45%, 50%, 60%, 70%, 80%, 90%, or 95%, or any percentage range between any two of the above percentages. In some variations, the angle may sometimes be 0°, 10°, 20°, 30°, 40°, 50°, 60°, 70°, 80°, 90°, 100°, 110°, 120°, 130°, 140°, 150°, 160°, 170°, and 180°, or any range between any two of the above angles. In other variations, distal angular region 2508 may be a pointed corner created by the distal surface of distal-most foldable member 2502 and the perimeter surface 2510. In some variations, the angle of the pointed corner may be 90°, 100°, 110°, 120°, 130°, 140°, 150°, 160°, 170°, and 180°, or any range between any two of the above angles. In some variations, perimeter surface 2510 may comprise a length characterized as a percentage of the diameter of the distal-most foldable member, and may sometimes be 1%, 2%, 3%, 4%, 5%, 10%, 15%, 20%, 25%, 30%, or any percentage range between any two of the above percentages. In some variations, proximal angular region 2512 may be a pointed corner created by the proximal surface of distal-most foldable member 2502 and the perimeter surface 2510. In some variations, the angle of the pointed corner may be 0°, 30°, 60°, 90°, 120°, 150°, 180°, or any range between any two of the above angles.

Inner foldable member 2504 comprises a proximal surface and a distal surface. As with distal-most foldable member 2502, the proximal surface may have a different curvature than the distal surface. The distal surface comprises an elevated region 2520 and a recessed region 2522. Elevated region 2520 may include a distal angular region 2514, a perimeter surface 2516, and a proximal angular region 2518. Distal angular region 2514, perimeter surface 2516, and proximal angular region 2518 may comprise any of the geometries discussed above with respect to distal angular region 2508, perimeter surface 2510, and proximal angular region 2512. Recessed region 2522 may be configured to mate inner foldable member 2504 with the proximal surface of distal-most foldable member 2502. Recessed region 2522 may comprise a distal angular region 2524, an interior surface 2526, and a proximal angular region 2528. Distal angular region 2524, interior surface 2526, and proximal angular region 2528 may be configured to mate recess 2522 of inner foldable member 2504 with distal-most foldable member 2502. Distal angular region 2524 may be an arc with a radius and an angle. In some variations, the radius is characterized as a percentage of the diameter of the inner foldable member, and may sometimes be 5%, 10%, 20%, 30%, 40%, 45%, 50%, 60%, 70%, 80%, 90%, or 95%, or any percentage range between any two of the above percentages. In some variations, the angle may sometimes be 0°, 10°, 20°, 30°, 40°, 50°, 60°, 70°, 80°, 90°, 100°, 110°, 120°, 130°, 140°, 150°, 160°, 170°, and 180°, or any range between any two of the above angles. In other variations, distal angular region 2524 may be a pointed corner created by the surface of elevation 2520 and the interior surface 2526. In some variations, the angle of the pointed corner may be 90°, 100°, 110°, 120°, 130°, 140°, 150°, 160°, 170°, and 180°, or any range between any two of the above angles. In some variations, interior surface 2526 may comprise a length characterized as a percentage of the diameter of the inner foldable member, and may sometimes be 1%, 2%, 3%, 4%, 5%, 10%, 15%, 20%, 25%, 30%, or any percentage range between any two of the above percentages. In some variations, proximal angular region 2528 may be a pointed corner created by the surface of recess 2522 and the interior surface 2526. In some variations, the angle of the pointed corner may be 0°, 10°, 20°, 30°, 60°, 90°, 120°, 150°, 180°, or any range between any two of the above angles.

Proximal-most foldable member 2506 comprises a proximal surface and a distal surface. The distal surface comprises a sloped region 2530 and a recessed region 2532. Recessed region 2532 may be configured to mate inner foldable member 2504 with the distal surface of proximal-most foldable member 2506. Recessed region 2532 may comprise a distal angular region 2534, an interior surface 2536, and a proximal angular region 2538. Distal angular region 2534 may be an arc with a radius and an angle. In some variations, the radius is characterized as a percentage of the diameter of the proximal-most foldable member, and may sometimes be 55%, 10%, 20%, 30%, 40%, 45%, 50%, 60%, 70%, 80%, 90%, or 95%, or any percentage range between any two of the above percentages. In some variations, the angle may sometimes be 0°, 10°, 20°, 30°, 40°, 50°, 60°, 70°, 80°, 90°, 100°, 110°, 120°, 130°, 140°, 150°, 160°, 170°, 180°, or any range between any two of the above angles. In other variations, distal angular region 2534 may be a pointed corner created by the surface of sloped region 2530 and the interior surface 2536. In some variations, the angle of the pointed corner may be 90°, 100°, 110°, 120°, 130°, 140°, 150°, 160°, 170°, and 180°, or any range between any two of the above angles. In some variations, interior surface 2536 may comprise a length characterized as a percentage of the diameter of the inner foldable member, and may sometimes be 1%, 2%, 3%, 4%, 5%, 10%, 15%, 20%, 25%, 30%, or any percentage range between any two of the above percentages. In some variations, proximal angular region 2538 may be a pointed corner created by the surface of recess 2532 and the interior surface 2536. In some variations, the angle of the pointed corner may be 0°, 10°, 20°, 30°, 40°, 50°, 60°, 70°, 80°, 90°, 100°, 110°, 120°, 130°, 140°, 150°, 160°, 170°, 180°, or any range between any two of the above angles.

The proximal surface of proximal-most foldable member 2506 may be configured to provide additional support. The proximal surface of proximal-most foldable member may include a recess 2544 and a proximal protrusion 2546. Both recess 2544 and proximal protrusion 2546 may be defined by an arc of a length and an angle. In some variations, the length of the arc is characterized as a percentage of the diameter of the inner foldable member, and may sometimes be 1%, 2%, 3%, 4%, 5%, 10%, 20%, 30%, 40%, 45%, 50%, 60%, 70%, 80%, 90%, or 95%, or any percentage range between any two of the above percentages. In some variations, the angle may sometimes be 0°, 10°, 20°, 30°, 40°, 50°, 60°, 70°, 80°, 90°, 100°, 110°, 120°, 130°, 140°, 150°, 160°, 170°, 180°, or any range between any two of the above angles. Proximal protrusion 2546 may comprise an inner sealing region to prevent ingress of fistula material to the body lumen. Angular region 2542 may comprise an outer edge region of the proximal-most foldable member. In some variations, the outer edge region is oriented at an acute angle to the inner sealing region. In some embodiments, the position of the proximal protrusion may be characterized as a percentage of the diameter of the proximal-most foldable member and may sometimes be 5%, 10%, 20%, 30%, 40%, 45%, 50%, 60%, 70%, 80%, 90%, or 95%, or any percentage range between any two of the above percentages.

Although distal anchor 2500 is illustrated with three foldable members, other variations may include four or more foldable members. Additional foldable members may comprise additional inner foldable members configured to mate to adjacent foldable members. In addition, although the foldable members are illustrated as having an overall curved form, in some variations the foldable members may have an overall planar form. Moreover, any of the overall shapes described herein may be employed. The distal-most and inner foldable members are depicted with a smooth proximal surface, but some variations may include topographical features configured to further restrain relative movement between the foldable members, such as those described herein. In addition, although a suture, a suture attachment structure, and apertures for threading a suture are not illustrated in FIG. 25, some variations include all or some of a suture, a suture attachment structure, and apertures for threading a suture, such as those described herein.

Figure 26:
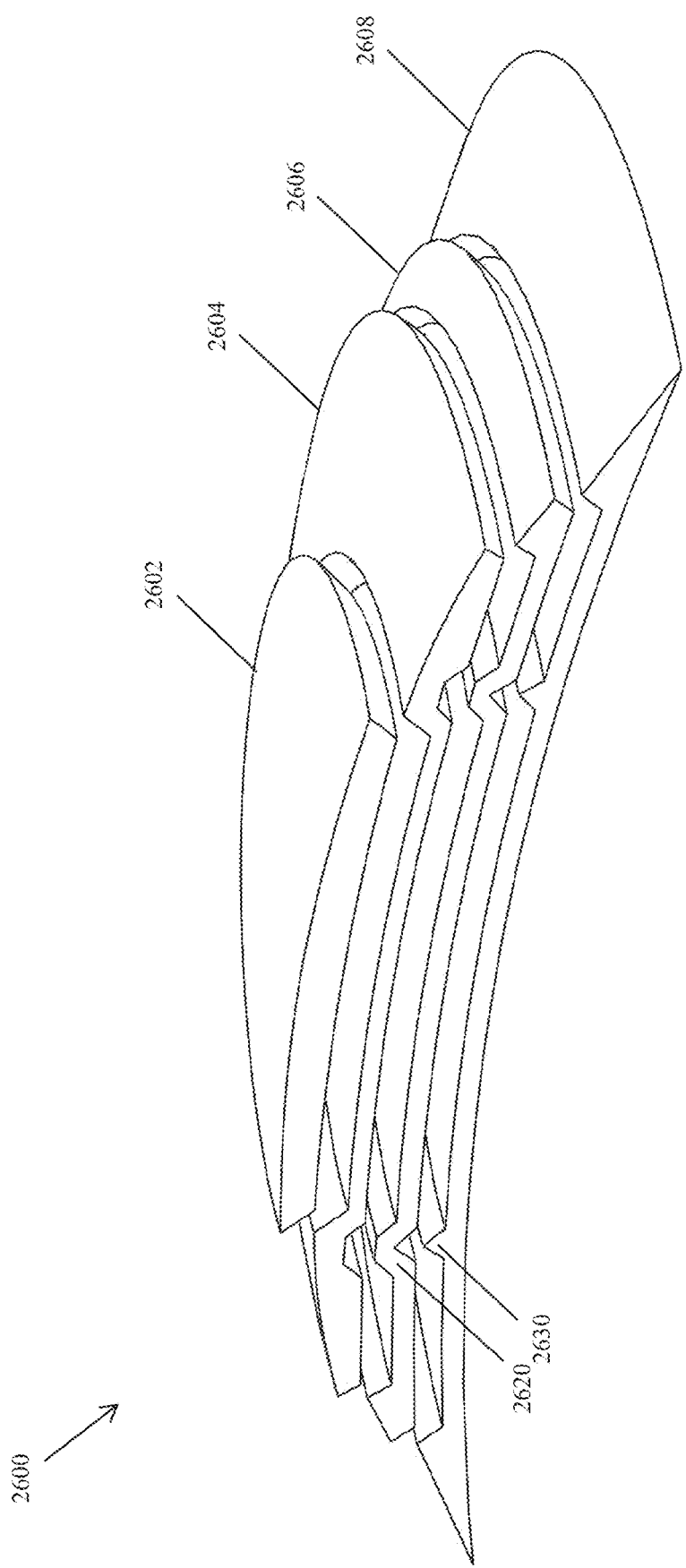
FIG. 26 is a cross-sectional perspective view of another example of a multi-disc anchor.

FIG. 26 illustrates a cut-away, exploded view of a distal anchor 2600 comprising distal-most foldable member 2602, first inner foldable member 2604, second inner foldable member 2606, and proximal-most foldable member 2608. Foldable members 2602, 2604, and 2606, and 2610 are relatively less curved than the foldable members of distal anchor 2500. Second inner foldable member 2606 and proximal-most foldable member 2608 comprise annular ribs 2620 and 2630, respectively. Annular ribs 2620 and 2630 may serve to relatively restrain the foldable members of distal anchor 2600 is in the deployed configuration. The distal surface of each of first inner foldable member 2604, second inner foldable member 2606, and proximal-most foldable member 2608 may comprise an outer distally protruding region and an inner recess. As can be seen in FIG. 26, the width of the outer regions may vary. In other variations, the widths of the outer regions are the same.

As depicted in FIG. 26, annular rib 2620 may be aligned with annular rib 2630, and annular rib 2630 may be aligned with a side surface of a recess in first inner foldable member 2604. In some variations, the annular ribs are not aligned with features on the distal face of the adjacent foldable member. The positioning of the annular ribs on each foldable member may be characterized by a diameter that is a percentage of the overall diameter of the distal anchor 2600, and may sometimes be 5%, 10%, 20%, 30%, 40%, 45%, 50%, 60%, 70%, 80%, 90%, or 95%, or any percentage range between any two of the above percentages. The annular ribs may also comprise a width from the bottom of the slope of one face to the bottom of the slope of the other face, that is, a width of the base of the rib. The widths of the annular ribs may be characterized as a percentage of the overall diameter of the distal anchor 2600, and may sometimes be 1%, 2%, 3%, 4%, 5%, 10%, 15%, 20%, 25%, 30%, or any percentage range between any two of the above percentages. Although annular rib 2630 is illustrated as comprising a pointed apex, other variations may include a rounded or flat apex, such as any of the protrusion geometries discussed herein. Similarly, annular rib 2620 is illustrated as comprising a flat apex, but other variations may include a rounded or pointed apex, such as any of the protrusion geometries discussed herein.

Distal-most foldable member 2602 comprises a generally planar proximal surface and a curved distal surface, with a side surface connecting the proximal and distal surfaces. The side surface of distal-most foldable member 2602 may be oriented at an acute angle to the height dimension, wherein the angle may sometimes be 90°, 100°, 110°, 120°, 130°, 140°, 150°, 160°, 170°, and 180°, or any range between any two of the above angles. The thickness of distal-most foldable member 2602 may be characterized as a percentage of the overall thickness of the distal anchor 2600 in the deployed configuration, and may sometimes be 5%, 10%, 20%, 30%, 40%, 45%, 50%, 60%, 70%, 80%, 90%, or 95%, or any percentage range between any two of the above percentages. The diameter of distal-most foldable member 2602 may be characterized as a percentage of the diameter of proximal-most foldable member 2608, and may sometimes be 5%, 10%, 20%, 30%, 40%, 45%, 50%, 60%, 70%, 80%, 90%, or 95%, or any percentage range between any two of the above percentages.

First inner foldable member 2604 may comprise a protruding outer region and a recess on its distal face. First inner foldable member 2604 may also comprise a recess on its proximal face, which may be aligned with an annular rib on second inner foldable member 2606. The protrusions and recess of first inner foldable member 2604 may comprise any of the protrusion and recess geometries described herein.

Second inner foldable member 2606 may comprise a protruding outer region, a first recess, an annular rib, and a second recess on its distal face. The relative size and positions of the first and second recesses may be determined by the positioning and size of the annular rib. Second inner foldable member 2606 may comprise a recess on its proximal face. The protrusions and recess of second inner foldable member 2606 may comprise any of the protrusion and recess geometries described herein.

Proximal-most foldable member 2608 may comprise a protruding outer region, a first recess, an annular rib, and a second recess on its distal face. The relative size and positions of the first and second recesses may be determined by the positioning and size of the annular rib. Proximal-most foldable member 2608 may comprise a smooth proximal face. The protrusions and recess of proximal-most foldable member 2608 may comprise any of the protrusion and recess geometries described herein.

Figure 27:
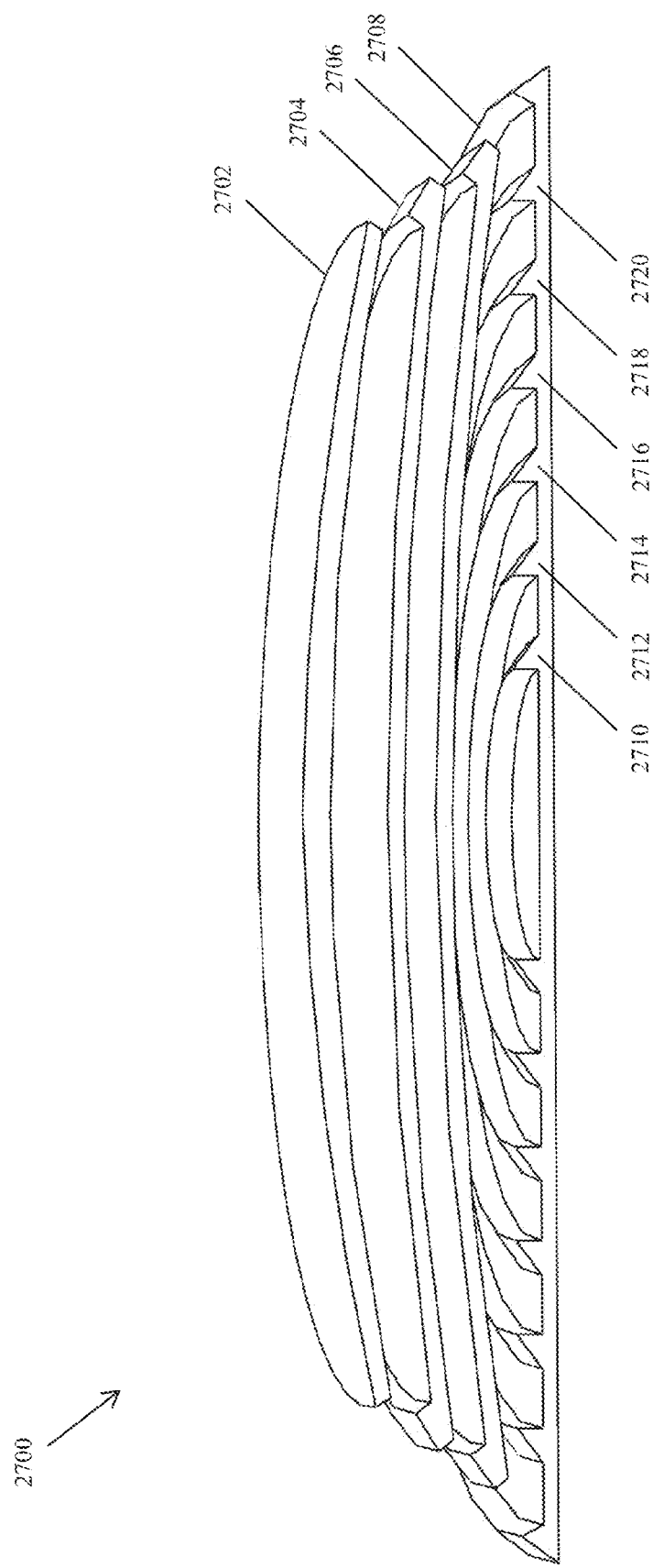
FIG. 27 is a cross-sectional perspective view of another example of a multi-disc anchor.

FIG. 27 depicts a cut-away, exploded view of a distal anchor 2700 comprising distal-most foldable member 2702, first inner foldable member 2704, second inner foldable member 2706, and proximal-most foldable member 2708. Foldable members 2702-2708 may have less curvature than the foldable members described above with respect to distal anchor 2500. In addition, inner foldable members 2704 and 2706 may have recesses configured to receive a proximal surface of the distally adjacent foldable member and protruding outer regions configured to relatively restrain the distally adjacent foldable members, similar to the inner foldable members in distal anchors 2500 and 2600. The recesses and protruding outer regions of inner foldable members 2704 and 2706 may take any of the geometries described above with respect to distal anchors 2704 and 2706.

Proximal-most foldable member comprises annular ribs 2710, 2712, 2714, 2718, and 2720. Annular ribs 2710, 2712, 2714, 2718, and 2720 may provide a separation between the proximal-most foldable member 2708 and the second inner foldable member 2706 while also providing a resistance to relative motion between the two adjacent foldable members. Although six annular ribs are shown in FIG. 27, other variations may include other numbers of annular ribs, including 2, 3, 4, 5, 7, 8, 9 and 10 annular ribs. Further, although the annular ribs in FIG. 27 are concentric, in other variations the annular ribs are not concentric. Further, the annular ribs in FIG. 27 are separated by an equal distance, but in other variations, the annular ribs may be separated by different distances. The geometry of each annular rib may be characterized by an inner surface that is oriented approximately in parallel to the height dimension and an outer surface that is oriented at an angle to the height dimension, wherein the angle may sometimes be 0°, 10°, 20°, 30°, 40°, 50°, 60°, 70°, 80°, and 90°, or any range between any two of the above angles. In some variations, the height of the inner surface of each rib may be characterized as a percentage of the thickness of the proximal-most member without the ribs and may sometimes be 5%, 10%, 20%, 30%, 40%, 45%, 50%, 60%, 70%, 80%, 90%, or 95%, or any percentage range between any two of the above percentages. In other variations, the thickness of the proximal-most member without the ribs may be characterized as a percentage of the height of the inner surface of each rib and may sometimes be 5%, 10%, 20%, 30%, 40%, 45%, 50%, 60%, 70%, 80%, 90%, or 95%, or any percentage range between any two of the above percentages.

Figure 28:
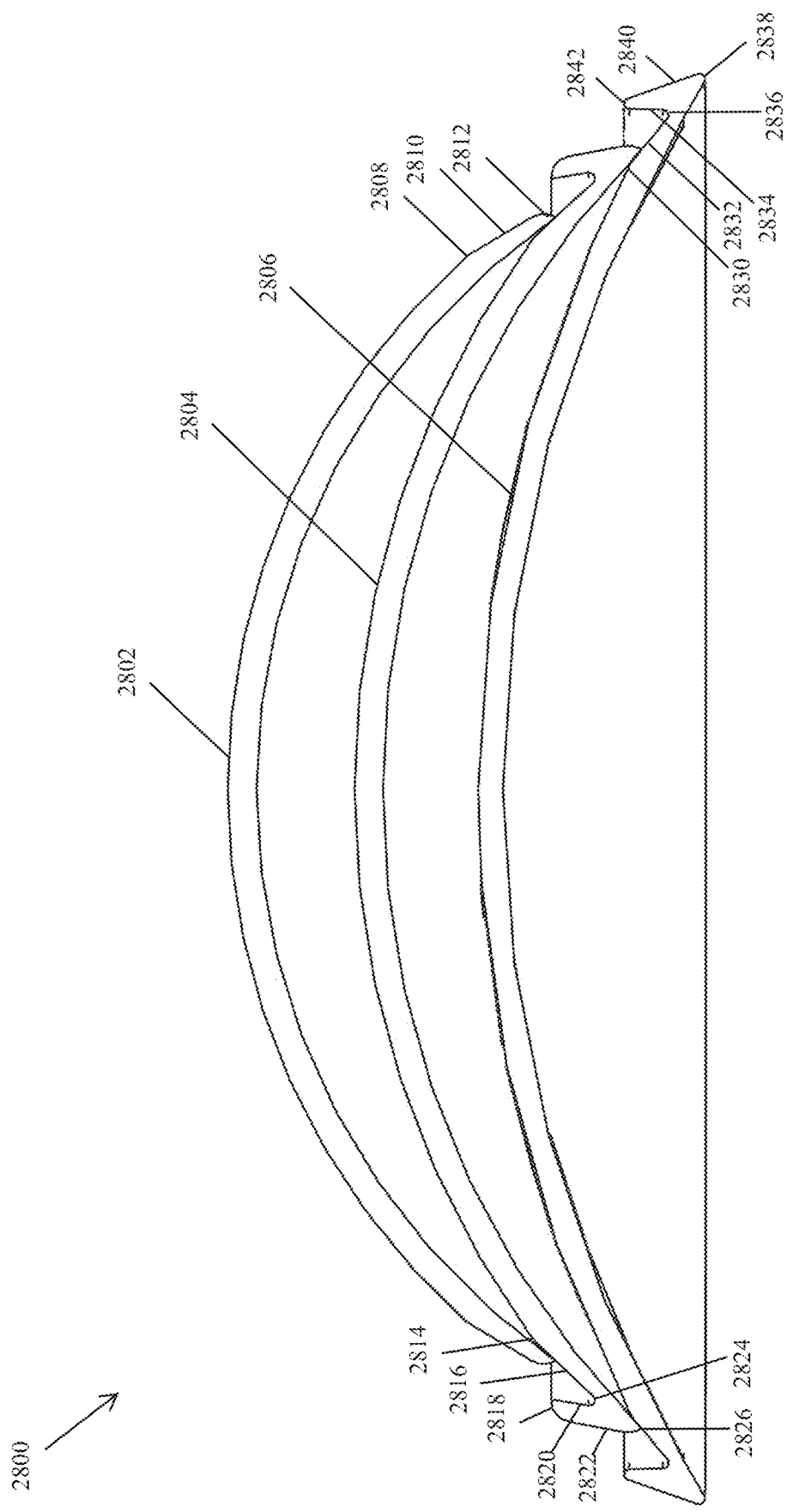
FIG. 28 is a cross-sectional elevational view of another example of a multi-disc anchor.

FIG. 28 depicts a cross-sectional exploded view of a distal anchor 2800 comprising distal-most foldable member 2802, inner foldable member 2804, and proximal-most foldable member 2806. Foldable members 2802, 2804, and 2806 may have greater curvature than the foldable members of distal anchors 2500, 2600, and 2700. In addition, a proximal protrusion on inner foldable member 2804 and proximal-most foldable member 2806 may protrude further than the proximal protrusions of distal anchors 2500, 2600, and 2700. Inner foldable member 2804 also include a recess at the base of the proximal protrusion to improve mating to the distally adjacent foldable member. Further, the distal surface of distal-most foldable member 2802 may be tapered at its perimeter to improve mating with proximal-most foldable member 2802.

Distal-most foldable member 2802 includes an outer region on its distal surface which may be tapered to improve mating. The outer region includes a distal angular region 2808, a planar surface 2810, and a proximal angular region 2812. Distal angular region 2808 may create an obtuse angle where the distal surface of distal-most foldable member 2802 and planar surface 2810 meet. In some variations, the angle may sometimes be 90°, 100°, 110°, 120°, 130°, 140°, 150°, 160°, 170°, and 180°, or any range between any two of the above angles. Proximal angular region 2812 may be an arc with a radius and an angle. In some variations, the radius is characterized as a percentage of the thickness of the distal-most foldable member, and may sometimes be 5%, 10%, 20%, 30%, 40%, 45%, 50%, 60%, 70%, 80%, 90%, or 95%, or any percentage range between any two of the above percentages. In some variations, the thickness of the distal-most foldable member is characterized as a percentage of the radius of proximal angular region 2812, and may sometimes be 5%, 10%, 20%, 30%, 40%, 45%, 50%, 60%, 70%, 80%, 90%, or 95%, or any percentage range between any two of the above percentages. In some variations, the angle of proximal angular region 2812 may be 0°, 10°, 20°, 30°, 40°, 50°, 60°, 70°, 80°, 90°, 100°, 110°, 120°, 130°, 140°, 150°, 160°, 170°, 180°, or any range between any two of the above angles. In some variations, the length of planar surface 2810 is characterized as a percentage of the thickness of the distal-most foldable member, and may sometimes be 5%, 10%, 20%, 30%, 40%, 45%, 50%, 60%, 70%, 80%, 90%, or 95%, or any percentage range between any two of the above percentages. In some variations, the thickness of the distal-most foldable member is characterized as a percentage of the length of planar surface 2810, and may sometimes be 5%, 10%, 20%, 30%, 40%, 45%, 50%, 60%, 70%, 80%, 90%, or 95%, or any percentage range between any two of the above percentages.

Inner foldable member 2804 includes an outer region on its distal surface which comprises a protrusion and a recess. The recess comprises a distal angular region 2814, a first planar surface 2816, a proximal angular region 2824, and a second planar surface 2820. Distal angular region 2814 may create an obtuse angle where the distal surface of inner foldable member 2804 and first planar surface 2816 meet. In some variations, the angle may sometimes be 90°, 100°, 110°, 120°, 130°, 140°, 150°, 160°, 170°, and 180°. In some variations, the length of first planar surface 2816 is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the length of first planar surface 2816, and may sometimes be 5%, 10%, 20%, 30%, 40%, 45%, 50%, 60%, 70%, 80%, 90%, or 95%, or any percentage range between any two of the above percentages. Proximal angular region 2824 may be an arc with a radius and an angle. In some variations, the radius is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the radius of proximal angular region 2824, and may sometimes be 5%, 10%, 20%, 30%, 40%, 45%, 50%, 60%, 70%, 80%, 90%, or 95%, or any percentage range between any two of the above percentages. In some variations, the angle of proximal angular region 2824 may be 0°, 10°, 20°, 30°, 40°, 50°, 60°, 70°, 80°, 90°, 100°, 110°, 120°, 130°, 140°, 150°, 160°, 170°, and 180°, or any range between any two of the above angles. In some variations, the length of second planar surface 2820 is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the length of second planar surface 2820, and may sometimes be 5%, 10%, 20%, 30%, 40%, 45%, 50%, 60%, 70%, 80%, 90%, or 95%, or any percentage range between any two of the above percentages. The protrusion on the outer region of inner foldable member 2804 comprises a distal angular region 2818, a planar surface 2822, and a proximal angular region 2826. Distal angular region 2818 may be an arc with a radius and an angle. In some variations, the radius is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the radius of distal angular region 2818, and may sometimes be 5%, 10%, 20%, 30%, 40%, 45%, 50%, 60%, 70%, 80%, 90%, or 95%, or any percentage range between any two of the above percentages. In some variations, the angle of distal angular region 2818 may be 0°, 10°, 20°, 30°, 40°, 50°, 60°, 70°, 80°, 90°, 100°, 110°, 120°, 130°, 140°, 150°, 160°, 170°, 180°, or any range between any two of the above angles. In some variations, the length of planar surface 2822 is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the length of planar surface 2822, and may sometimes be 5%, 10%, 20%, 30%, 40%, 45%, 50%, 60%, 70%, 80%, 90%, or 95%, or any percentage range between any two of the above percentages. Proximal angular region 2820 may be an arc with a radius and an angle. In some variations, the radius is characterized as a percentage of the thickness of the inner foldable member, and may sometimes be 5%, 10%, 20%, 30%, 40%, 45%, 50%, 60%, 70%, 80%, 90%, or 95%, or any percentage range between any two of the above percentages. In some variations, the thickness of the inner foldable member is characterized as a percentage of the radius of proximal angular region 2820, and may sometimes be 5%, 10%, 20%, 30%, 40%, 45%, 50%, 60%, 70%, 80%, 90%, or 95%, or any percentage range between any two of the above percentages. In some variations, the angle of proximal angular region 2820 may be 0°, 10°, 20°, 30°, 40°, 50°, 60°, 70°, 80°, 90°, 100°, 110°, 120°, 130°, 140°, 150°, 160°, 170°, 180°, or any range between any two of the above angles.

Proximal-most foldable member 2806 includes an outer region on its distal surface which comprises a protrusion and a recess. The recess comprises a distal angular region 2830, a first planar surface 2832, a proximal angular region 2836, and a second planar surface 2834. Distal angular region 2830 may create an obtuse angle where the distal surface of proximal-most foldable member 2806 and first planar surface 2832 meet. In some variations, the angle may sometimes be 90°, 100°, 110°, 120°, 130°, 140°, 150°, 160°, 170°, and 180°, or any range between any two of the above angles. In some variations, the length of first planar surface 2832 is characterized as a percentage of the thickness of the proximal-most foldable member, and may sometimes be 5%, 10%, 20%, 25%, 30%, 35%, 40%, 45%, 50%, 55%, 60%, 65%, 70%, 75%, 80%, 85%, 90%, or 95%. In some variations, the thickness of the proximal-most foldable member is characterized as a percentage of the length of first planar surface 2832, and may sometimes be 5%, 10%, 20%, 25%, 30%, 35%, 40%, 45%, 50%, 55%, 60%, 65%, 70%, 75%, 80%, 85%, 90%, or 95%. Proximal angular region 2836 may be an arc with a radius and an angle. In some variations, the radius is characterized as a percentage of the thickness of the proximal-most foldable member, and may sometimes be 5%, 10%, 20%, 25%, 30%, 35%, 40%, 45%, 50%, 55%, 60%, 65%, 70%, 75%, 80%, 85%, 90%, or 95%. In some variations, the thickness of the proximal-most foldable member is characterized as a percentage of the radius of proximal angular region 2836, and may sometimes be 5%, 10%, 20%, 30%, 40%, 45%, 50%, 60%, 70%, 80%, 90%, or 95%, or any percentage range between any two of the above percentages. In some variations, the angle of proximal angular region 2836 may be 0°, 10°, 20°, 30°, 40°, 50°, 60°, 70°, 80°, 90°, 100°, 110°, 120°, 130°, 140°, 150°, 160°, 170°, and 180°. In some variations, the length of second planar surface 2834 is characterized as a percentage of the thickness of the proximal-most foldable member, and may sometimes be 5%, 10%, 20%, 25%, 30%, 35%, 40%, 45%, 50%, 55%, 60%, 65%, 70%, 75%, 80%, 85%, 90%, or 95%. In some variations, the thickness of the proximal-most foldable member is characterized as a percentage of the length of second planar surface 2834, and may sometimes be 5%, 10%, 20%, 30%, 40%, 45%, 50%, 60%, 70%, 80%, 90%, or 95%, or any percentage range between any two of the above percentages. The protrusion on the outer region of proximal-most foldable member 2806 comprises a distal angular region 2842, a planar surface 2840, and a proximal angular region 2838. Distal angular region 2842 may be an arc with a radius and an angle. In some variations, the radius is characterized as a percentage of the thickness of the proximal-most foldable member, and may sometimes be 5%, 10%, 20%, 30%, 40%, 45%, 50%, 60%, 70%, 80%, 90%, or 95%, or any percentage range between any two of the above percentages. In some variations, the thickness of the proximal-most foldable member is characterized as a percentage of the radius of distal angular region 2842, and may sometimes be 5%, 10%, 20%, 30%, 40%, 45%, 50%, 60%, 70%, 80%, 90%, or 95%, or any percentage range between any two of the above percentages. In some variations, the angle of distal angular region 2842 may be 0°, 10°, 20°, 30°, 40°, 50°, 60°, 70°, 80°, 90°, 100°, 110°, 120°, 130°, 140°, 150°, 160°, 170°, 180°, or any range between any two of the above angles. In some variations, the length of planar surface 2840 is characterized as a percentage of the thickness of the proximal-most foldable member, and may sometimes be 5%, 10%, 20%, 30%, 40%, 45%, 50%, 60%, 70%, 80%, 90%, or 95%, or any percentage range between any two of the above percentages. In some variations, the thickness of the proximal-most foldable member is characterized as a percentage of the length of planar surface 2840, and may sometimes be 5%, 10%, 20%, 30%, 40%, 45%, 50%, 60%, 70%, 80%, 90%, or 95%, or any percentage range between any two of the above percentages. Proximal angular region 2838 may be an arc with a radius and an angle. In some variations, the radius is characterized as a percentage of the thickness of the proximal-most foldable member, and may sometimes be 5%, 10%, 20%, 30%, 40%, 45%, 50%, 60%, 70%, 80%, 90%, or 95%, or any percentage range between any two of the above percentages. In some variations, the thickness of the proximal-most foldable member is characterized as a percentage of the radius of proximal angular region 2838, and may sometimes be 5%, 10%, 20%, 30%, 40%, 45%, 50%, 60%, 70%, 80%, 90%, or 95%, or any percentage range between any two of the above percentages. In some variations, the angle of proximal angular region 2838 may be 0°, 10°, 20°, 30°, 40°, 50°, 60°, 70°, 80°, 90°, 100°, 110°, 120°, 130°, 140°, 150°, 160°, 170°, 180°, or any range between any two of the above angles.

Figure 29:
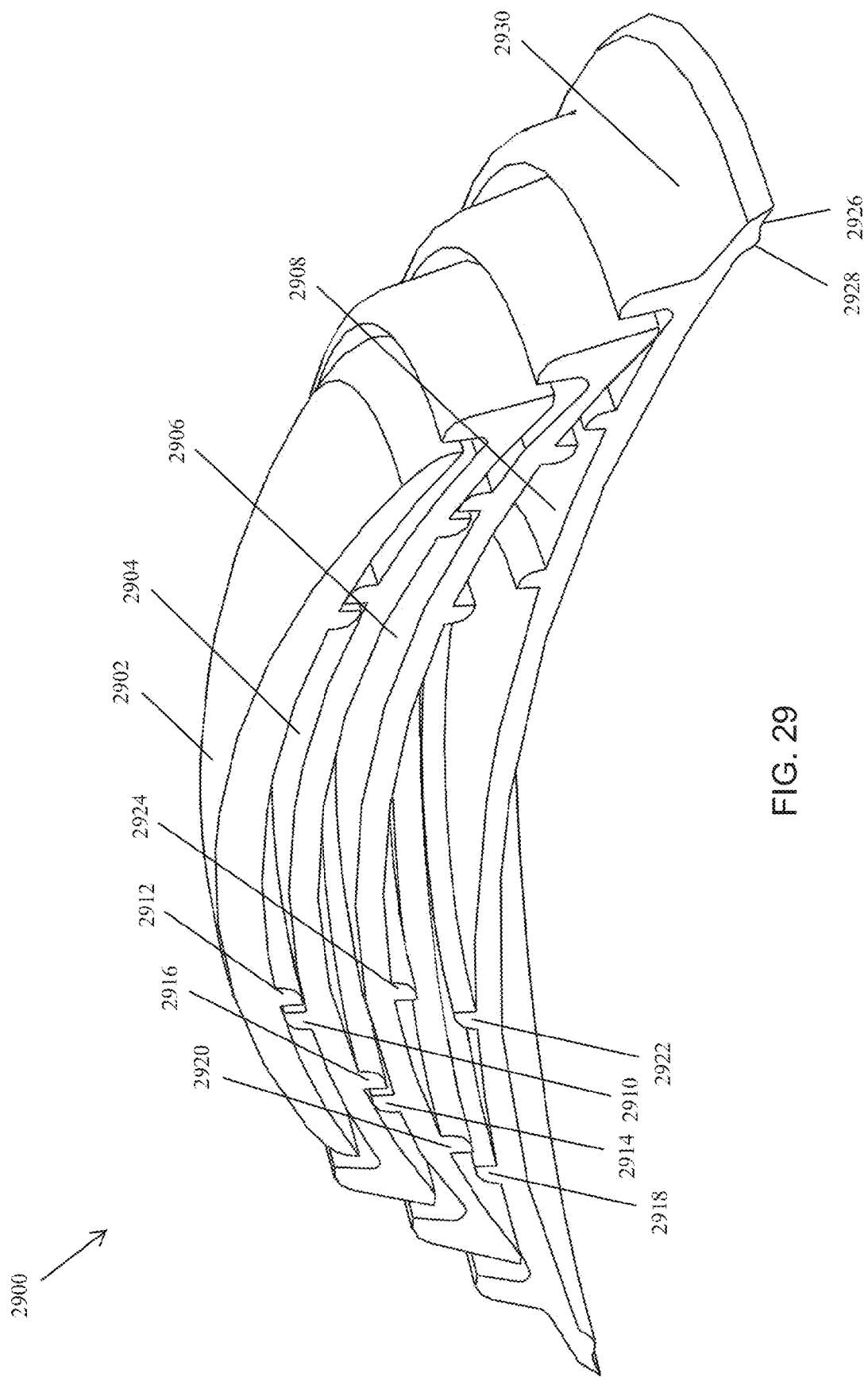
FIG. 29 is a cross-sectional perspective view of another example of a multi-disc anchor.

FIG. 29 depicts a cut-away, exploded view of a distal anchor 2900 comprising distal-most foldable member 2902, first inner foldable member 2904, second inner foldable member 2906, and proximal-most foldable member 2908. Distal-most foldable member 2902, first inner foldable member 2904, second inner foldable member 2906, and proximal-most foldable member 2908 may have less curvature than the foldable members of distal anchor 2800. Distal-most foldable member 2902 may a tapered outer region similar to the tapered outer region of distal-most foldable member 2802. First inner foldable member 2904, second inner foldable member 2906, and proximal-most foldable member 2908 may have recesses and protrusions in outer regions similar to those described above with respect to distal anchor 2800. The protrusion in the outer region of proximal-most foldable member 2908 may be located inward from the perimeter of proximal-most foldable member 2908, leaving a relatively thin region 2930 at the outermost part of proximal-most foldable member 2908. The position of the protrusion of the proximal-most foldable member may be characterized as a percentage of the diameter of proximal-most foldable member 2908, and sometimes may be 5%, 10%, 20%, 30%, 40%, 45%, 50%, 60%, 70%, 80%, 90%, or 95%, or any percentage range between any two of the above percentages. Proximal-most foldable member 2908 may also include features on its proximal surface configured to engage the surface of a body lumen. These features may be similar in geometry to curves 2544 and 2546 of distal anchor 2500. In addition, distal-most foldable member 2902, first inner foldable member 2904, second inner foldable member 2906, and proximal-most foldable member 2908 may comprise annular ribs 2910, 2912, 2914, 2916, 2918, 2920, 2922, and 2924 on their proximal and/or distal surfaces. These annular ribs may restrain relative movement of the foldable members when the foldable members are in the restrained configuration. Each annular rib has an associated annular rib on the opposing surface of the adjacent foldable member. As the foldable members are restrained by a suture (not shown), each pair of annular ribs are forced together, thereby limiting the relative movement between the adjacent foldable members. The opposing annular ribs may comprise parallel surfaces on their opposing faces. Annular ribs 2910, 2912, 2914, 2916, 2918, 2920, 2922, and 2924 may comprise a similar geometry as the annular ribs described above with respect to distal anchor 2700.

Figure 30:
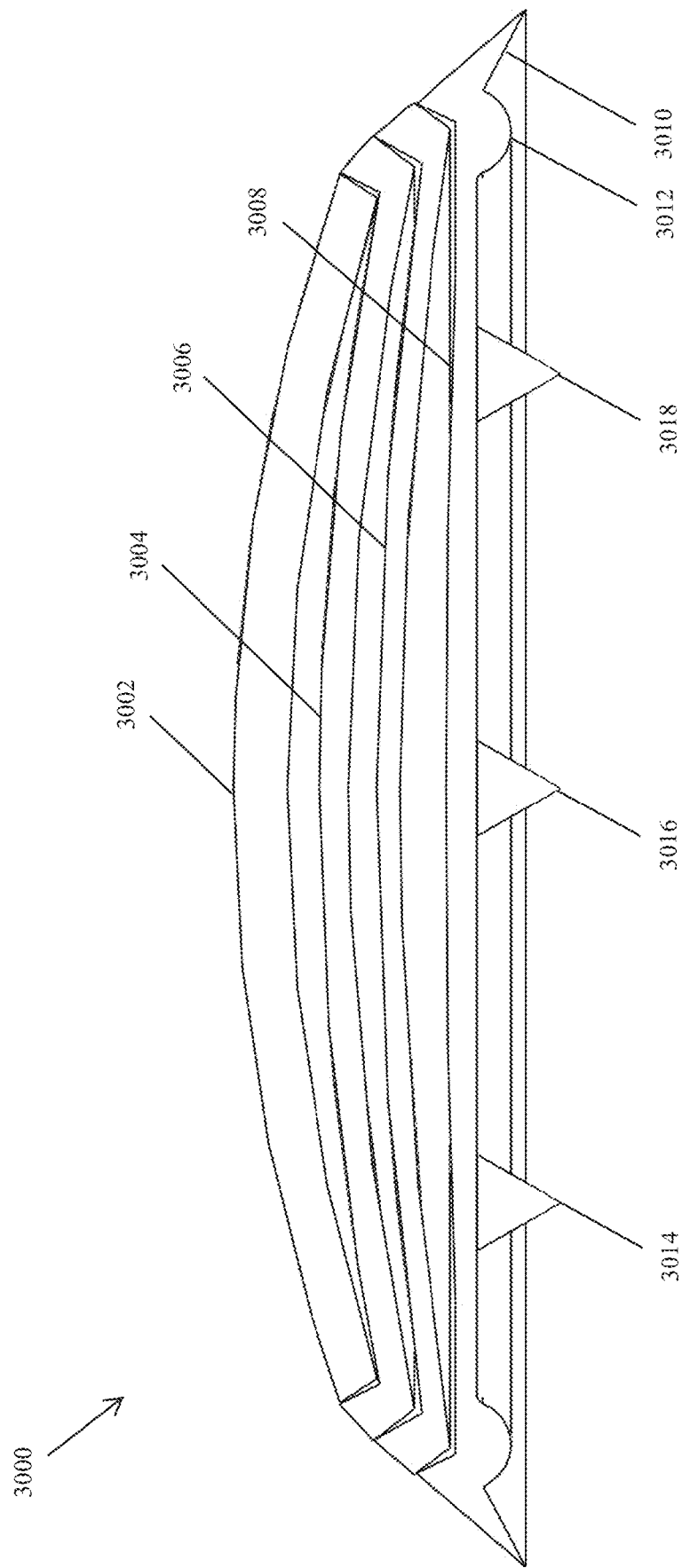
FIG. 30 is a cross-sectional elevational view of another example of a multi-disc anchor.

FIG. 30 depicts a cross-sectional view of a distal anchor 3000, comprising distal-most foldable member 3002, first inner foldable member 3004, second inner foldable member 3006, and proximal-most foldable member 3008. Distal-most foldable member 3002, first inner foldable member 3004, and second inner foldable member 3006 may comprise similar geometries to distal-most foldable member 1802, first inner foldable member 1804, and second inner foldable member 1806 discussed above with respect to distal anchor 1800. In some variations, as depicted in FIG. 30, the distal-most foldable member 3002, first inner foldable member 3004, and second inner foldable member 3006 may be curved. Distal-most foldable member 3002, first inner foldable member 3004, and second inner foldable member 3006 may have less curvature than the foldable members of distal anchor 2900. The proximal surface of proximal-most foldable member may be substantially planar. The distal surface of proximal-most foldable member 3008 may comprise an outer region with a protrusion 3012 similar to protrusion 2546 discussed above with respect to distal anchor 2500. Proximal-most foldable member 3008 may also comprise a flat surface 3010 connecting the edge of the proximal-most foldable member to protrusion 3012. The proximal surface of proximal-most member 3008 may also comprise grapples 3014, 3016, and 3018 configured to engage the surface of a body lumen and restrain the distal anchor 3000 with respect to the body lumen.

In some variations, one or more of grapples 3014, 3016, and 3018 may be omitted. In other variations, additional grapples are added.

Figure 31:
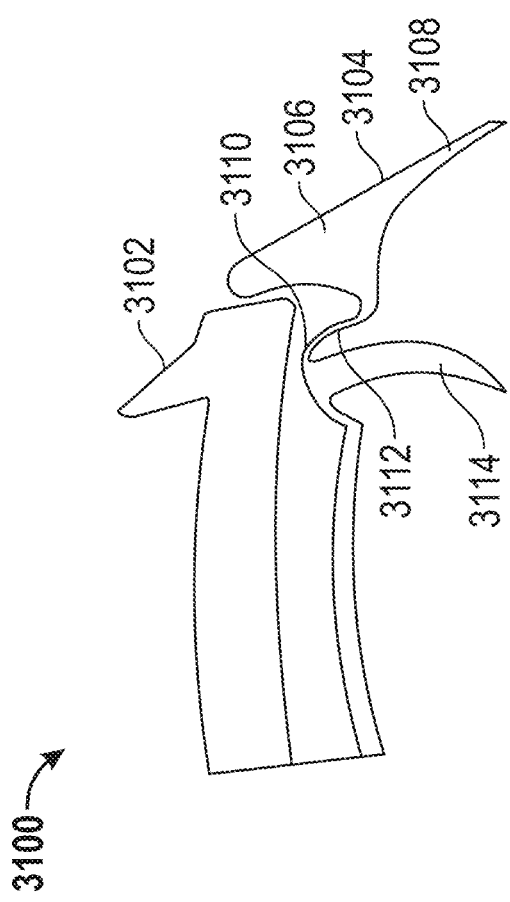
FIG. 31 is a schematic cross-sectional view of a tissue support structure of another example of a multi-disc anchor.

FIG. 31 depicts a portion 3100 of a distal anchor comprising inner foldable member 3102 and proximal-most foldable member 3104. Inner foldable member 3102 may comprise a geometry similar to any of the inner foldable members described herein. Proximal-most foldable member 3104 may comprise a distal protrusion 3106 and outer region 3108. Distal protrusion 3106 may comprise a geometry similar to any of the protrusions described herein. Outer region 3108 may comprise a geometry similar to any of the outer regions of the proximal-most foldable members described herein. Proximal-most foldable member 3104 also comprises a moveable protrusion 3110 on its distal surface, a recess 3112 on its proximal surface, and a grapple 3114 on its proximal surface. Moveable protrusion 3110 and recess 3112 may be aligned to create a region of reduced thickness in proximal-most foldable member 3104. Recess 3112 and grapple 3114 may be interconnected so that grapple 3114 enters and grips the tissue of a body lumen as inner foldable member 3102 connects with proximal-most foldable member 3004. More specifically, as the proximal surface of inner foldable member 3102 engages with moveable protrusion 3110, the protrusion is forced proximally, thereby forcing distal recess 3112 proximally. Distal recess 3112 and grapple 3114 may be integrally coupled so that grapple 3114 moves proximally and inwardly as distal recess 3112 moves proximally. In this way, the proximal motion of inner foldable member 3102 is translated to a proximal and inward motion of grapple 3114, thereby facilitating entering and gripping of the tissue.

Protrusion 3110 is depicted as circular, but in some variations protrusion 3110 is non-circular. When circular, protrusion 3110 might be characterized as an arc with a radius that intersects the distal surface of an inner region of proximal-most foldable member 3104. In some variations, the radius of the arc is described as a percentage of the diameter of the proximal-most foldable member and may sometimes be 1%, 2%, 3%, 4%, 5%, 10%, 15%, 20%, 25%, 30%, or any percentage range between any two of the above percentages. In some variations, the arc does not have a constant radius. In some variations, protrusion 3110 may be less resistant to movement than surrounding areas of the proximal-most foldable member 3104. In this way, protrusion 3110 may be configured to move relative to the surrounding area of proximal-most foldable member. In some variations, the reduction in resistance to deformation is facilitated by a decrease in the thickness of the proximal-most foldable member 3104 in the area of the protrusion 3110. In other areas, the density of the material is reduced in the area of the protrusion 3110. Although FIG. 31 depicts proximal-most foldable member 3104 as comprising a single protrusion configured to move relative to the surrounding area, other variations may have any number of such protrusions, including 2, 3, 4, 5, 6, 7, 8, and 10 protrusion. Further, FIG. 31 illustrates a protrusion on the distal surface of proximal-most foldable member 3102, but some variations may include a protrusion on the proximal surface of inner foldable member 3102 and a flat surface or protrusion on the distal surface of proximal-most foldable member 3104.

Grapple 3114 is illustrated as being "fang" shaped, but in other embodiments grapple 3114 takes an alternative shape, such as a hook shape, that can puncture the surface of a body lumen. Grapple 3114 may comprise barbs oriented away from the direction of insertion, thereby preventing withdrawal of the fang after insertion. In some variations, the length of grapple 3114 is described as a percentage of the thickness of proximal-most foldable member 3104 from its distal-most point to its proximal-most point, and the percentage may sometimes be 5%, 10%, 20%, 30%, 40%, 45%, 50%, 60%, 70%, 80%, 90%, or 95%, or any percentage range between any two of the above percentages. In other variations, the thickness of proximal-most foldable member 3104 from its distal-most point to its proximal-most point is described as a percentage of the length of grapple 3114, and the percentage may sometimes be 5%, 10%, 20%, 30%, 40%, 45%, 50%, 60%, 70%, 80%, 90%, or 95%, or any percentage range between any two of the above percentages.

Although FIG. 31 illustrates protrusion 3110, recess 3112, and grapple 3114 positioned near an edge of foldable member 3104, other variations may have the grapple positioned at any location on proximal-most foldable member 3104. In some variations, the position of the protrusion 3110, recess 3112, and grapple 3114 is characterized as a percentage of the radius of the proximal-most member and may sometimes be 5%, 10%, 20%, 30%, 40%, 45%, 50%, 60%, 70%, 80%, 90%, or 95%, or any percentage range between any two of the above percentages. Further, although portion 3100 is described with an inner foldable member, a distal-most foldable member may replace inner foldable member 3102 without deviating from the scope of the disclosure.

FIG. 32 illustrates a delivery device 3200 configured to transport one or more foldable members through a fistula tract and into a body lumen. Delivery device 3200 may be configured to reduce the cross-sectional profile of the foldable members so that the foldable members can be inserted into elongate tubular member 3202 that has an internal diameter less than the diameter of the foldable members. Delivery device 3200 may also include a profile reduction member 3204 for reducing the cross-sectional profile of the foldable members to a width no more than the diameter of the elongate tubular member 3202. Once the foldable members are fully inserted into the elongate tubular member 3202, the tubular member may be passed through a fistula tract until the elongate tubular member is aligned with, or distal to, the distal opening of the fistula tract. The foldable members may then be pushed through the distal end of elongate tubular member 3202 or elongate tubular member 3202 may be withdrawn to deploy the foldable members in a body lumen.

The interior diameter of the elongate tubular member 3204 may be characterized as a percentage of the diameter of a proximal-most foldable member and may sometimes be 1%, 2%, 3%, 4%, 5%, 10%, 15%, 20%, 25%, or any percentage range between any two of the above percentages. In some variations, profile reduction member 3204 is integrally connected to elongate tubular member 3202 and in other variations it is configured to removably couple to the tubular member. In some variations, the size and shape of a profile reduction section may be configured for a specific foldable member. For example, a distal-most foldable member may require a different profile reduction section than a larger proximal-most foldable member.

FIG. 32 depicts a conical profile reduction member 3204. In some variations, the foldable member may be pushed through the conical profile reduction member by a rod. The rod may engage with the foldable member in the large dimension or the smaller dimension. For example, a rod may be used to push a foldable member on its proximal surface so that the distal surface is forced into the conical section. As the foldable member is forced further down the conical member and tubular member, the foldable member may assume a pleated configuration. Additional foldable members may then be inserted into the elongate tubular member.

In some variations, the profile member 3204 includes inner grooves or ridges to guide the foldable members into the delivery tube and control the folding. The grooves or ridges may be configured to interact with surface features on the foldable members, such as the surface features described above that are configured for relatively restraining two adjacent foldable members.

Figure 33A:
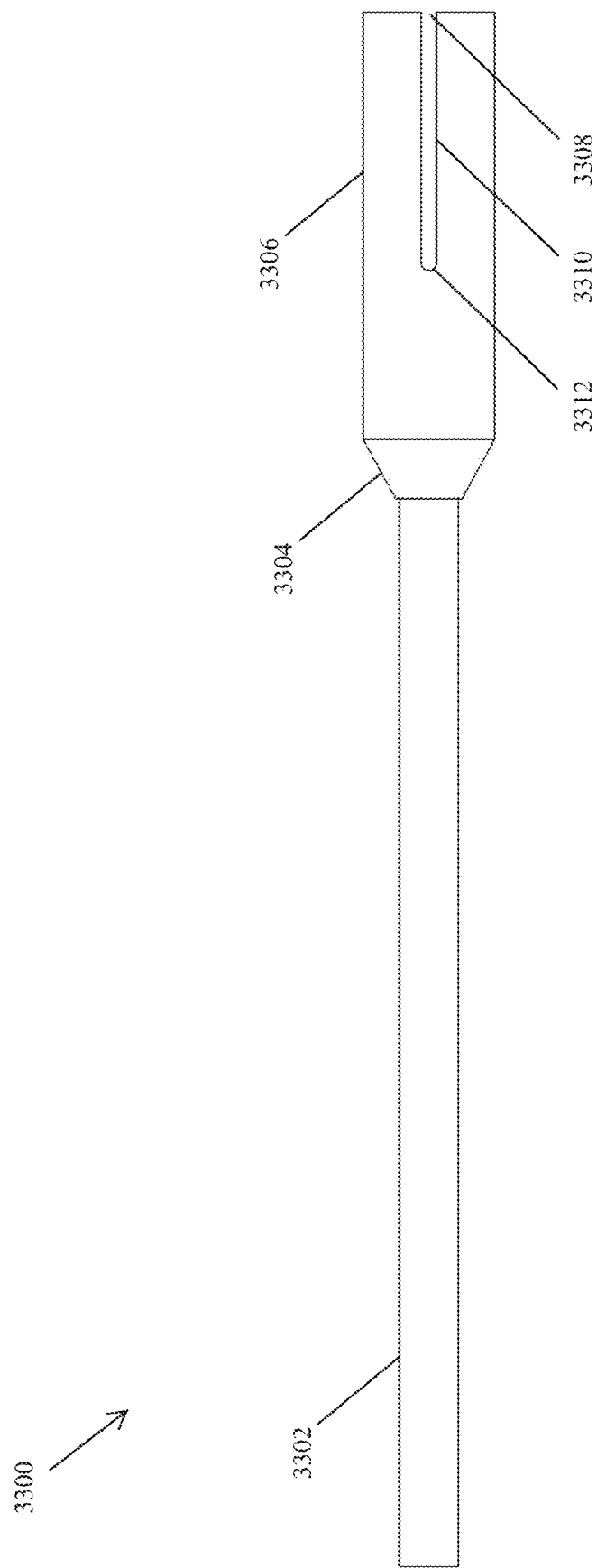
FIGS. 33A-33B are side elevational and superior perspective views, respectively, of a delivery device for a fistula treatment device.
Figure 33B:
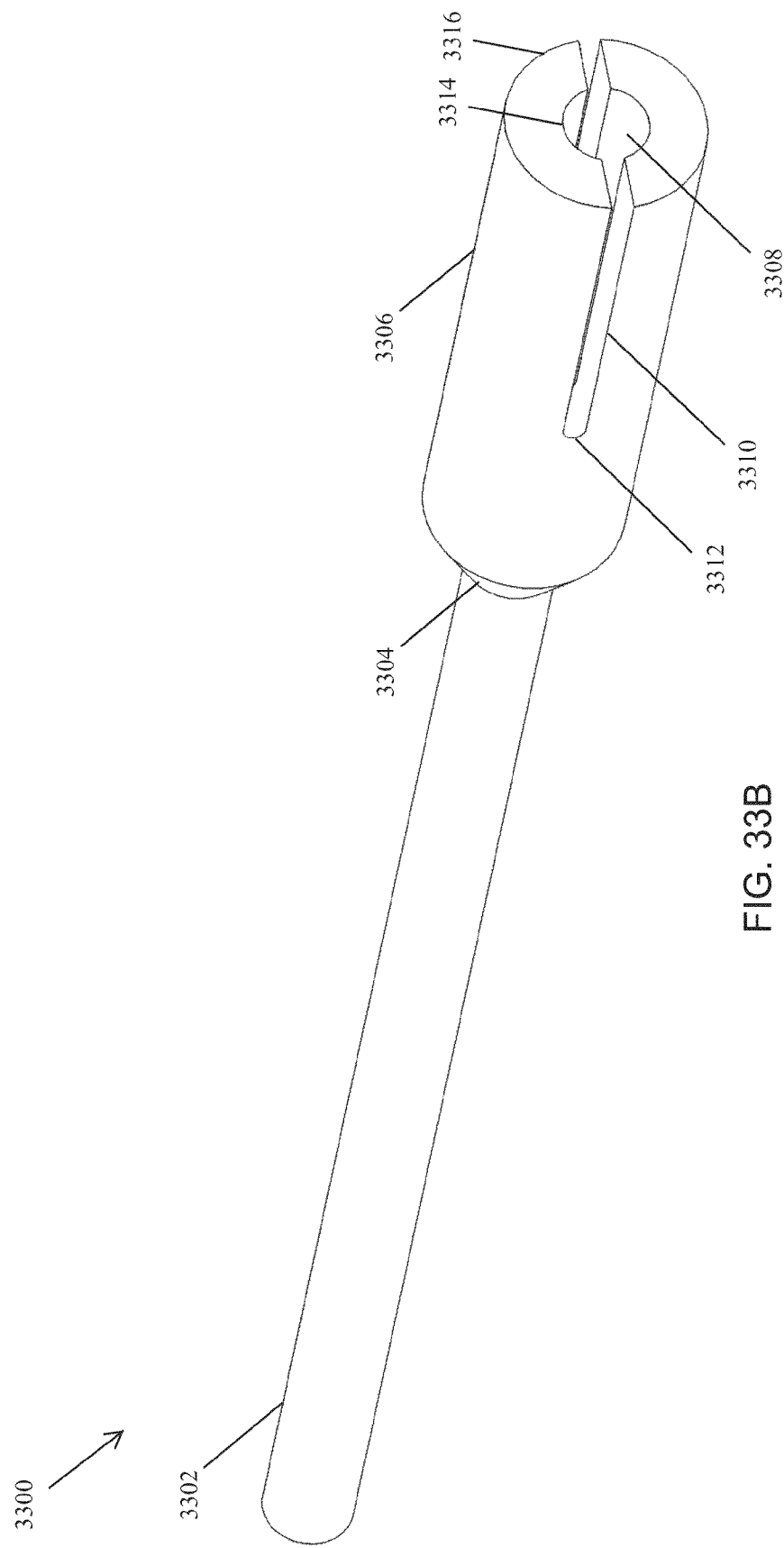

FIGS. 33A and 33B depict a side view and perspective view, respectively, of a rod 3300 configured to grasp a foldable member and insert the foldable member into a delivery device. Rod 3300 may generally comprise a handle 3302, a transition section 3304, and a distal head 3306. Distal head 3306 may comprise two elongate parallel slits 3310 configured to receive a foldable member. Each slit may have a distal opening 3308 and a curved proximal end 3312. The rod 3300 may be configured to reduce the profile of the foldable member by rotating the handle 3302 as the head 3306 pushes the foldable member into a profile reduction member. FIG. 33B illustrates the head with a hollow central tube. The hollow central tube may allow for additional folding in the central region of the foldable member. In some variations, the diameter of the central tube 3314 is characterized as a percentage of the diameter 3316 of distal head 3306 and may sometimes be 5%, 10%, 20%, 30%, 40%, 45%, 50%, 60%, 70%, 80%, 90%, or 95%, or any percentage range between any two of the above percentages. Curved proximal end 3312 may be configured to cradle a perimeter portion of a foldable member. In some variations, the lengths of the elongate slits are characterized as percentages of the length of the head 3306 and sometimes may be 5%, 10%, 20%, 30%, 40%, 45%, 50%, 60%, 70%, 80%, 90%, or 95%, or any percentage range between any two of the above percentages.

Figure 34B:
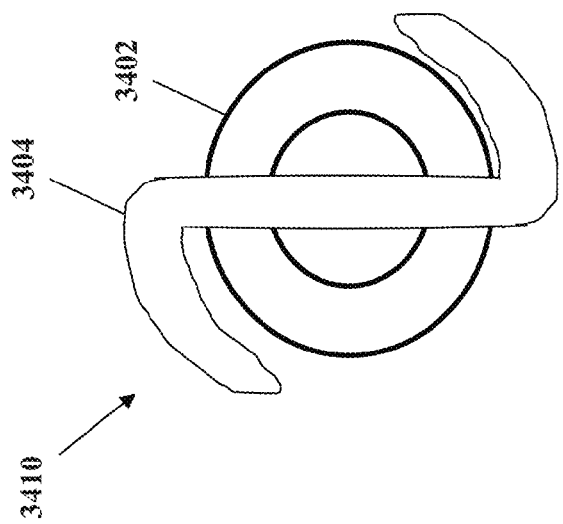
FIGS. 34A-34B are schematic illustrations of a fistula treatment device loaded into the delivery device in FIGS. 33A-33B, in an initial and a collapsed configuration, respectively.
Figure 34A:
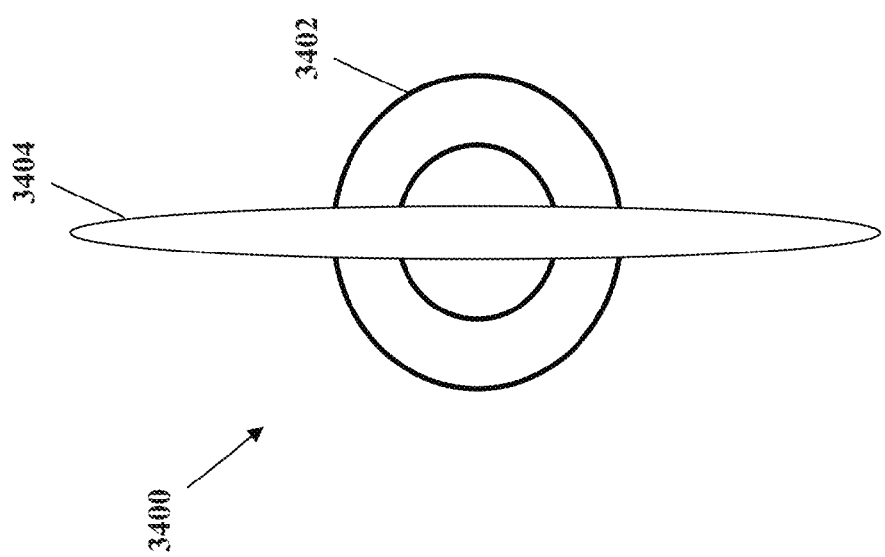

FIGS. 34A and 34B illustrate top views of a foldable member 3404 before 3400 and after 3410 it is folded for insertion. FIG. 34A illustrates the foldable member 3404 when it is inserted into the slots in the head 3402 of an insertion rod. FIG. 34B illustrates the foldable member 3404 after it has been pushed in a profile reduction member of a delivery device (not shown). The foldable member 3404 in the after configuration 3400 generally take a reverse "S" shape. In other variations, the foldable member takes a different shape, such as a spiral or a wave, for example.

Figure 35A:
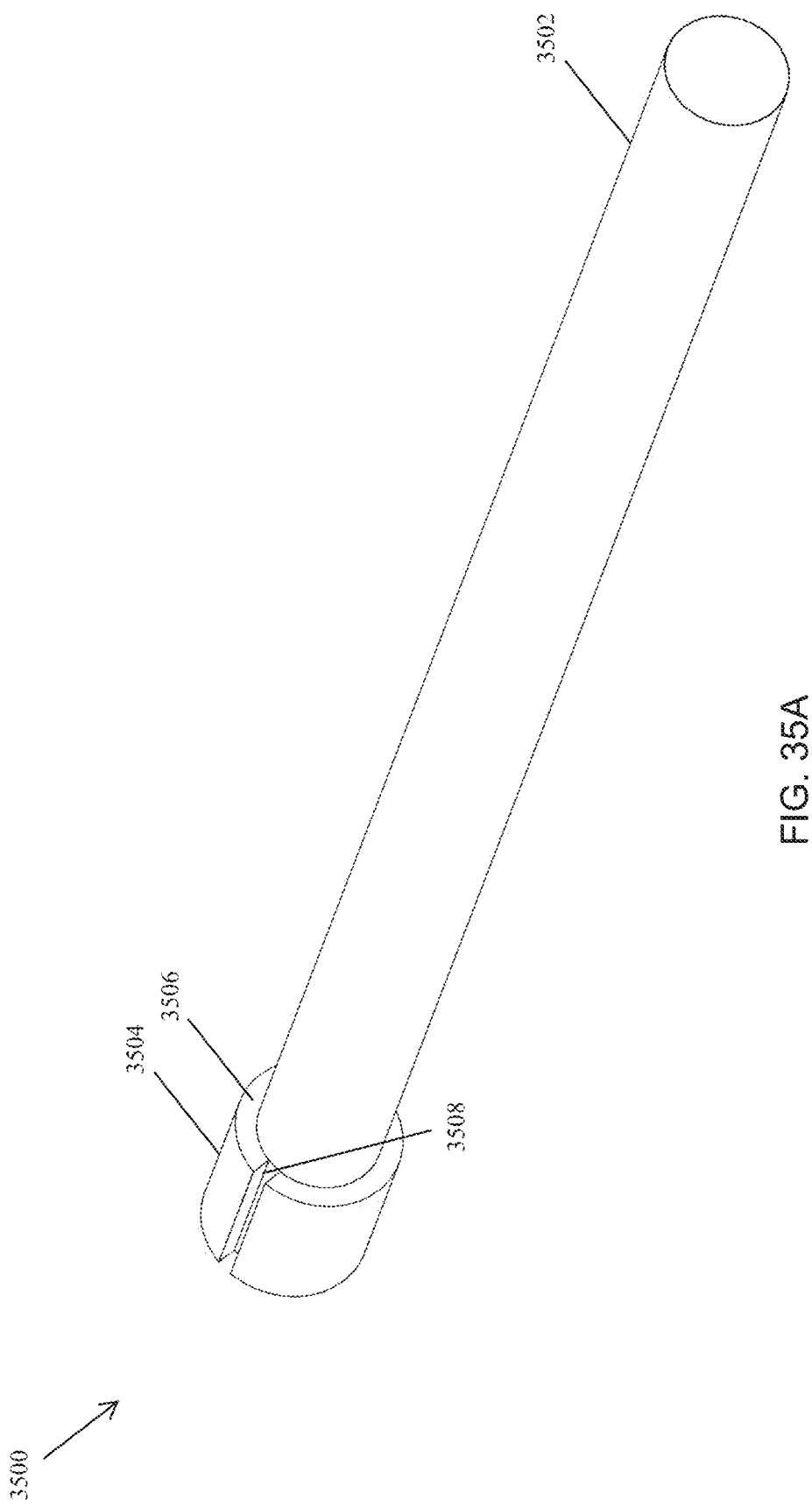
FIGS. 35A-35B are a superior perspective general view and a superior perspective distal detailed view of an exemplary push device for a fistula treatment device.
Figure 35B:
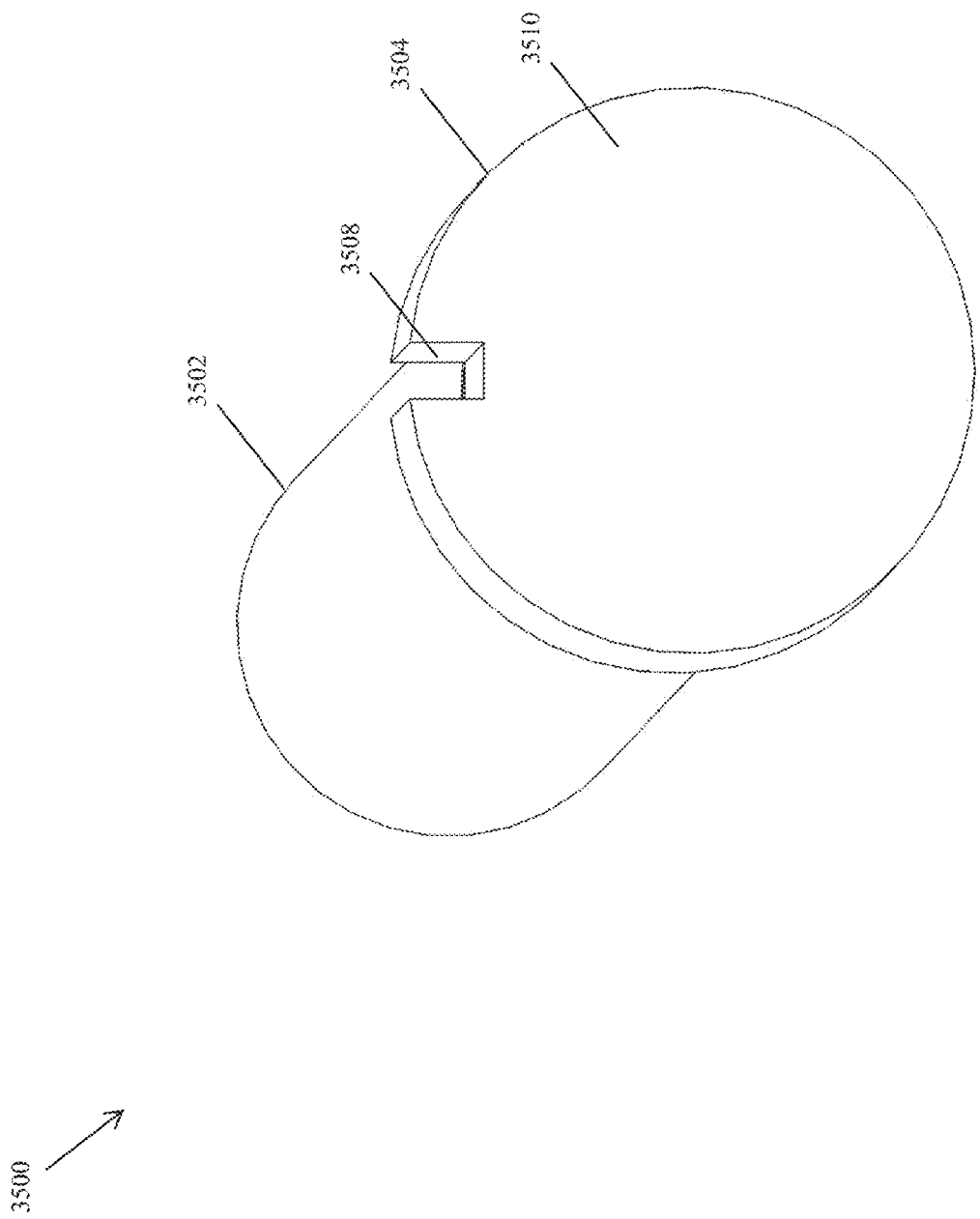

FIGS. 35A and 35B illustrate a proximal perspective view and a distal perspective view, respectively, of push device 3500. Push device 3500 may be configured to force one or more foldable members through a delivery tube. Push device 3500 may comprise a suture channel 3508 configured to permit a suture connected to a foldable member to be run axially to the push device while the foldable member is being inserted. Push device 3500 may comprise a handle 3502 and a distal head 3504. The diameter of distal head 3504 may be larger than the diameter of the handle 3502 to allow the suture to lie alongside the delivery tube. The diameter of the head 3504 may approximate the inside diameter of a desired delivery tube. FIG. 35B illustrates a distal perspective view of push device 3500, depicting a planar distal surface for pushing the foldable member through the delivery tube.

Figure 36A:
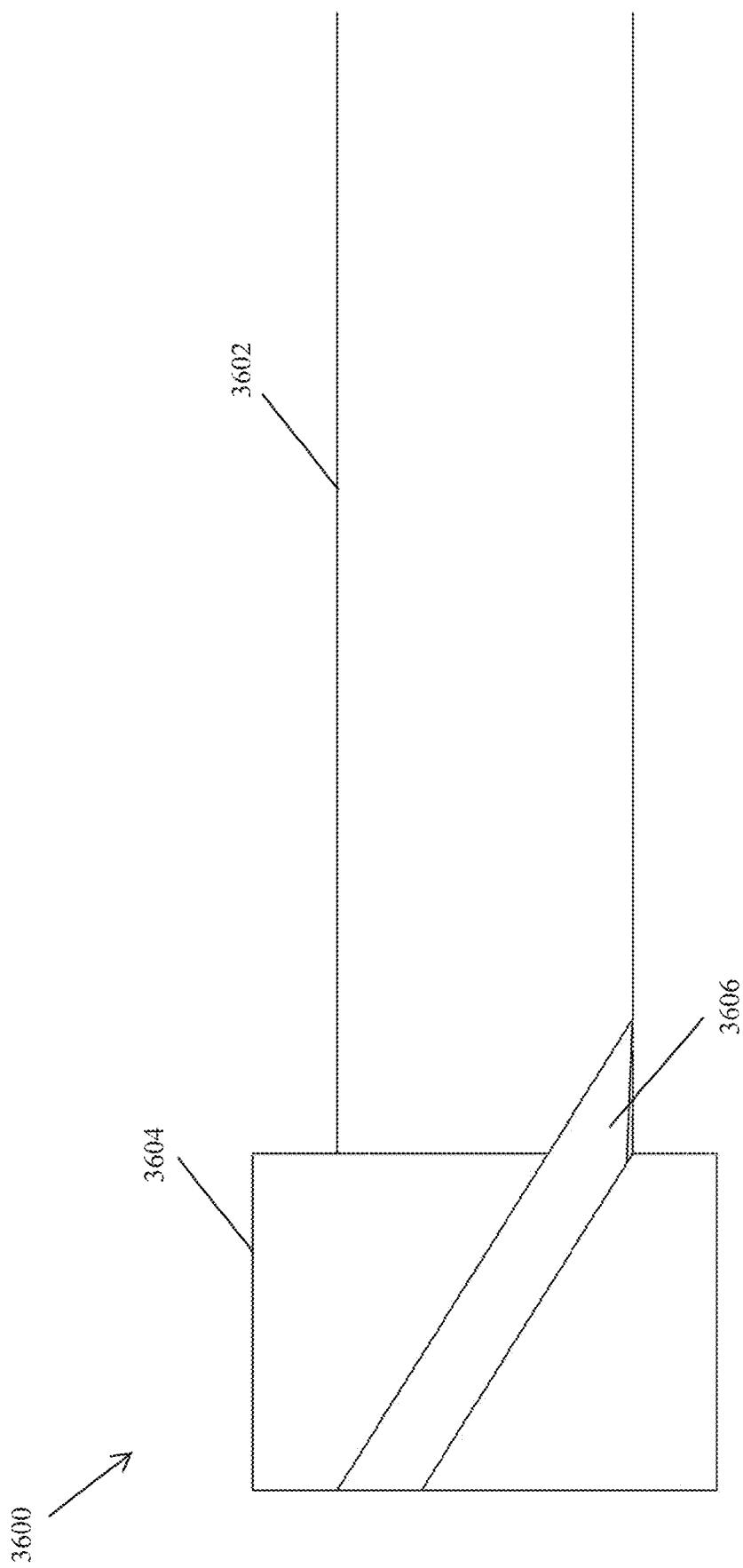
FIGS. 36A-36B are side elevational and superior perspective distal details views of another example of a push device for a fistula treatment device.
Figure 36B:
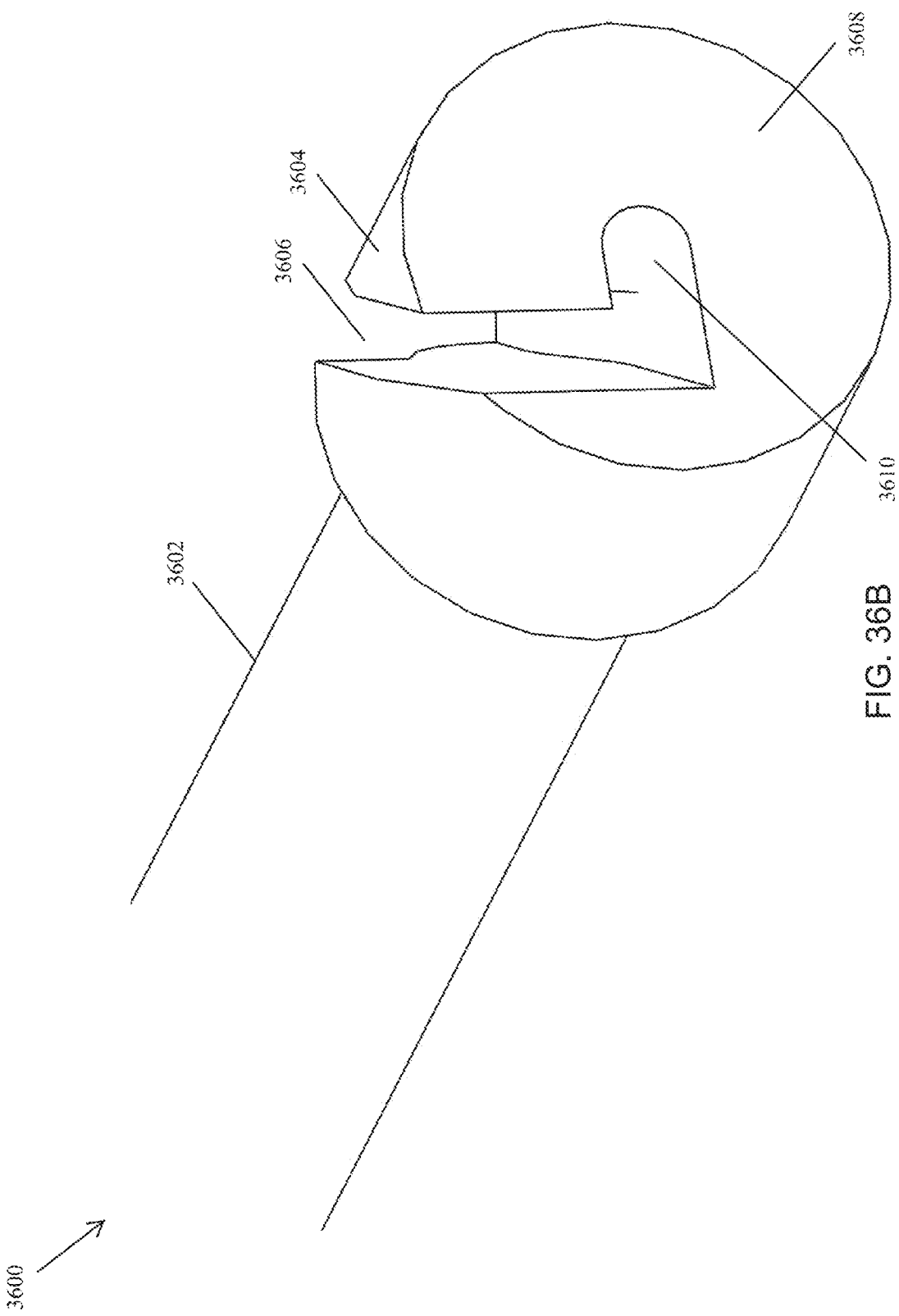

FIGS. 36A and 36B illustrate a side view and a distal perspective view, respectively, of push device 3600. Push device 3600 comprises a handle 3602 and a head 3604, similar to push device 3500. Push device 3600 may also comprise a suture channel 3606 configured to permit a suture connected to a foldable member to run axially to the push device during delivery. Suture channel 3506 may be oriented at an angle to the main axis of push device 3600, wherein the angle may be 0°, 10°, 20°, 30°, 40°, 50°, 60°, 70°, 80°, and 90°. Suture channel 3606 may also comprise a suture engagement structure 3610. The angle of suture channel 3606 and the suture engagement structure 3610 may allow push device to engage and lock the suture within the head 3604 as the push device moves through the delivery tube. Engagement and locking of the suture may be achieved by twisting the push device 3600.

Fistula tracts may be nonlinear or curvilinear and may contain cavities of varying sizes at different intervals within the tract. Fistulas may also comprise multiple interconnected or branching passages. A fistula treatment device disclosed herein may employ advantageous design, configuration techniques and attributes to accommodate such constraints and may be used, for example, in the treatment of anorectal fistulas. Some embodiments of fistula treatment devices may comprise irrigation and/or brushing devices which may be used, for example, to clean a fistula tract prior to, during, and/or after a procedure, and/or which may be used to clean a fistula tract prior to insertion of one or more implantable devices or other members (e.g., collagen plugs) therein.

Figure 37A:
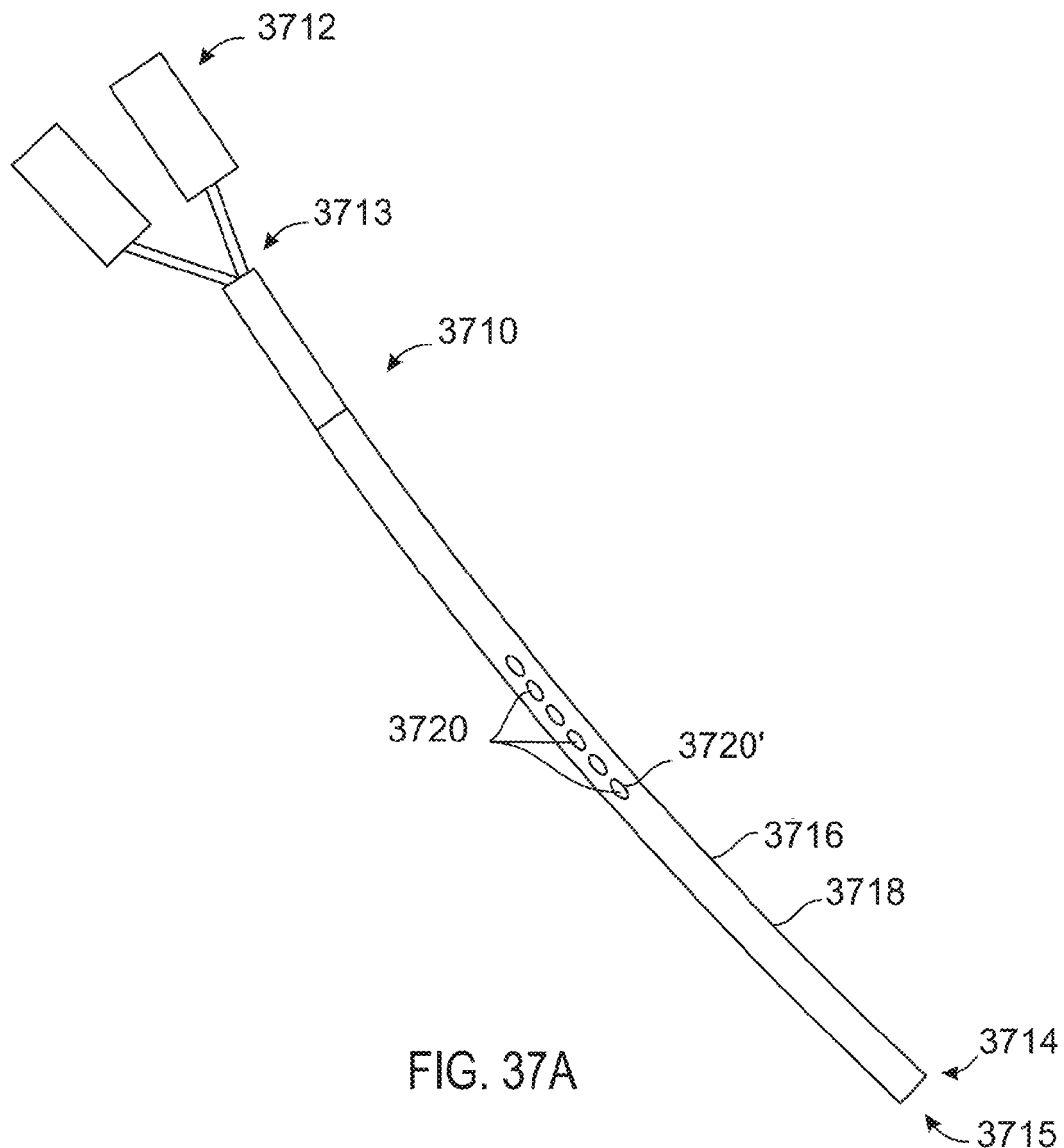
FIG. 37A is an illustrative depiction of an embodiment of a fistula irrigation catheter.

Referring to FIG. 37A, a fistula irrigation device (as shown, a fistula irrigation catheter 3710) comprises a proximal end 3712 and a distal end 3714. The fistula irrigation catheter further comprises a tubular member 3716 including a wall portion 3718 having a plurality of apertures 3720 therethrough. The tubular member has a proximal end 3713 and a distal end 3715. In some embodiments, the length of the tubular member (between the proximal end 3713 and the distal end 3715) may be in the range of about 20 centimeters to about 200 centimeters, such as about 40 centimeters to about 120 centimeters, about 40 centimeters to about 100 centimeters, or about 60 centimeters to about 90 centimeters.

The apertures 3720 may be used to irrigate a fistula tract—in other words, one or more irrigation fluids may flow through, or be sprayed or otherwise dispersed via, the apertures 3720. In some embodiments, the distalmost aperture 20' may be located at least about 2 centimeters (e.g., at least about 3 centimeters, at least about 4 centimeters, at least about 5 centimeters, at least about 10 centimeters, at least about 20 centimeters, at least about 30 centimeters, at least about 40 centimeters, at least about 50 centimeters, at least about 100 centimeters) from the distal end 3714 of the fistula irrigation catheter 3710. In other words, a fistula irrigation catheter may include apertures that are offset from the distal end of the catheter. This may be advantageous because it may, for example, provide for irrigation of a greater region of a fistula tract (e.g., both proximal and distal irrigation) than an irrigation catheter that only has an irrigation aperture at its distal end.

Figure 37B:
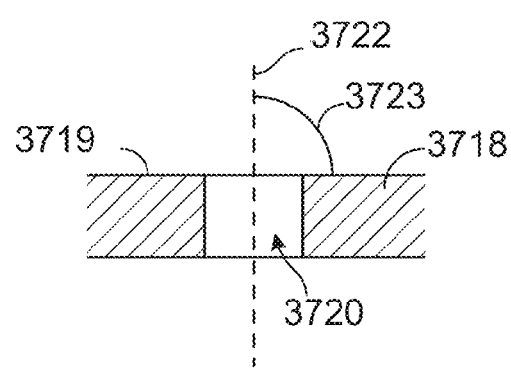
FIG. 37B is a cross-sectional view of a region of the fistula irrigation catheter of FIG. 37A, where the region includes an aperture.

FIG. 37B provides a cross-sectional view of an aperture 3720 in a region of the wall portion 3718. As shown there, the aperture 3720 has an axis 3722 therethrough that defines an angle 3723 relative to the exterior surface 3719 of the wall portion 3718. In FIG. 37B, the angle 3723 is shown as orthogonal (i.e., 90°)—however, in other embodiments, such an aperture angle may not be orthogonal. For example, the angle 3723 between an axis 3722 of an aperture 3720 and the exterior surface 3719 may be at least about 45° (e.g., at least about 60°, at least about 75°, at least about 90°, or from about 45° to about 180°, such as about 75°) relative to the distal end 14 of the catheter 3710, and/or may be at most about 180° (e.g., at most about 135°, at most about 120°, at most about 105°, or from about 45° to about 180°, such as about 75° to about 135°, or about 105°) relative to the proximal end 3712 of the catheter 3710.

While the apertures 3720 are depicted as generally oval or elliptical in shape, apertures in a fistula irrigation catheter may have any suitable shape, and may all be of the same shape or may have different shapes from each other. In some embodiments, an aperture may be circular, triangular, or square. Other appropriate shapes may also be used. Moreover, the apertures may all have the same size or may have different sizes (e.g., to provide differing amounts of irrigation to different regions of a fistula tract).

Figure 37C:
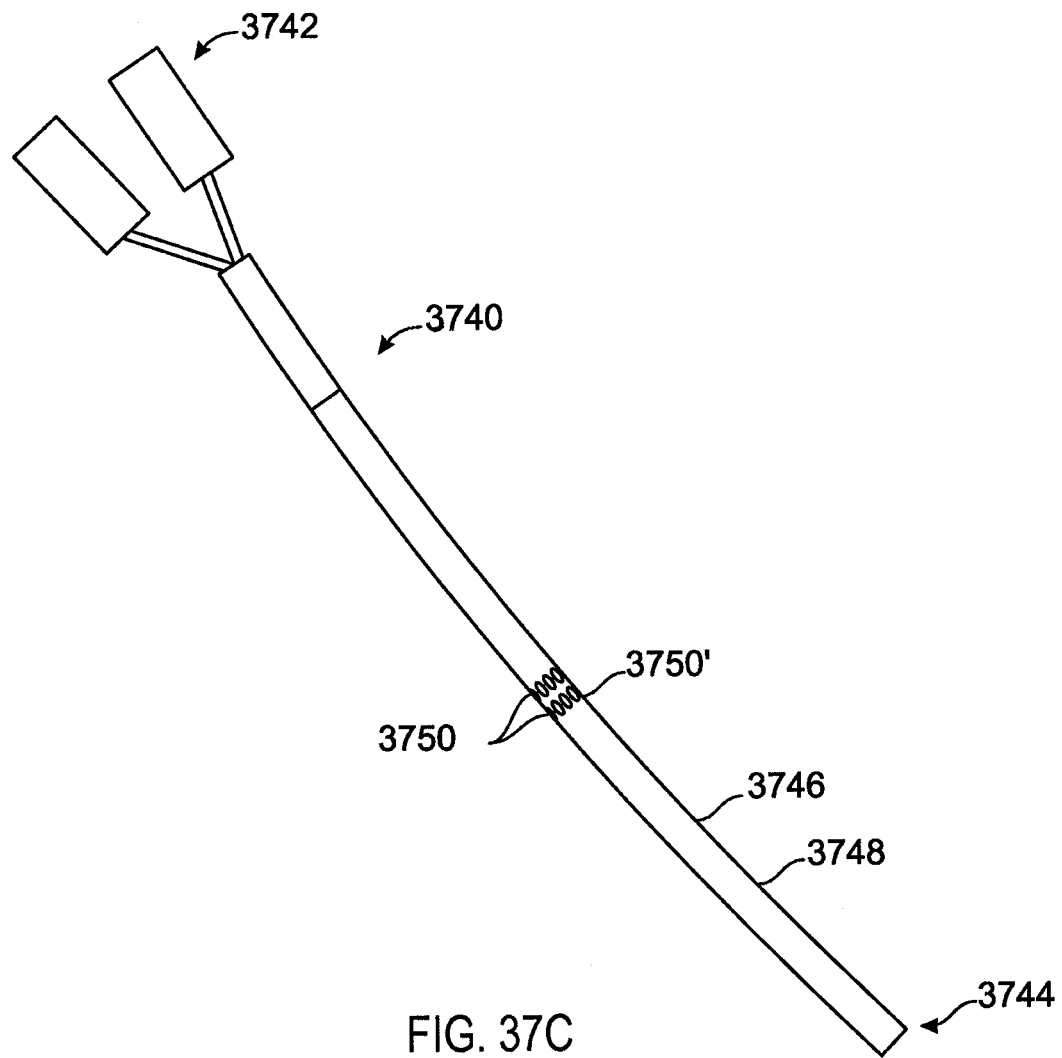
FIG. 37C is an illustrative depiction of another embodiment of a fistula irrigation catheter.
Figure 37D:
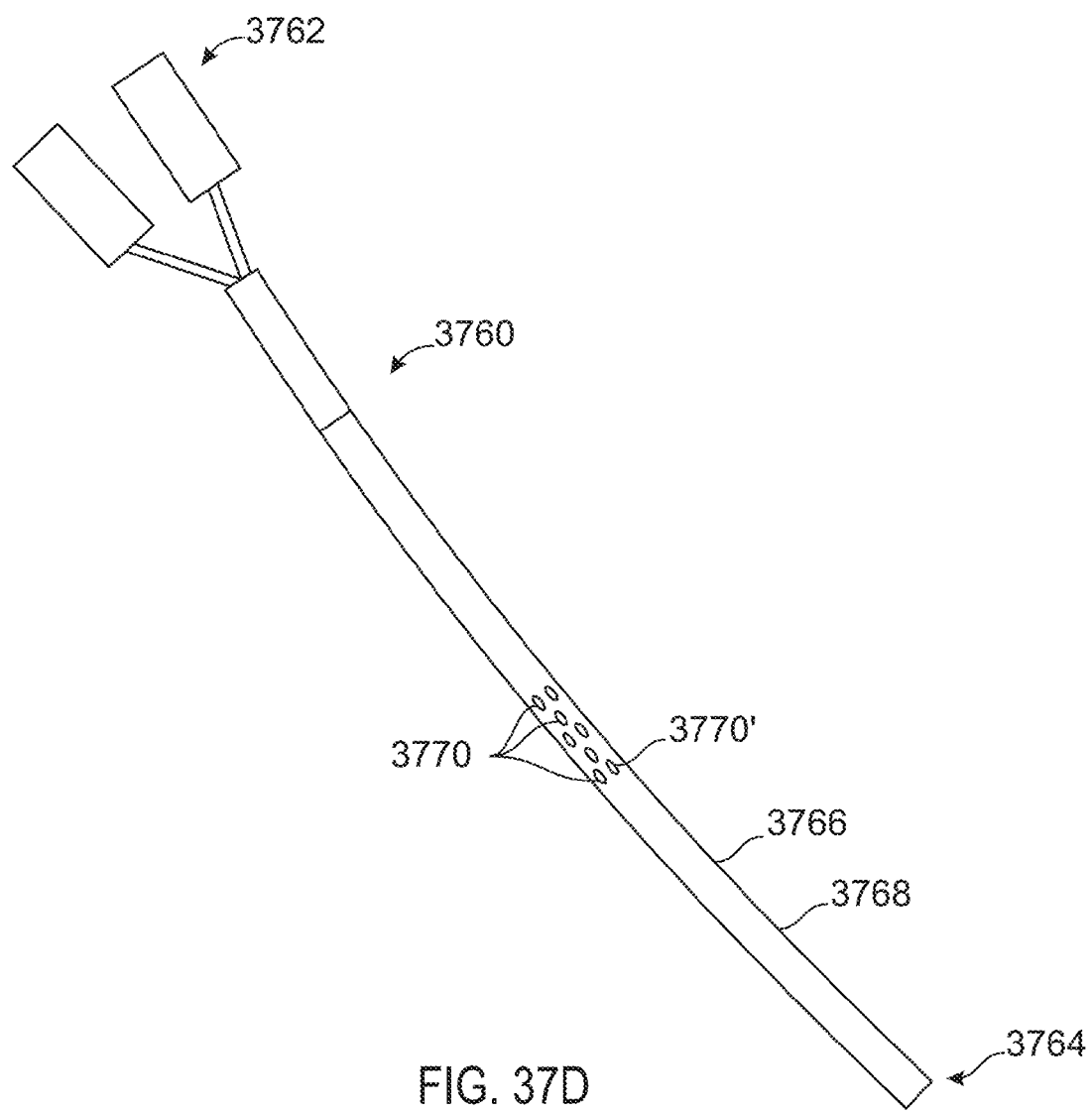
FIG. 37D is an illustrative depiction of an additional embodiment of a fistula irrigation catheter.

In some embodiments, apertures may be radially positioned around a fistula irrigation device. For example, FIG. 37C shows a fistula irrigation catheter 3740 having a proximal end 3742 and a distal end 3744, and comprising a tubular member 3746 having a wall portion 3748 having a plurality of radially disposed apertures 3750 therethrough, including distalmost apertures 3750'. As shown there, the apertures are arranged in two radial configurations. However, other embodiments of fistula irrigation catheters may have different arrangements and numbers of apertures. As an example, FIG. 37D shows a fistula irrigation catheter 3760 having a proximal end 3762 and a distal end 3764, and including a tubular member 3766 having a wall portion 3768. The tubular member 3766 has a plurality of apertures 3770 therethrough, including distalmost apertures 3770'. Of course, other configurations are possible, and any suitable number, size, shape and arrangement of apertures may be used in a fistula irrigation device.

In certain embodiments, apertures may be radially positioned around an irrigation catheter, and may be the distal termination points of radially oriented tubular members or lumens within the irrigation catheter. In some embodiments, a fistula irrigation device may comprise one or more infusion lumens that terminate at the location of one or more apertures in the device, such that the lumens do not extend any further distally, thereby avoiding creating "dead space" within the device. In certain embodiments, a fistula irrigation device may include one or more infusion lumens that extend distally beyond one or more apertures in the device; however, in some such embodiments, the infusion lumens may be plugged or otherwise filled distally of the apertures. In such cases, a guidewire lumen may be maintained open.

The tubular member 3716 of the fistula irrigation catheter 3710 may be relatively flexible in some embodiments and in certain embodiments, may include one or more relatively rigid regions. This may, for example, allow the tubular member 3716 to conform well to a tissue tract during use.

Figure 38A:
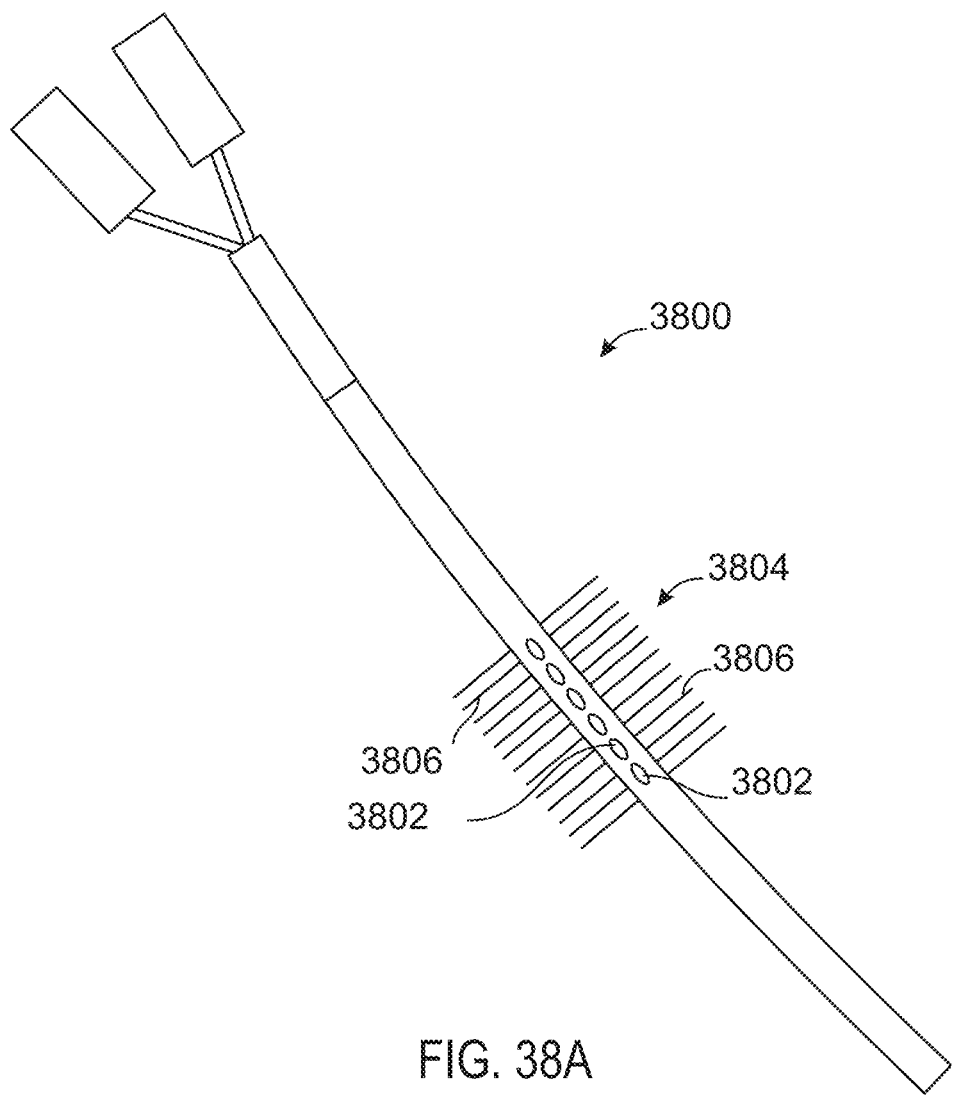
FIG. 38A is an illustrative depiction of an embodiment of a fistula irrigation and brushing catheter.

In certain embodiments, a fistula irrigation catheter may also have fistula brushing or debriding capabilities. As an example, FIG. 38A depicts a fistula irrigation and brushing catheter 3800. The catheter 3800 includes features similar to those described above with respect to the fistula irrigation catheter 3710, such as irrigation apertures 3802. However, the catheter 3800 also includes a brushing member 204 having bristles 3806. When the catheter 3800 is used to irrigate a fistula tract, it may also be used to brush or debride the fistula tract, thereby further cleaning the tract. In some cases, the bristles 3806 may be formed of one or more polymers. Other appropriate materials may also be used. In certain embodiments, a sheath or other protective member (not shown) may be removably positioned over a brushing member to, for example, temporarily prevent the brushing member from brushing tissue (e.g., non-target tissue).

Figure 38B:
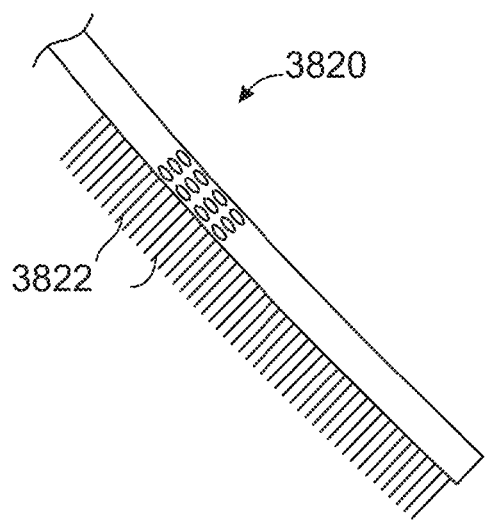
FIG. 38B is an illustrative depiction of a portion of another embodiment of a fistula irrigation and brushing catheter.
Figure 38C:
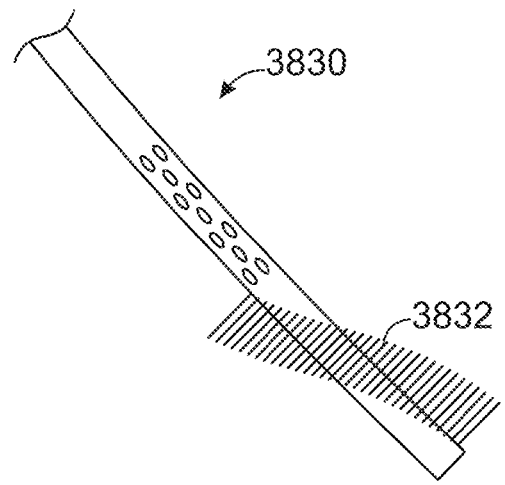
FIG. 38C is an illustrative depiction of a portion of an additional embodiment of a fistula irrigation and brushing catheter.
Figure 38D:
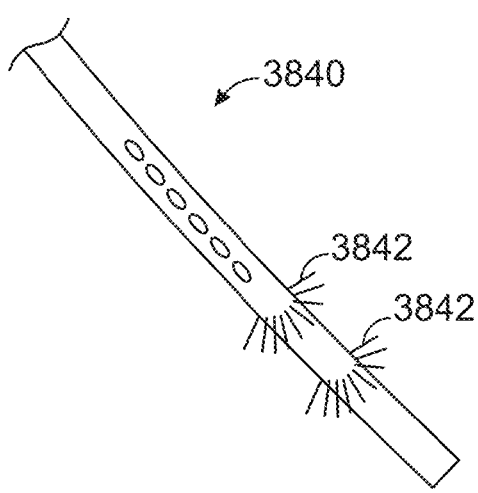
FIG. 38D is an illustrative depiction of a portion of a further embodiment of a fistula irrigation and brushing catheter.

Of course, brushing members having different configurations may be used. For example, FIG. 38B shows a portion of a fistula brushing catheter 3820 having bristles 3822 arranged similar to the bristles of a toothbrush, and FIG. 38C shows a portion of a fistula brushing catheter 3830 having bristles 3832 arranged in a spiral pattern. Additionally, FIG. 38D shows a fistula brushing catheter 3840 having two sets of radially disposed bristles 3842. Of course, these are only exemplary embodiments, and other bristle arrangements may be used in fistula brushing devices. Moreover, some embodiments of fistula brushing devices may include bristles in different regions from those depicted herein.

Figure 39:
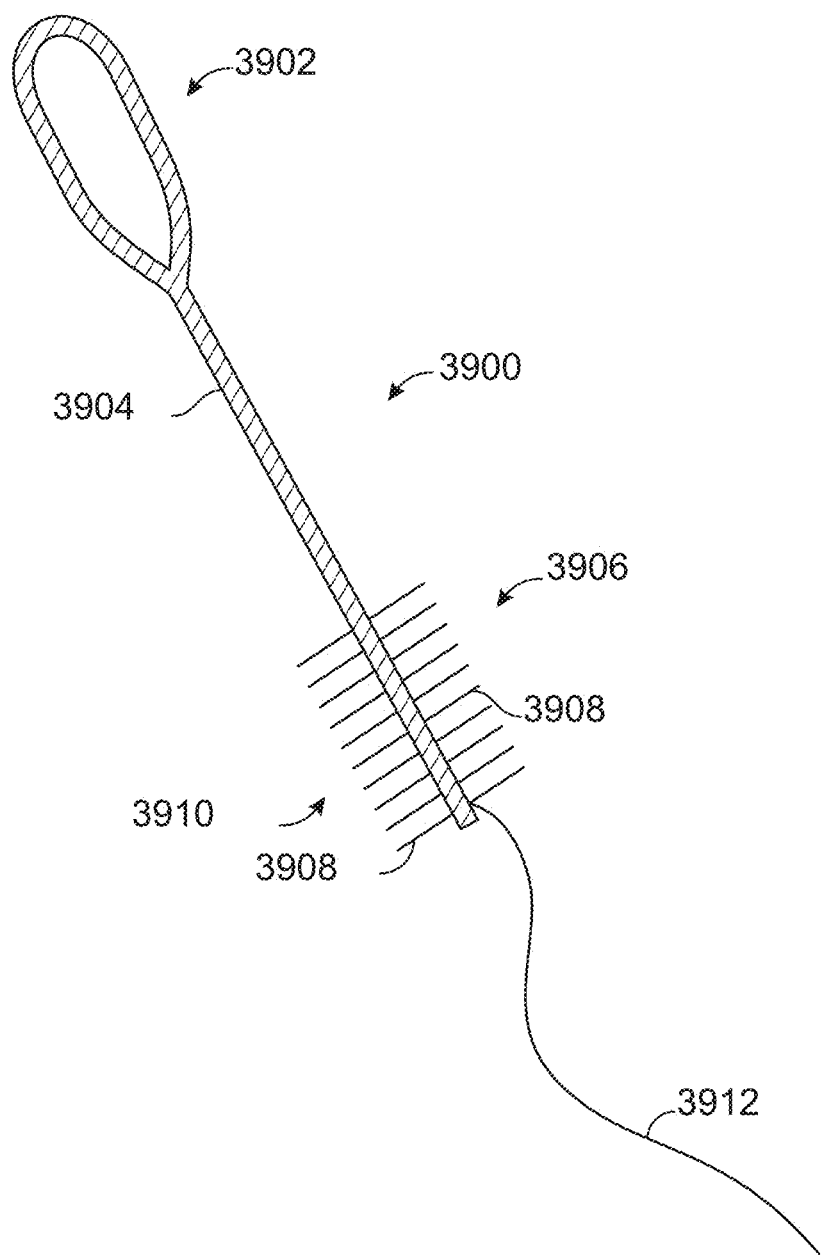
FIG. 39 is an illustrative depiction of an embodiment of a fistula brushing device.

It should be understood that while combination fistula irrigation and brushing or debriding devices have been described, in some cases a fistula treatment device may be configured to brush or debride a fistula tract without also irrigating the tract. Additionally, in some embodiments a fistula brushing device may not be in the form of a catheter. As an example, FIG. 39 shows a fistula brushing device 3900 comprising a proximal handle portion 3902, a shaft 3904 extending from the handle portion 3902, and a brushing member 3906 comprising bristles 3908, where the brushing member 3906 is located in a distal portion 3910 of the shaft 3904. Of course, while not shown here, certain embodiments of fistula brushing devices may include multiple brushing members, or may include one or more brushing members that are not located in a distal portion of the device or a component thereof. As shown, the fistula brushing device 3900 also comprises an elongated member 3912, such as a suture or a string which may be used, for example, to help route the device 3900 into a fistula tract. For example, the elongated member 3912 may be attached to a guidewire that has been routed into a fistula tract, and the guidewire may be pulled upon to advance the fistula brushing device 3900 into the fistula tract. In some embodiments, however, a fistula treatment device may not include such an elongated member, or alternatively may include multiple such elongated members.

Figure 40A:
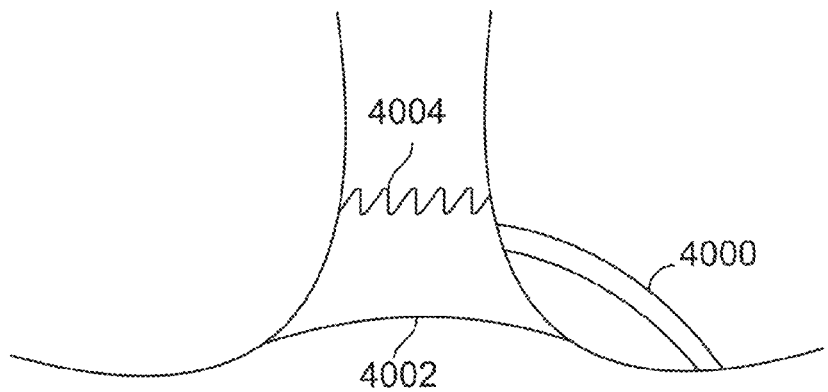
FIGS. 40A-40C provide an illustrative depiction of an embodiment of a method of irrigating a fistula tract.
Figure 40B:
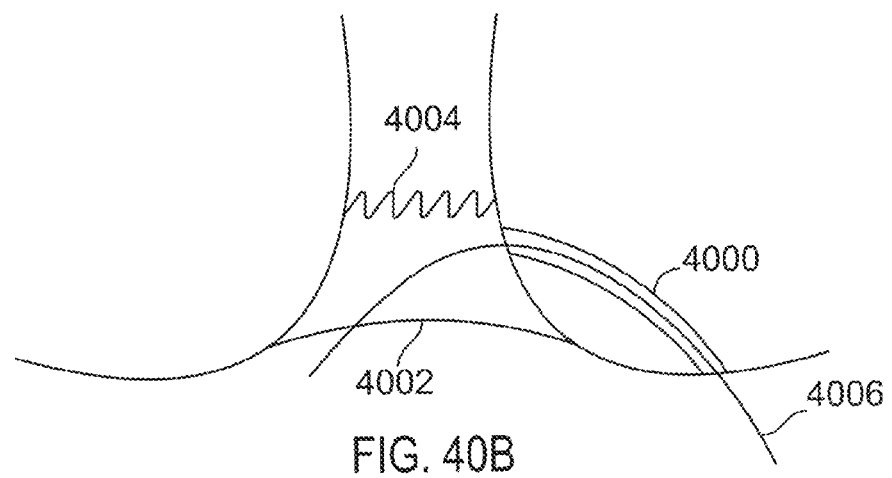
Figure 40C:
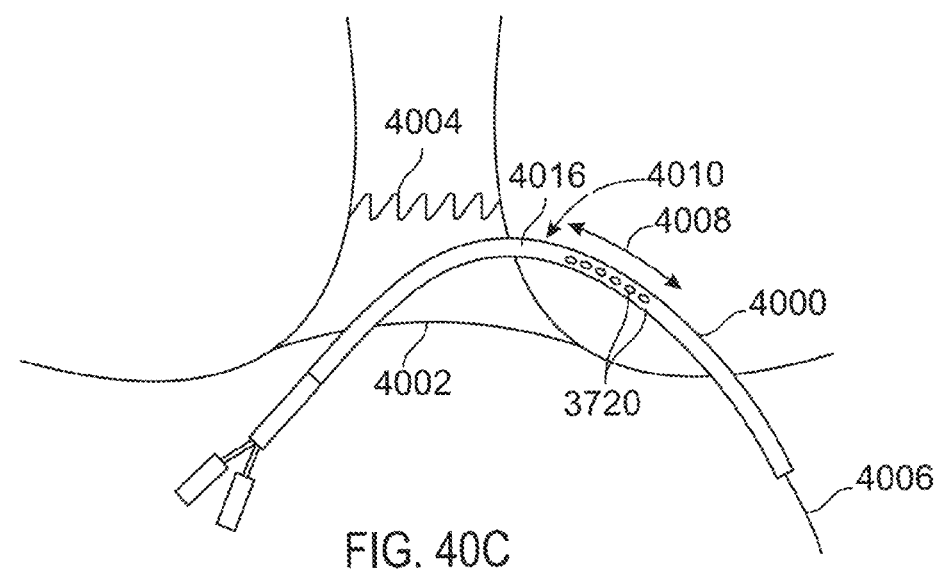

Any appropriate methods may be used to deliver or deploy the fistula treatment devices described herein. For example, FIGS. 40A-40C depict an embodiment of a method of delivering the fistula irrigation catheter 3710 of FIG. 37a into an anorectal fistula tract 4000. First, FIG. 40A shows the fistula tract 4000, by the anus 4002 and the dentate line 4004. In FIG. 40B, a guidewire 4006 has been passed through the fistula tract 4000. Next, and referring to FIG. 40C, the fistula irrigation catheter 3710 has been delivered into the fistula tract 4000, over the guidewire 4006. The guidewire 4006 may be maintained within the catheter 3710 in the fistula tract 4000, or may be removed at this point.

Once the tubular member 3716 with the apertures 3720 is located within the fistula tract, the fistula irrigation catheter 3710 may be grasped at both its proximal and distal ends 3712 and 3714, and moved back and forth within the tract 4000 (e.g., as illustrated by arrow 4008), to effectively "floss" the tract 4000 and thereby irrigate different regions of the tract 4000. This may, for example, provide for good cleaning and minimal contamination of the fistula tract 4000 (e.g., by providing for both proximal and distal irrigation of the fistula tract). Moreover, and as discussed above, the apertures 3720 may be oriented to spray irrigation fluid (e.g., saline) in a non-orthogonal direction—for example, some of the apertures 3720 may be forward-angled and some of the apertures 3720 may be backward-angled, so that bidirectional irrigation may be provided. Additionally, it should be noted that, while not shown here, fistula brushing members or devices may also be moved back and forth within a fistula tract in the manner described above.

To perform the procedures described above, a kit may be provided that contains, for example, one or more fistula irrigation devices, one or more fistula brushing devices, and/or one or more combination fistula irrigation and brushing devices. The kit may also contain one or more other items, including but not limited to a guidewire (e.g., a 0.038" guidewire), a peel-away sheath (e.g., a 7F, 8F, 9F, 10F, or 12F sheath), one or more syringes (e.g., 0.5 cc, 1 cc, 5 cc, and/or 10 cc syringes), saline or biocompatible fluid, contrast media, a scalpel, one or more free needles, and non-resorbable sutures (e.g. 3-0 or 4-0 nylon suture). A fistula tract dilator may also be provided in the kit. The contents of a kit may be provided in sterile packages. Instructions may be provided on or with the kit, or alternatively via the Internet or another indirect method, and may provide direction on how to employ the kit (e.g., outlining a deployment method such as one of those described herein). While preferred embodiments of the present invention have been shown and described herein, it will be obvious to those skilled in the art that those examples are brought by way of example only. Numerous changes, variations, and substitutions will now occur to those skilled in the art without departing from the invention. It should be understood that various alternatives to the embodiments of the invention described herein may be employed in practicing the invention. It is intended that the following claims define the scope of the invention and that the methods and structures within the scope of these claims will be covered thereby.

What is claimed is:

1. A distal anchor for an implantable fistula treatment device, the distal anchor comprising:
    a suture; and
    a plurality of foldable members, including at least a distal-most foldable member and a proximal-most foldable member;
    wherein the distal-most foldable member comprises a suture attachment structure;
    wherein the proximal-most foldable member is configured to couple to a surface of a body lumen at a distal opening of a fistula, wherein the proximal-most foldable member is configured to occlude the fistula at the distal opening, and wherein the proximal-most foldable member is configured to slide along the suture attached to the suture attachment structure;
    wherein the proximal-most foldable member comprises:
        a proximal first average dimension substantially parallel to a longitudinal axis of the suture,
        a proximal second average dimension orthogonal to the proximal first average dimension, and
        a proximal third average dimension orthogonal to the proximal first and second average dimensions, the proximal first average dimension being no greater than 10% of the greater of the proximal second and third average dimensions;
    wherein the distal-most foldable member comprises:
        a distal first average dimension substantially parallel to the longitudinal axis of the suture,
        a distal second average dimension orthogonal to the distal first average dimension, and
        a distal third average dimension orthogonal to the distal first and second average dimensions, the distal first average dimension being no greater than 30% of the greater of the distal second and third average dimensions;
    wherein at least one of the plurality of foldable members comprises a protrusion on a first surface; and
    wherein at least another of the plurality of foldable members comprises a recess on a second surface that opposes the first surface, wherein the protrusion and the recess comprise complementary coupling members, such that the recess is configured to receive the protrusion to restrain relative movement of at least two of the plurality of foldable members.

2. The distal anchor of claim 1, wherein the plurality of foldable members further comprises at least one additional foldable member positioned between the distal-most foldable member and the proximal-most foldable member.

3. The distal anchor of claim 1, wherein the proximal second average dimension of the proximal-most foldable member is larger than the distal second average dimension of the distal-most foldable member.

4. The distal anchor of claim 3, wherein the distal second average dimension of the distal-most foldable member is less than or equal to 20% of the proximal second average dimension of the proximal-most foldable member.

5. The distal anchor of claim 1, wherein the proximal-most foldable member comprises a generally circular perimeter.

6. The distal anchor of claim 5, wherein the proximal-most foldable member comprises a generally concave shape.

7. The distal anchor of claim 6, wherein the distal-most foldable member comprises a generally concave shape, and wherein a radius of curvature of the distal-most foldable member is smaller than a radius of curvature of the proximal-most member.

8. The distal anchor of claim 1, wherein the protrusion on the at least one foldable member comprises at least one tooth.

9. The distal anchor of claim 1, further comprising an additional coupling member disposed between two of the plurality of foldable members, wherein the additional coupling member comprises a curing agent.

10. The distal anchor of claim 9, wherein the additional coupling member further comprises a capsule enclosing the curing agent.

11. The distal anchor of claim 10, where wherein the capsule is configured to rupture upon contact with another foldable member.

12. The distal anchor of claim 1, wherein the coupling members are configured to produce attracting electromagnetic forces.

13. The distal anchor of claim 1, wherein a flexibility of each of the foldable members decreases from the proximal-most to the distal-most foldable member.

14. The distal anchor of claim 13, wherein the proximal first average dimension of the proximal-most foldable member is less than the distal first average dimension of the distal-most foldable member.

15. The distal anchor of claim 13, wherein a density of the proximal-most foldable member is less than a density of the distal-most foldable member.

16. The distal anchor of claim 1, wherein a proximal surface of the proximal-most foldable member comprises a grapple configured to attach the proximal-most foldable member to a surface of the body lumen.

17. The distal anchor of claim 16, wherein a distal surface of the proximal-most foldable member comprises a grapple activation structure configured to activate the grapple upon contact with the proximal surface of another foldable member.

18. The distal anchor of claim 17, wherein the grapple activation structure comprises a protrusion.

19. The distal anchor of claim 1, wherein the protrusion comprises at least two protrusions, and wherein the recess comprises at least two recesses.

20. The distal anchor of claim 1, wherein the distal-most foldable member is pre-attached to the suture at the suture attachment mechanism.

21. The distal anchor of claim 20, wherein the proximal-most foldable member is not pre-attached to the suture.

* * * * *